(12) United States Patent
Altmann et al.

(10) Patent No.: US 7,544,688 B2
(45) Date of Patent: Jun. 9, 2009

(54) HETEREOARYL NITRILE DERIVATIVES

(75) Inventors: Eva Altmann, Reinach (CH); Claudia Betschart, Basel (CH); Kenji Hayakawa, Hyogo Pref. (JP); Osamu Irie, Ibaraki Pref. (JP); Junichi Sakaki, Ibaraki Pref. (JP); Genji Iwasaki, Ibaraki Pref. (JP); Rene Lattmann, Oberwil (CH); Martin Missbach, Gipf-Oberfrick (CH); Naoki Teno, Ibaraki Pref. (JP)

(73) Assignee: Novartis AG, Basel (CH)

( * ) Notice: Subject to any disclaimer, the term of this patent is extended or adjusted under 35 U.S.C. 154(b) by 518 days.

(21) Appl. No.: 10/525,658

(22) PCT Filed: Aug. 29, 2003

(86) PCT No.: PCT/EP03/09621

§ 371 (c)(1),
(2), (4) Date: Aug. 23, 2005

(87) PCT Pub. No.: WO2004/020441

PCT Pub. Date: Mar. 11, 2004

(65) Prior Publication Data

US 2006/0142575 A1 Jun. 29, 2006

(30) Foreign Application Priority Data

Aug. 30, 2002 (GB) .................. 0220187.9

(51) Int. Cl.
*C07D 239/47* (2006.01)
*C07D 239/48* (2006.01)
*A61K 31/505* (2006.01)
*A61K 31/506* (2006.01)
*A61P 19/02* (2006.01)

(52) U.S. Cl. .................. 514/256; 514/269; 544/319; 544/326; 544/320

(58) Field of Classification Search ............ 544/320, 544/326, 319; 514/256, 269
See application file for complete search history.

(56) References Cited

U.S. PATENT DOCUMENTS

2002/0052378 A1  5/2002  Oballa et al.

FOREIGN PATENT DOCUMENTS

| WO | WO 97 09315 | 3/1997 |
| WO | WO 03 020278 | 3/2003 |
| WO | WO 03 020287 | 3/2003 |
| WO | WO 03 020721 | 3/2003 |

OTHER PUBLICATIONS

Wang et al., International Journal of Pharmaceutics, 277, pp. 73-79, 2004.*
Simone, Oncology: Introduction, Cecil Textbook of Medicine, 20m edition, vol. 1, pp. 1004-1010, 1996.*
Wolff Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
Hou et al., Arthritis & Rheumatism, 46(3), 663-674, 2002.*
Caravatti et al., Bioorg. Med. Chem. Lett., 9, 1973-1978, 1999.*
Katoh et al., WO 2003/016266; CA 138: 205074, 2003.*
Chemical Abstracts: 131:266564, Registry No. 245321-46-4, 1999.
Chemical Abstracts 125:300908, Registry No. 99973-07-6, 1996.
Chemical Abstracts 94:208812, Registry Nos. 77768-07-1, 77768-06-0 and 77768-05-9, 1981.
Chemical Abstracts 77:139962, Registry No. 37920-78-8, 1972.
Chemical Abstracts 60: 52751, Registry Nos. 92023-78-4 and 91396-87-1, 1964.
Chemical Abstracts 53: 21997f, Registry No. 105402-10-6, 1959.

* cited by examiner

*Primary Examiner*—Venkataraman Balasubramanian
(74) *Attorney, Agent, or Firm*—John Alexander

(57) ABSTRACT

The invention provides compounds of Formula (I) or a pharmaceutically acceptable salt or ester thereof wherein the symbols have meaning as defined, which are inhibitors of cathepsin K and find use pharmaceutically for treatment of diseases and medical conditions in which cathepsin K is implicated, e.g. various disorders including inflammation, rheumatoid arthritis, osteoarthritis, osteoporosis and tumors.

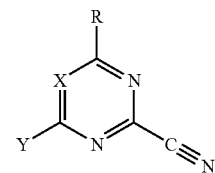

(I)

11 Claims, No Drawings

HETEREOARYL NITRILE DERIVATIVES

This invention relates to inhibitors of cysteine proteases, in particular to heteroaryl nitrile cathepsin K inhibitors and to their pharmaceutical use for the treatment or prophylaxis of diseases or medical conditions in which cathepsin K is implicated.

Cathepsin K is a member of the family of lysosomal cysteine cathepsin enzymes, e.g. cathepsins B, K, L and S, which are implicated in various disorders including inflammation, rheumatoid arthritis, osteoarthritis, osteoporosis, tumors (especially tumor invasion and tumor metastasis), coronary disease, atherosclerosis (including atherosclerotic plaque rupture and destabilization), autoimmune diseases, respiratory diseases, infectious diseases and immunologically mediated diseases (including transplant rejection).

Accordingly the present invention provides a compound of formula I, or a pharmaceutically acceptable salt or ester thereof

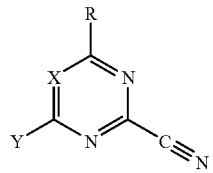

I

In which
R is H, —R2, —OR2 or NR1R2,
wherein R1 is H, lower alkyl or $C_3$ to $C_{10}$ cycloalkyl, and R2 is lower alkyl or $C_3$ to $C_{10}$ cycloalkyl, and
wherein R1 and R2 are independently, optionally substituted by halo, hydroxy, lower alkoxy, CN, $NO_2$, or optionally mono- or di-lower alkyl substituted amino;
X is =N— or =C(Z)-,
wherein Z is H, —R4, —C≡C—$CH_2$—R5, C(P)=C(Q)-R3,
wherein
P and Q independently are H, lower alkyl or aryl,
R3 is aryl, aryl-lower alkyl, $C_3$-$C_{10}$cycloalkyl, $C_3$-$C_{10}$cycloalkyl-lower alkyl, heterocyclyl or heterocyclyl-lower alkyl,
wherein R3 is independently, optionally substituted by one or more groups, e.g. 1-3 groups, selected from halo, hydroxy, oxo, lower alkoxy, CN or $NO_2$, or optionally substituted (optionally mono- or di-lower alkyl substituted amino, aryl, aryl-lower alkyl, N-heterocyclyl or N-heterocyclyl-lower alkyl (wherein the optional substitution comprises from 1 to 3 substituents selected from halo, hydroxy, lower alkoxy, CN, $NO_2$, or optionally mono- or di-lower alkyl substituted amino)),
R4 is H, aryl, aryl-lower alkyl, aryl-lower-alkenyl, $C_3$-$C_{10}$cycloalkyl, $C_3$-$C_{10}$cycloalkyl-lower alkyl, heterocyclyl or heterocyclyl-lower alkyl, and wherein
R5 is aryl, aryl-lower alkyl, aryloxy, aroyl or N-heterocyclyl as defined above, and wherein R5 is optionally substituted by R7 which represents from 1 to 5 substitutents selected from halo, hydroxy, CN, $NO_2$ or oxo, or optionally substituted (lower-alkoxy, lower-alkyl, aryl, aryloxy, aroyl, lower-alkylsulphonyl, arylsulphonyl, optionally mono- or di-lower alkyl substituted amino, or N-heterocyclyl, or N-heterocyclyl-lower alkyl, wherein N-heterocyclyl denotes a saturated, partially unsaturated or aromatic nitrogen containing heterocyclic moiety attached via a nitrogen atom thereof having from 3 to 8 ring atoms optionally containing a further 1, 2 or 3 heteroatoms selected from N, NR6, O, S, S(O) or $S(O)_2$ wherein R6 is H or optionally substituted (lower alkyl, carboxy, acyl (including both lower alkyl acyl, e.g. formyl, acetyl or propionyl, or aryl acyl, e.g. benzoyl), amido, aryl, S(O) or $S(O)_2$), and wherein the N-heterocyclyl is optionally fused in a bicyclic structure, e.g. with a benzene or pyridine ring, and wherein the N-heterocyclyl is optionally linked in a spiro structure with a 3 to 8 membered cycloalkyl or heterocyclic ring wherein the heterocyclic ring has from 3 to 10 ring members and contains from 1 to 3 heteroatoms selected from N, NR6, O, S, S(O) or $S(O)_2$ wherein R6 is as defined above), and wherein heterocyclyl denotes a ring having from 3 to 10 ring members and containing from 1 to 3 heteroatoms selected from N, NR6, O, S, S(O) or $S(O)_2$ wherein R6 is as defined above), and and wherein R7 is optionally substituted by from 1 to 3 substitutents selected from halo, hydroxy, optionally mono- or di- lower-alkyl substituted amino, lower-alkyl carbonyl, lower-alkoxy or lower-alkylamido;
Y is —NR8R9,
wherein
R8 is H, or optionally substituted (lower alkyl, aryl, aryl-lower alkyl, $C_3$-$C_{10}$cycloalkyl, $C_3$-$C_{10}$cycloalkyl-lower alkyl, heterocyclyl or heterocyclyl-lower alkyl),
wherein R8 is optionally substituted by R10 which represents from 1 to 4 substitutents selected from halo, hydroxy, CN, $NO_2$, —O—C(O)—, optionally substituted (lower-alkyl, $C_3$-$C_{10}$cycloalkyl, lower-alkoxy, lower-alkenyl, lower-alkynyl, optionally mono- or di-lower alkyl-substituted amino or N-heterocyclyl (as defined above),
wherein R10 is optionally substituted by R11 which represents from 1 to 4 substituents selected from halo, hydroxy, CN, $NO_2$, oxo, optionally substituted (optionally mono- or di-lower alkyl-substituted amino, lower alkyl, optionally-lower alkyl substituted COOH, sulphinyl, sulphonyl, or N-heterocyclyl (as defined above))
wherein R11 is optionally substituted by R12 which represents from 1 to 4 substituents selected from halo, hydroxy, CN, $NO_2$, oxo, hydroxy lower alkyl, $C_3$-$C_{10}$cycloalkyl, optionally lower alkyl-substituted carboxy, hydroximine, or N-heterocyclyl as defined above, and
wherein
R9 is independently H, or optionally substituted (lower alkyl, aryl, aryl-lower alkyl, $C_3$-$C_{10}$cycloalkyl, $C_3$-$C_{10}$cycloalkyl-lower alkyl, heterocyclyl or heterocyclyl-lower alkyl), and
wherein R9 is optionally substituted by halo, hydroxy, oxo, lower alkoxy, CN, $NO_2$, or optionally mono- or di-lower alkyl substituted amino;
or Z and Y together with the carbon atoms to which they are attached are joined to provide a compound of formula I selected from,

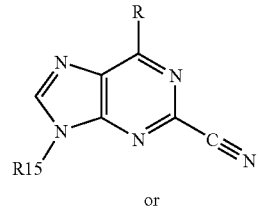

Ib or

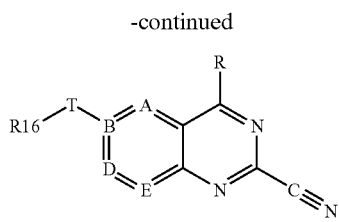

wherein
R is as defined above;
R15 is lower-alkyl, $C_3$-$C_{10}$cycloalkyl, $C_3$-$C_{10}$cycloalkyl-lower alkyl, NR20R21-lower alkyl-, where
T is —O— or a direct bond;
R16 is NR20R21-lower alkyl- or R4, both as defined above, wherein
R20 is H, optionally substituted (lower alkyl, aryl, $C_3$-$C_{10}$cycloalkyl, lower alkoxy lower alkyl $C_3$-$C_{10}$cycloalkyl-lower alkyl or aryl lower alkyl),
R21 is optionally substituted (lower alkyl, aryl, $C_3$-$C_{10}$cycloalkyl, lower alkoxy lower alkyl, $C_3$-$C_{10}$cycloalkyl-lower alkyl or aryl-lower alkyl), or
R20 and R21 form an N-heterocyclyl ring as hereinbefore defined,
and wherein R20 or R21 are independently optionally substituted by R23 which represents from 1 to 3 substitutents selected from halo, hydroxy, CN, $NO_2$, oxo, optionally mono- or di-lower alkyl substituted amino, or optionally substituted (lower-alkoxy, lower-alkyl, lower alkoxy carbonyl, aryl, aryl-lower alkyl, aryl-lower alkenyl, aryloxy, aroyl, alkylsulphonyl, arylsulphonyl or N-heterocyclyl or N-heterocyclyl-lower alkyl (wherein N-heterocyclyl is as defined above)); and
A is —CH═ or —C(O)—, B is —C═ or —N—, D is —CH═ or —C(O)— and E is —CH═ or —N(R1) (where R1 is as defined above).
Above and elsewhere in the present description the following terms have the following meanings.
Halo or halogen denote I Br, Cl or F.
The term "lower" referred to above and hereinafter in connection with organic radicals or compounds respectively defines such as branched or unbranched with up to and including 7, preferably up to and including 5 and advantageously one, two or three carbon atoms.
A lower alkyl group is branched or unbranched and contains 1 to 7 carbon atoms, preferably 1-5 carbon atoms. Lower alkyl represents; for example, methyl, ethyl, propyl, butyl, isopropyl isobutyl, tertiary butyl or neopentyl (2,2-dimethylpropyl).
Halo-substituted lower alkyl is $C_1$-$C_7$ llower alkyl substituted by up to 6 halo atoms.
A lower alkoxy group is branched or unbranched and contains 1 to 7 carbon atoms, preferably 1-4 carbon atoms. Lower alkoxy represents for example methoxy, ethoxy, propoxy, butoxy, isopropoxy, isobutoxy or tertiary butoxy.
A lower alkene, alkenyl or alkenyloxy group is branched or unbranched and contains 2 to 7 carbon atoms, preferably 2-4 carbon atoms and contains at least one carbon-carbon double bond. Lower alkene lower alkenyl or lower alkenyloxy represents for example vinyl, prop-1-enyl, allyl, butenyl, isopropenyl or isobutenyl and the oxy equivalents thereof.
A lower alkyne, alkynyl or alkynyloxy group is branched or unbranched and contains 2 to 7 carbon atoms, preferably 2-4 carbon atoms and contains at least one carbon-carbon triple bond. Lower alkyne or alkynyl represents for example ethynyl, prop-1-ynyl, propargyl, butynyl, isopropynyl or isobutynyl and the oxy equivalents thereof In the present description, oxygen containing substituents, e.g. alkoxy, alkenyloxy, alkynyloxy, carbonyl, etc. encompass their sulphur containing homologues, e.g. thioalkoxy, thioalkenyloxy, thioalkynyloxy, thiocarbonyl, sulphone, sulphoxide etc.

Aryl represents carbocyclic or heterocyclic aryl.

Carbocyclic aryl represents monocyclic, bicyclic or tricyclic aryl, for example phenyl or phenyl mono-, di- or tri-substituted by one, two or three radicals selected from lower alkyl, lower alkoxy, aryl, hydroxy, halogen, cyano, trifluoromethyl, lower alkylenedioxy and oxy-$C_2$-$C_3$-alkylene and other substituents, for instance as described in the examples; or 1- or 2-naphthyl; or 1- or 2-phenanthrenyl. Lower alkylenedioxy is a divalent substituent attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as carbocyclic aryl is naphthyl, phenyl or phenyl optionally substituted, for instance, as described in the examples, e.g. mono- or disubstituted by lower alkoxy, phenyl, halogen, lower alkyl or trifluoromethyl.

Heterocyclic aryl represents monocyclic or bicyclic heteroaryl, for example pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted as defined above.

Preferably, heterocyclic aryl is pyridyl, indolyl, quinolinyl, pyrrolyl, thiazolyl, isoxazolyl, triazolyl, tetrazolyl, pyrazolyl, imidazolyl, thienyl, or any said radical substituted, especially mono- or di-substituted as defined above.

Cycloalkyl represents a saturated cyclic hydrocarbon optionally substituted by lower alkyl which contains 3 to 10 ring carbons and is advantageously cyclopropyl, cyclopentyl, cyclohexyl, cycloheptyl or cyclooctyl optionally substituted by lower alkyl.

N-heterocyclyl is as defined above. Preferred N-heterocyclic substituents are optionally substituted pyrrolidine, pyrrole, diazole, triazole, tetrazole, imidazole, oxazole, thiazole, pyridine, pyrimidine, triazine, piperidine, piperazine, morpholine, phthalimde, hydantoin, oxazolidinone or 2,6-dioxopiperazine and, for example, as hereinafter described in the examples.

In particular embodiments the invention provides a compound of formula Ib, Ic, II or IV or a pharmaceutically acceptable salt or ester thereof

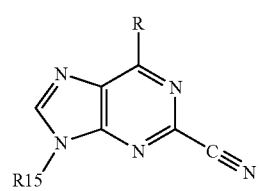

-continued

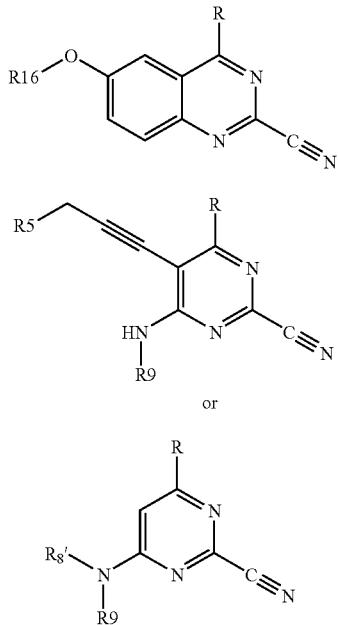

wherein
R8' is H or optionally substituted aryl-lower alkyl
wherein R8' is optionally substituted as defined above for R8, and the other symbols are as defined above.

In a further preferred embodiment the invention provides a compound of formula VI or a pharmaceutically acceptable salt or ester thereof

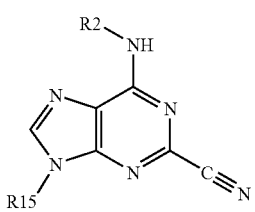

wherein R2 and R15 are as defined above.

R2 is preferably lower alkyl, e.g. straight chain or more preferably branched-chain $C_1$-$C_6$ alkyl, e.g. especially 2-ethylbutyl, isobutyl, or 2,2-dimethylpropyl; or $C_3$-$C_6$cycloalkyl, especially cyclopropyl, cyclopentyl or cyclohexyl.

R15 is preferably 4-lower alkylpiperaz-1-yl-lower alkyl, 4-lower alkylpiperaz-1-yl-lower alkoxy-phenylamino, $C_3$-$C_6$cycloalkyl, $C_3$-$C_6$cycloalkylamino-lower alkyl, imidazo-lower alkyl, morpholino-lower alkyl, lower alkoxy-lower alkylamino-lower alkyl or aryl-lower alkylamino-lower alkyl. For example, R15 is cyclopentyl, 4-methyl-piperaz-1-yl-ethyl, cyclohexylaminoethyl, imidazol-1-ylethyl, morpholinoethyl, methoxyethylaminoethyl, 2-(3-(4-methyl-piperazin-1-yl)-propoxy)-phenylamino or phenylethylaminoethyl.

In a yet further preferred embodiment the invention provides a compound of formula VII or a pharmaceutically acceptable salt or ester thereof

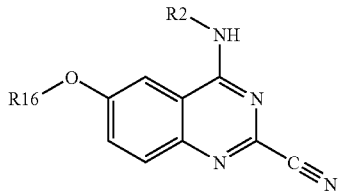

wherein R2 and R16 are as defined above.

Preferred significances for R2 in figure VII are as defined above for figure VI.

R16 is preferably H, aryl-lower alkyl, aryl-lower-alkoxy, 1-lower-alkyl-piperidin-2-yl-lower-alkoxy, 4-lower alkyl-piperazin-1-yl-lower alkyl, 4-lower alkyl-piperaz-1-yl-lower alkoxy, 4-loweralkoxy-lower alkyl-piperaz-1-yl-lower alkyl, 4-loweralkoxy-lower alkyl-piperaz-1-yl-lower alkoxy, di-loweralkylamino-lower alkyl, di-loweralkylamino-lower alkoxy or lower alkyl-piperidyl-lower alkyl. For example, R16 is H, 2-dimethlyamino-ethoxy, 2-(4-methyl-piperazin-1-yl)-ethoxy, 3-(4-propyl-piperazin-1-yl)-propoxy, 3-(4-(2-methoxy-ethyl)-piperazin-1-yl)-propoxy, 3-(4-isopropyl-piperazin-1-yl)-propoxy, pyridin-4-ylmethoxy, pyridin-3-ylmethoxy, pyridin-2-ylmethoxy, 1-methyl-piperidin-2-ylmethoxy, pyrid-3-ylmethyl, pyrid-4-ylmethyl, 4-methyl-piperazin-1-ylethyl, 4-ethyl-piperazin-1-ylpropyl, 4-isopropyl-piperazin-1-ylpropyl, 4-n-propyl-piperazin-1-ylethyl, 4-(2-methoxyethyl)-piperazin-1-ylpropyl, dimethylaminopropyl or 1-methyl-piperid-3-ylmethyl.

In a yet further preferred embodiment the invention provides a compound of formula VIII or a pharmaceutically acceptable salt or ester thereof

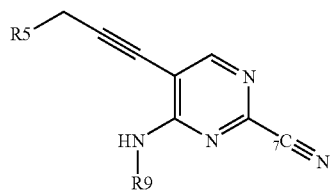

wherein R9 and R5 are as defined above.

R9 is preferably R9' which is lower alkyl, e.g. straight chain or more preferably branched-chain $C_1$-$C_6$ alkyl, e.g. especially 2-ethylbutyl, isobutyl, or 2,2-dimethylpropyl; or $C_3$-$C_6$cycloalkyl, especially cyclopropyl, cyclopentyl or cyclohexyl.

R5 is preferably optionally substituted (aryl-lower-alkyl, N-heterocyclyl-aryl, 1,2,3,4-tetrahydroisoquinlin-yl, aryl-N-heterocyclyl, lower-alkyl-carbonyl-aryl-N-heterocyclyl, aryloxy, N-heterocyclyl, N-heterocyclyl-lower-alkyl-aryloxy, N-heterocyclyl-arylcarbonyl, halo-lower-alkyl-sulphonyl-N-heterocyclyl, lower-alkoxy-aryl-sulphonyl-N-heterocyclyl, dilower-alkylaminoaryl-carbonyl-N-heterocyclyl, lower-alkylcarbonylamino-aryl-sulphonyl-N-heterocyclyl, halo-lower-alkylsulphonyl-N-heterocyclyl or aryl-lower-alkyl-N-heterocyclyl (where N-heterocyclyl is as defined above)).

R5 is preferably optionally substituted by from 1-8 substituents selected from halo, hydroxy, nitro, cyano, amino, oxo, lower-alkyl, lower-alkenyl, lower-alkynyl, $C_3$-$C_{10}$cycloalkyl, $C_3$-$C_{10}$cycloalkyl-lower-alkyl, $C_3$-$C_{10}$cycloalkylamino, lower-alkoxy, lower-alkoxy-lower-alkyl, lower-alkoxy-lower-alkoxy-lower-alkyl, halo-lower-alkyl, lower-alkyl-carbonyl, aryl, aryl-lower-alkyl, halo-aryl-lower-alkyl, halo-aryloxy-lower-alkyl-carbonyl, lower-alkyl-sulphonyl, lower-alkyl-carbonyl, lower-alkoxy-carbonyl, sulphonamido, lower-alky-carbonyl-aryl, aryl, lower-alkyl-N-heterocyclyl-lower-alkyl, lower-alkylamino. Halo-lower-alkyl-sulphonyl, lower-alkoxy-aryl-sulphonyl, dilower-alkylamino-aryl-carbonyl, lower-alkyl-amido-aryl-sulphonyl or halo-lower-alkyl-sulphonyl.

For example, R5 is benzyl, 4-(4-methyl-piperazin-1-yl)-phenyl, 3,4-dihydro-1 H-isoquinolin-2-yl, 4-phenyl-piperazin-1-yl, 4-(4-methylcarbonylphenyl)-piperazin-1-yl, 4-phenyl-4-hydroxy-piperidin-1-yl, isoindol-2-yl, isoindol-1-yl, 4-pyridin-2-yl-piperazin-1-yl, pyridin-3-yloxy, imidazol-1-yl, 4,5-dichloro-imidazol-1-yl, 4-(4-methyl-piperazin-1-ylmethyl)-phenoxy, 4-[1,2,3]triazol-1-yl-benzoyl, 4-(3-chloro-propane-1-sulfonyl)-piperazin-1-yl, 4-(4-methoxy-phenyl-sulfonyl)-piperazin-1-yl, 4-(4-dimethylaminophenyl-carbonyl)-piperazin-1-yl, 4-(4-methylcarbonylaminophenyl-sulfonyl)-piperazin-1-yl, 4-(3-chloropropyl-sulfonyl)-piperazin-1-yl and 4-benzyl-2,6-dioxo-piperazin-1-yl.

In a yet further preferred embodiment the invention provides a compound of formula IX or a pharmaceutically acceptable salt or ester thereof

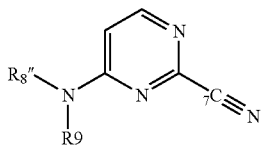

IX wherein R9 is as defined above and R8" is optionally substituted aryl-lower alkyl as defined above for R8'.

R9 is preferably R9' which is lower alkyl, e.g. straight chain or more preferably branched-chain $C_1$-$C_6$-alkyl, e.g. especially 2-ethylbutyl, isobutyl, or 2,2-dimethylpropyl; or $C_3$-$C_6$cycloalkyl, especially cyclopropyl, cyclopentyl or cyclohexyl.

R8" is preferably optionally substituted (N-heterocyclyl-loweralkynyl-aryl-loweralkyl, N-heterocyclyl-N-heterocyclyl-loweralkynyl-aryl-loweralkyl, loweralkylsulfonyl-N-heterocyclyl-loweralkynyl-aryl-loweralkyl, $C_3$-$C_{10}$cyclcloalkylamino-loweralkynyl-aryl-loweralkyl, N-heterocyclylamino-loweralkynyl-aryl-loweralkyl, N-heterocyclyl-loweralkynyl-aryl-loweralkyl, amino-loweralkyl-N-heterocyclyl-loweralkynyl-aryl-loweralkyl, carboxy-N-heterocyclyl-loweralkynyl-aryl-loweralkyl, hydroxy-loweralkyl-N-heterocyclyl-loweralkynyl-aryl-loweralkyl, N-heterocyclyl-loweralkylamino-loweralkynyl-aryl-loweralkyl, amino-loweralkynyl-aryl-loweralkyl, N-heterocyclyl-aminocarbonyl-N-heterocyclyl-loweralkynyl-aryl-loweralkyl, di-loweralkyl-aminocarbonyl-N-heterocyclyl-loweralkynyl-aryl-loweralkyl, hydroxy-N-heterocyclyl-loweralkynyl-aryl-loweralkyl, N-heterocyclyl-aryl-loweralkyl, loweralkyl-aryl-loweralkyl, loweralkynyl-aryl-loweralkyl, N-heterocyclyl-loweralkyl-aryl-loweralkyl, loweralkyl-carbonyl-N-heterocyclyl-loweralkyl-aryl-loweralkyl, loweralkyl-sulfonyl-N-heterocyclyl-loweralkyl-aryl-loweralkyl, N-heterocyclyl-sulfonyl-N-heterocyclyl-aryl-loweralkyl, loweralkyl-sulfonyl-loweralkyl-aryl-loweralkyl, hydroxy-N-heterocyclyl-loweralkyl-aryl-loweralkyl, N-heterocyclylcarbonyloxy-loweralkyl-aryl-loweralkyl, N-heterocyclyl-loweralkynyl-aryl-loweralkyl, loweralkyl-sulphonyl-N-heterocyclyl-loweralkynyl-aryl-loweralkyl, N-heterocyclyl-N-heterocyclyl-loweralkynyl-aryl-loweralkyl or loweralkynyl-aryl-loweralkyl (where N-heterocyclyl is as defined above)).

R8" is preferably optionally substituted by from 1-8 substituents selected from halo, hydroxy, nitro, cyano, amino, oxo, lower-alkyl, lower-alkenyl, lower-alkynyl, $C_3$-$C_{10}$cycloalkyl, $C_3$-$C_{10}$cycloalkyl-lower-alkyl, $C_3$-$C_{10}$cycloalkylamino, lower-alkoxy, lower-alkoxy-lower-alkyl, lower-alkoxy-lower-alkoxy-lower-alkyl, halo-lower-alkyl,lower-alkyl-carbonyl, aryl, aryl-lower-alkyl, halo-aryl-lower-alkyl, halo-aryloxy-lower-alkyl-carbonyl, lower-alkyl-sulphonyl, lower-alkyl-carbonyl, lower-alkoxy-carbonyl, sulphonamido, lower-alky-carbonyl-aryl, aryl, lower-alkyl-N-heterocyclyl-lower-alkyl, lower-alkylamino. Halo-lower-alkyl-sulphonyl, lower-alkoxy-aryl-sulphonyl, dilower-alkylamino-aryl-carbonyl, lower-alkyl-amido-aryl-sulphonyl or halo-lower-alkyl-sulphonyl.

For example R8" is 4-(3-(4-acetyl-piperazin-1-yl)-prop-1-ynyl)-benzyl, 4-(3-(4-formyl-piperazin-1-yl)-prop-1-ynyl)-benzyl, 4-(3-piperidin-1-yl-prop-1-ynyl)-benzyl, 4-(3-(4-methyl-piperazin-1-yl)-prop-1-ynyl)-benzyl, 4-(3-pyrrol-1-yl-prop-1-ynyl)-benzyl, 4-(3-(4-piperidin-1-yl-piperidin-1-yl)-prop-1-ynyl)-benzyl, 4-(3-(4-ethyl-piperazin-1-yl)-prop-1-ynyl)-benzyl, 4-(3-(4-isopropyl-piperazin-1-yl)-prop-1-ynyl)-benzyl, 4-(3-(4-n-propylsulfonyl-piperazin-1-yl)-prop-1-ynyl)-benzyl, 4-(3-(4-hydroxy-piperazin-1-yl)-prop-1-ynyl)-benzyl, 4-(3-(4-oxo-piperazin-1-yl)-prop-1-ynyl)-benzyl, 4-(3-(cyclohexylamino)-prop-1-ynyl )-benzyl, 4-(3-(piperidin-1-ylamino)-prop-1-ynyl)-benzyl, 4-(3-(4-aminomethyl-piperidin-1-yl)-prop-1-ynyl)-benzyl, 4-(3-(4-hydroxycarbonyl-piperidin-1-yl)-prop-1-ynyl)-benzyl, 4-( 3-(4-hydroxymethyl-piperidin-1-yl)-prop-1-ynyl)-benzyl, 4-(3-(morpholinoethylamino)-prop-1-ynyl)-benzyl, 4-(3-(piperidinylethylamino)-prop-1-ynyl)-benzyl, 4-(3-(imidazol-1-yl)-prop-1-ynyl)-benzyl, 4-(3-([1,2,4]-triazol-1-yl)-prop-1-ynyl)-benzyl, 4-(3-amino-prop-1-ynyl)-benzyl, 4-(3-(4-[1,2,4]triazol-4-ylamido-piperidin-1-yl)-prop-1-ynyl)-benzyl, 4-( 3-(4-dimethylaminocarbonylpiperidin-1-yl)-prop-1-ynyl)-benzyl, 4-(3-piperidin-1-yl)-prop-1-ynyl)-benzyl, 4-(3-(4-hydroxy-piperidin-1-yl)-prop-1-ynyl)-benzyl, 4-[1,2,4]triazol-1-yl-benzyl, 4-imidazol-1-yl-benzyl, 4-vinyl-benzyl, 4-(3-methyl-3H-imidazol-4-yl)-benzyl, 4-oxazol-2-yl-benzyl, 4-[1,2,4]triazol-1-ylmethyl-benzyl, 4-imidazol-1-ylmethyl-benzyl, 4-ethyl-benzyl, 3-(3-(4-acetyl-piperazin-1-yl)-propyl)-benzyl, 3-(3-(4-ethylsulfonyl-piperazin-1-yl)-propyl)-benzyl, 3-(3-(4-oxo-piperidin-1-yl)-propyl)-benzyl, 3-( 3-(4-hydroxylamino-piperidin-1-yl)-propyl)-benzyl, 4-(3-piperidin-1-yl-propyl)-benzyl, 4-(2-methylsulfonyl-1-methyl-ethyl)-benzyl, 4-(3-piperidin-1-yl-propyl)-benzyl, 4-( 3-(4-hydroxy-piperidin-1-yl)-propyl)-benzyl, 4-(3-(piperidin-4-yl-carbonyloxy)-propyl)-benzyl, 4-((E)-3-piperidin-1-yl-propenyl)-benzyl, 4-((E)-3-(2,6-dioxo-piperidin-1-yl)-propenyl)-benzyl, 4-((l)-3-(4-hydroxy-piperidin-1-yl)-propenyl)-benzyl, 4-((E)-3-(4-hydroxycarbonyl-piperidin-1-yl)-propenyl)-benzyl, 4-((E)-3-pyrrolo-1-yl-propenyl)-benzyl, 4-((E)-3-(4-methylcarbonyl-piperazin-1-yl)-propenyl)-benzyl, 4-((E)-3-(4-methyl-piperazin-1-yl)-propenyl)-benzyl, 4-((E)-3-(4-ethyl-piperazin-1-yl)-propenyl)-benzyl, 4-((E)-3-(4-ethylsulfonyl-piperazin-1-yl)-propenyl)-benzyl, 4-((E)-3-(4-piperidin-1-yl-piperidin-1-yl)-propenyl)-benzyl, 4-((E)-2-cyano-vinyl)-benzyl, 4-((E)-2-([1,2,4]-triazol-1-yl)-vinyl)-benzyl, 4-((E)-2-([1,2,3]- triazol-1-yl)-vinyl)-benzyl, 4-(3-(4-hydroxyamino-piperidi-1-yl)-prop-1-ynyl)-benzyl and 4-((E)-3-piperidin-1-yl-propenyl)-benzyl.

Particularly preferred compounds of the invention are the compounds of the examples Compounds of formula VI or pharmaceutically acceptable salts or esters thereof

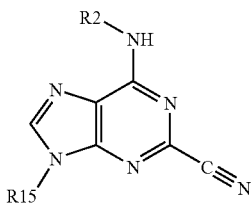

VI wherein R2 and R15 are as defined above, may be prepared by cyanation of a corresponding 2-halo precursor of formula XIV

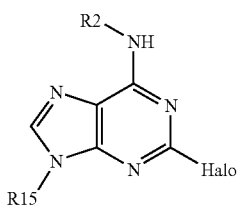

XIV wherein R2 and R15 are as defined above and Halo is preferably Cl; for instance substantially as described in the examples.

Compounds of formula VII or pharmaceutically acceptable salts or esters thereof

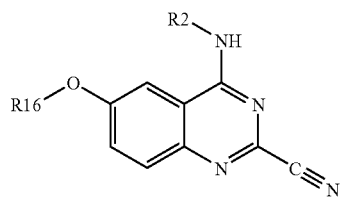

VII wherein R2 and R16 are as defined above, may be prepared by coupling of a 6-hydroxy precursor of formula XV with an R16-Halo precursor

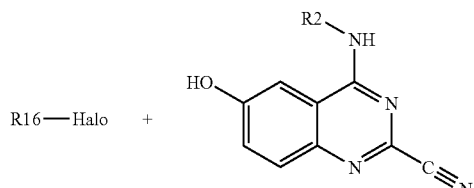

XV wherein R2 and R16 are as defined above and Halo preferably Cl; for instance, substantially as described in the examples.

Compounds of formula VIII or pharmaceutically acceptable salts or esters thereof

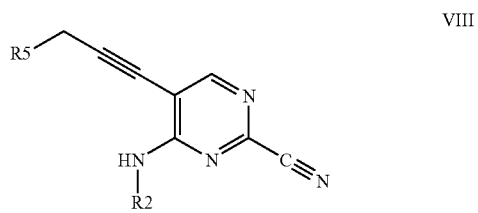

VIII wherein R2 and R5 are as defined above, may be prepared by coupling of a 5-halopyrimidine precursor of formula XVI with a corresponding R5-$CH_2$—C≡CH propyne

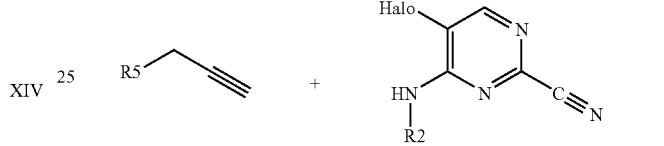

XVI wherein R2 and R5 are as defined above and Halo is preferably Br; for instance, substantially as described in the examples.

Compounds of formula IX or pharmaceutically acceptable salts or esters thereof

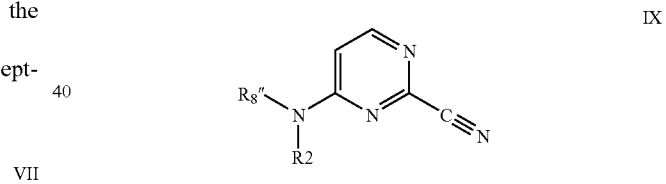

IX wherein R2 is as defined above and R8" is optionally substituted aryl-lower alkyl as defined above for R8', may be prepared by coupling of a secondary amine precursor of formula XVII

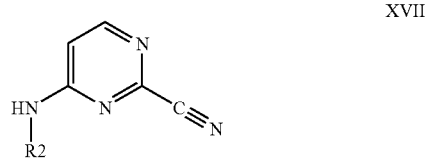

XVII wherein R2 is as defined above, with a corresponding R8"-Halo precursor, wherein Halo is preferably I; for instance, substantially as described in the examples.

The above coupling, cyclisation and cyanation reactions may be carried out under various conditions and in the presence of solvents and other reagents as required, including catalysts and co-factors as known in the art and for instance, as hereinafter described in the examples.

The starting materials may be prepared and the coupled and cyclised products may be converted into other compounds of formula V and salts and esters thereof using methods and procedures known in the art, and as hereinafter described in the examples.

Accordingly the present invention further provides processes for the preparation of compounds of Formula I

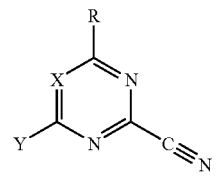

as hereinbefore defined, comprising i) for the preparation of compounds of formula VI or pharmaceutically acceptable salts or esters thereof

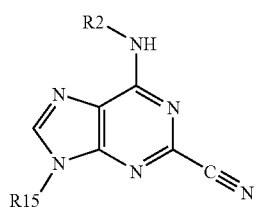

wherein R2 and R15 are as defined above, cyanation of a corresponding 2-halo precursor of formula XIV

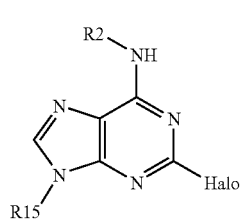

wherein R2 and R15 are as defined above and Halo is preferably Cl;

ii) for preparation of compounds of formula VII or pharmaceutically acceptable salts or esters thereof

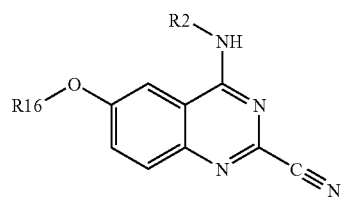

wherein R2 and R16 are as defined above, coupling of a 6-hydroxy precursor of formula XV with an R16-Halo precursor

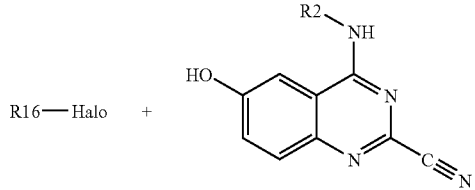

wherein R2 and R16 are as defined above and Halo is preferably Cl;

iii) for the preparation of compounds of formula VIII or pharmaceutically acceptable salts or esters thereof

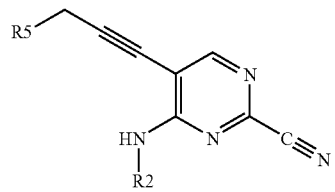

wherein R2 and R5 are as defined above, coupling of a 5-halopyrimidine precursor of formula XVI with a corresponding R5—CH$_2$—C≡CH propyne

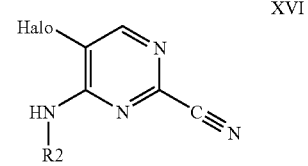

wherein R2 and R5 are as defined above and Halo is preferably Br;

iv) for the preparation of compounds of formula IX or pharmaceutically acceptable salts or esters thereof

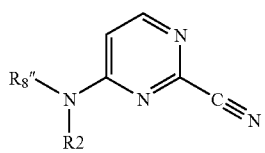

wherein R2 is as defined above and R8″ is optionally substituted aryl-lower alkyl as defined above for R8′, coupling of a secondary amine precursor of formula XVII

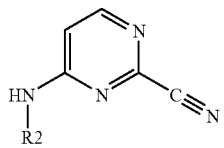

XVII wherein R2 is as defined above, with a corresponding R8"-Halo precursor, wherein Halo is preferably I;

v) thereafter, if desired, converting the product obtained into a further compound of formula I, or into a salt or ester thereof Compounds of the invention are either obtained in the free form, or as a salt thereof if salt forming groups are present.

Compounds of the Invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$-$C_4$)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$-$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The compounds of the invention exhibit valuable pharmacological properties in mammals and are particularly useful as inhibitors of cathepsin K.

The cathepsin K inhibitory effects of the compound of the invention can be demonstrated in vitro by measuring the inhibition of e.g. recombinant human cathepsin K.

The In Vitro Assay is Carried Out as Follows:

For cathepsin K:

The assay is performed in 96 well microtiter plates at ambient temperature using recombinant human cathepsin K. Inhibition of cathepsin K is assayed at a constant enzyme (0.16 nM) and substrate concentration (54 mM Z-Phe-Arg-AMCA-Peptide Institute Inc. Osaka, Japan) in 100 mM sodium phosphate buffer, pH 7.0, containing 2 mM dithiothreitol, 20 mM Tween 80 and 1 mM EDTA. Cathepsin K is preincubated with the inhibitors for 30 min, and the reaction is initiated by the addition of substrate. After 30 min incubation the reaction is stopped by the addition of E-64 (2 mM), and fluorescence intensity is read on a multi-well plate reader at excitation and emission wavelengths of 360 and 460 nm, respectively. Compounds of the Invention typically have Kis for human cathepsin K of less than about 50 nM, preferably of about 5 nM or less, e.g. about 1 nM.

In view of their activity as inhibitors of cathepsin K, Compounds of the Invention are particularly useful in mammals as agents for treatment and prophylaxis of diseases and medical conditions involving elevated levels of cathepsin K. Such diseases include diseases involving infection by organisms such as pneumocystis carinii, trypsanoma cruzi, trypsanoma brucei, crithidia fusiculata, as well as parasitic diseases such as schistosomiasis and malaria, tumours (tumour invasion and tumour metastasis), and other diseases such as metachromatic leukodystrophy, muscular dystrophy, amytrophy and similar diseases.

Cathepsin K, has been implicated in diseases of excessive bone loss, and thus the Compounds of the Invention may be used for treatment and prophylaxis of such diseases, including osteoporosis, gingival diseases such as gingivitis and periodontitis, Paget's disease, hypercalcemia of malignancy, e.g. tumour-induced hypercalcemia and metabolic bone disease. Also the Compounds of the Invention may be use for treatment or prophylaxis of diseases of excessive cartilage or matrix degradation, including osteoarthritis and rheumatoid arthritis as well as certain neoplastic diseases involving expression of high levels of proteolytic enzymes and matrix degradation.

Compounds of the Invention, are also indicated for preventing or treating coronary disease, atherosclerosis (including atherosclerotic plaque rupture and destabilization), autoimmune diseases, respiratory diseases and immunologically mediated diseases (including transplant rejection).

Compounds of the Invention are particularly indicated for preventing or treating osteoporosis of various genesis (e.g. juvenile, menopausal, post-menopausal, post-traumatic, caused by old age or by cortico-steroid therapy or inactivity).

Beneficial effects are evaluated in in vitro and in vivo pharmacological tests generally known in the art, and as illustrated herein.

The above cited properties are demonstrable in in vitro and in vivo tests, using advantageously mammals, e.g. rats, mice, dogs, rabbits, monkeys or isolated organs and tissues, as well as mammalian enzyme preparations, either natural or prepared by e.g. recombinant technology. Compounds of the Invention can be applied in vitro in the form of solutions, e.g. preferably aqueous solutions or suspensions, and in vivo either enterally or parenterally, advantageously orally, e.g. as a suspension or in aqueous solution, or as a solid capsule or tablet formulation. The dosage in vitro may range between about $10^{-5}$ molar and $10^{-9}$ molar concentrations. The dosage in vivo may range, depending on the route of administration, between about 0.1 and 100 mg/kg.

The antiarthritic efficacy of the Compounds of the Invention for the treatment of rheumatoid arthritis can be determined using models such as or similar to the rat model of adjuvant arthritis, as described previously (R. E. Esser, et. al. J. Rheumatology, 1993, 20, 1176.)

The efficacy of the compounds of the invention for the treatment of osteoarthritis can be determined using models such as or similar to the rabbit partial lateral meniscectomy model, as described previously (Colombo et al. Artl. Rheum. 1993 26, 875-886). The efficacy of the compounds in the model can be quantified using histological scoring methods, as described previously (O'Byrne et al. Inflamm Res 1995, 44, S117-S118).

The efficacy of the compounds of the invention for the treatment of osteoporosis can be determined using an animal model such as the ovariectomised rat or other similar species, e.g. rabbit or monkey, in which test compounds are administered to the animal and the presence of markers of bone resorption are measured in urine or serum (e.g. as described in Osteoporos Int (1997) 7:539-543).

Accordingly in further aspects the invention provides:

A Compound of the Invention for use as a pharmaceutical; a pharmaceutical composition comprising a Compound of the Invention as an active ingredient;

a method of treating a patient suffering from or susceptible to a disease or medical condition in which cathepsin K is implicated, comprising administering an effective amount of a Compound of the Invention to the patient, and the use of a Compound of the Invention for the preparation of a medicament for therapeutic or prophylactic treatment of a disease or medical condition in which cathepsin K is implicated.

The present invention relates to methods of using Compounds of the Invention and their pharmaceutically acceptable salts, or pharmaceutical compositions thereof, in mammals for inhibiting cathepsin K, and for the treatment of cathepsin K dependent conditions, such as the cathepsin K dependent conditions, described herein, e.g. inflammation, osteoporosis, rheumatoid arthritis and osteoarthritis.

Particularly the present invention relates to a method of selectively inhibiting cathepsin K activity in a mammal which comprises administering to a mammal in need thereof an effective cathepsin K inhibiting amount of a Compound of the Invention.

More specifically such relates to a method of treating osteoporosis, rheumatoid arthritis, osteoarthritis, and inflammation (and other diseases as identified above) in mammals comprises administering to a mammal in need thereof a correspondingly effective amount of a Compound of the Invention.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20-133 mbar). The structure of final products, intermediates and starting materials is confirmed by standard analytical methods, e.g. microanalysis and spectroscopic characteristics (e.g. MS, IR, NMR). Abbreviations used are those conventional in the art.

EXAMPLES

Example 10 describes the preparation of purine-2-carbonitriles

Example 10-1

Synthesis of 6-Cyclohexylamino-9-cyclopentyl-purine-2-carbonitrile

A. (2-Chloro-purin-6-yl)-cyclohexyl-amine

To a solution of 2,6-Dichloro-purine (10 mmol) in 1-pentanol (20 ml) cyclohexylamin (30 mmol) is added and the stirred mixture is heated at 70° C. for 4 hours. The heating bath is removed and after cooling down to RT the precipitate formed is filtered off and washed with ethanol, diethylether and dried (vacuum). A solid powder with mp. 265° C. (decomp.), Rf=0.34 ($CH_2Cl_2$/MeOH=9:1) is obtained.

B. (2-Chloro-9-cyclopentyl-purin-6-yl)-cyclohexyl-amine

2-Chloro-6-cyclohexylamino-purine (10 mmol), bromocyclopentane (20 mmol) and potassium carbonate (20 mmol, water free) in DMF (70 ml) are heated up to 50° C. and the mixture is stirred at this temperature for 10 hours. After cooling to RT the mixture is poured on water and extracted 3 times with ethyl acetate. The combined organic phases are washed twice with brine and the extract is dried over sodium sulfate and evaporated. A pale oil with Rf=0.36 ($CH_2Cl_2$/MeOH=20:1) is obtained.

C. 6-Cyclohexylamino-9-cyclopentyl-purine-2-carbonitrile

2-Chloro-6-cyclohexylamino-9-cyclopentyl-purine (6.3 mmol) and sodium cyanide (36 mmol) are heated up in DMF (30 ml) to 160° C. for 70 hours. After cooling down to RT the mixture is poured on water and extracted 3 times with ethyl acetate. The combined organic phases are washed with brine and the extract is dried over sodium sulfate and evaporated. The residue is purified by flash chromatography on silica gel with ethyl acetate as mobile phase. The product containing fractions are combined and evaporated. A pale yellow oil with Rf=0.33 (ethyl acetate) is obtained.

$^1$H-NMR ($CDCl_3$): 1.2-1.55 (m, 5H), 1.6-2.1 (m, 11H), 2.2-2.4 (m, 2H), 4.05-4.2 (m, 1H), 4.854.95 (m, 1H), 5.7-5.9 (broad signal, 1H), 7.9 (s, 1H).

Example 10-2

6-Cyclohexylamino-9-(2-imidazol-1-yl-ethyl)-purine-2-carbonitrile

A: [2-Chloro-9-(2-chloro-ethyl)-purin-6-yl]-cyclohexyl-amine

2-Chloro-6-cyclohexylamino-purine (4 mmol), 1-bromo-2-chloroethane (8 mmol) and potassium carbonate (8 mmol, water free) in DMF (20 ml) are heated up to 45° C. and the mixture is stirred at this temperature for 5 hours. After cooling to RT the mixture is poured on water and extracted 3 times with ethyl acetate. The combined organic phases are washed twice with brine and the extract is dried over sodium sulfate and evaporated. The residue is dissolved in diethylether and pentane is added. The solid material formed is filtered of and dried (vacuum). A white powder with mp. 150-152° C., Rf=0.17 ($CH_2Cl_2$/MeOH=20:1) is obtained.

B: [2-Chloro-9-(2-imidazol-1-yl-ethyl)-9-purin-6-yl]-cyclohexyl-amine

[2-Chloro-9-(2-chloro-ethyl)-purin-6-yl]-cyclohexyl-amine (1 mmol) and sodium imidazol (1.3 mmol) are dissolved in DMF (10 ml) and heated up to 80° C. and the mixture is stirred at this temperature for 7 hours. After evaporation of the solvent, the residue is dissolved in water and extracted three times with ethyl acetate. The combined extract is dried over sodium sulfate and evaporated. The residue is purified by flash chromatography on silica gel with ($CH_2Cl_2$/MeOH=10:1) as mobile phase. The product containing fractions are combined and evaporated. A pale oil with Rf=0.40 ($CH_2Cl_2$/MeOH=10:1) is obtained.

C: 6-Cyclohexylamino-9-(2-imidazol-1-yl-ethyl)-purine-2-carbonitrile

[2-Chloro-9-(2-imidazol-1-yl-ethyl)-9-purin-6-yl]-cyclohexyl-amine (0.6 mmol) and sodium cyanide (2 mmol) are heated up in DMA (3 ml) to 160° C. and the mixture is stirred at this temperature for 20 hours. After cooling down to RT the mixture is poured on water and extracted 3 times with ethyl acetate. The combined organic phases are washed with brine and the extract is dried over sodium sulfate and evaporated. The residue is suspended in $CH_2Cl_2$ and the solid material filtered off. The filtrate is concentrated and the obtained residue purified by flash chromatography on silica gel with ($CH_2Cl_2$/MeOH=20:1) as mobile phase. The product containing fractions are combined and evaporated. A solid powder with mp. 115-117° C., Rf=0.59 ($CH_2Cl_2$/MeOH=10:1) is obtained.

$^1$H-NMR (CDCl$_3$): 0.8-0.9 (m, 1H), 1.2-1.85 (m, 1H), 2.0-2.2 (m, 2H), 4.05-4.2 (br. m, 1H), 5.2 (d, 1H), 5.7-5.8 (br. m, 1H), 5.9 (d, 1H), 7.2 (m, 1H), 8.05 (s, 1H).

The compounds of formula 10-1 as identified below in Table 10-1 are prepared analogously to the above examples immediately above, starting from the corresponding 2,4-dichloropurines.

TABLE 10-1

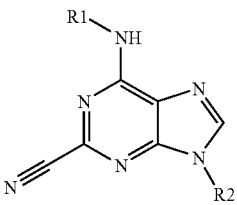

10-1

| Exple No. | R1 (* indicates the bond to the nitrogen) | R2 (* indicates the bond to the nitrogen) | RF-value (mobile phase) | Melting point or molecular weight by MS |
|---|---|---|---|---|
| 10-3 | cyclohexyl-CH$_2$-* | *-CH$_2$CH$_2$-N(piperazine)-N-CH$_3$ | 0.32 ($CH_2Cl_2$/MeOH = 9:2) | 166-168° C. |
| 10-4 | cyclohexyl-CH$_2$-* | *-CH$_2$CH$_2$-NH-cyclohexyl | 0.29 ($CH_2Cl_2$/MeOH = 10:1) | 153-155° C. |
| 10-5 | isobutyl-* | *-CH$_2$CH$_2$-imidazol-1-yl | 0.29 ($CH_2Cl_2$/MeOH = 10:1) | 150° C. |
| 10-6 | isobutyl-* | *-CH$_2$CH$_2$-N(piperazine)-N-CH$_3$ | 0.16 ($CH_2Cl_2$/MeOH = 10:1) | M$^+$ = 343.3 |
| 10-7 | isobutyl-* | *-CH$_2$CH$_2$-morpholine | 0.34 ($CH_2Cl_2$/MeOH = 20:1) | M$^+$ = 330.3 |
| 10-8 | isobutyl-* | *-CH$_2$CH$_2$-NH-CH$_2$CH$_2$-O-CH$_3$ | 0.25 ($CH_2Cl_2$/MeOH = 10:1) | 75-76° C. |
| 10-9 | cyclopentyl-CH$_2$-* | *-CH$_2$CH$_2$-NH-CH$_2$CH$_2$-O-CH$_3$ | 0.16 ($CH_2Cl_2$/MeOH = 10:1) | 108-110° C. |

TABLE 10-1-continued 10-1

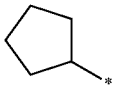

| Exple No. | R1 (* indicates the bond to the nitrogen) | R2 (* indicates the bond to the nitrogen) | RF-value (mobile phase) | Melting point or molecular weight by MS |
|---|---|---|---|---|
| 10-10 | 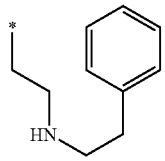 | | 0.22 (CH$_2$Cl$_2$/MeOH = 10:1) | 132-133° C. |

Example 10-11

Synthesis of 9-Cyclopentyl-6-{2-[3-(4-methyl-piperazin-1-yl)-propoxy]-phenylamino}-purine-2-carbonitrile

A: 1-(3-Chloro-propoxy)-2-nitro-benzene

2-Nitrophenol (70 mmol), 1-bromo-3-chloropropane (360 mmol), potassium carbonate (water free, 110 mmol), potassium iodide (2 mmol) and tetrabutyl-ammonium bromide (1 mmol) are suspended in acetone (130 ml) and heated up to 50° C. and the mixture is then stirred at this temperature for 30 hours. After cooling down to RT the solid material is filtered off and the filtrate is evaporated. The excess of 1-bromo-3-chloropropane is distilled of under vacuum (70° C.). A yellow-orange oil with Rf=0.55 (hexane/ethyl acetate=2:1) is obtained, which is used in the next step without further purification.

B: 2-(3-Chloro-propoxy)-phenylamine 1-(3-Chloro-propoxy)-2-nitro-benzene (~60 mmol) is dissolved in ethanol (200 ml) and platinum dioxide (0.5 g) is added. The stirred mixture is treated with hydrogen under normal pressure until the hydrogen uptake stopped. The catalyst is filtered off and the filtrate is evaporated. A pale yellow oil with Rf=0.3 (CH$_2$Cl$_2$) is obtained, which is used in the next step without further purification.

C: [2-(3-Chloro-propoxy)-phenyl]-(2-chloro-9H-purin-6-yl)-amine 2,6-Dichloropurine (10 mmol) and 2-(3-Chloro-propoxy)-phenylamine (~20 mmol) are dissolved in 1-pentanol and heated up to 70° C. and the mixture is stirred at this temperature for 5 hours. While cooling down to R the product precipitated. The solid material was filtered off and washed with 1-pentanol and diethyl ether. A solid powder with mp. 205° C., Rf=0.42 (CH$_2$Cl$_2$/MeOH=10:1) is obtained.

D: [2-(3-Chloro-propoxy)-phenyl]-(2-chloro-9-cyclopentyl-purin-6-yl)-amine

[2-(3-Chloro-propoxy)-phenyl]-(2-chloro-9H-purin-6-yl)-amine (3 mmol), bromo-cyclopentane (4.1 mmol) and potassium carbonate (water free, 3.6 mmol) are suspended in DMF (20 ml) and heated up to 50° C. and the mixture is stirred at this temperature for 5 hours. After cooling to RT the mixture is poured on water and extracted 3 times with ethyl acetate. The combined organic phases are washed twice with brine and the extract is dried over sodium sulfate and evaporated. The residue is purified by flash chromatography on silica gel with (CH$_2$Cl$_2$/MeOH=20:1) as mobile phase. The product containing fractions are combined and evaporated. The product is cristallized from diethyl ether/pentane, filtered off and dried. A solid powder with mp. 110-112° C., Rf=0.78 (CH$_2$Cl$_2$/MeOH=20:1) is obtained.

E: (2-Chloro-9-cyclopentyl-purin-6-yl)-{2-[3-(4-methyl-piperazin-1-yl)-propoxy]-phenyl}-amine

[2-(3-Chloro-propoxy)-phenyl]-(2-chloro-9-cyclopentyl-purin-6-yl)-amine (0.4 mmol) are stirred at RT in N-methylpiperazine (0.3 ml) for 12 hours. The mixture is diluted with water and extracted 3 times with ethyl acetate. The combined organic phases are washed with brine and the extract is dried over sodium sulfate and evaporated. The residue is purified by flash chromatography on silica gel with (CH$_2$Cl$_2$/MeOH=9:1) as mobile phase. The product containing fractions are combined and evaporated. A pale oil with R=0.25 (CH$_2$Cl$_2$/MeOH=9:2) is obtained.

F: 9-Cyclopentyl-6-{2-[3-(4-methyl-piperazin-1-yl)-propoxy]-phenylamino}-purine-2-carbonitrile (2-Chloro-9-cyclopentyl-purin-6-yl)-{2-[3-(4-methyl-piperazin-1-yl)-propoxy]-phenyl}-amine (0.1 mmol), sodium cyanide (50 mg), potassium iodide (5 mg) are suspended in DMA (2 ml) and heated up to 160° C. and the mixture is stirred at this temperature for 24 hours. The mixture is diluted with water and extracted 3 times with ethyl acetate. The combined organic phases are washed with brine and the extract is dried over sodium sulfate and evaporated.

The residue is dissolved in diethylether, filtered over powdered charcoal and cooled to 4° C. The solid material formed is filtered of and dried (vacuum). A white powder with mp. 136-138° C. is obtained.

$^1$H-NMR (CDCl$_3$): 1.7-2.2 (m, 10H), 2.3 (s, 3H), 2.3-2.4 (m, 2H), 2.4-2.7 (m, 8H), 4.1-4.2 (m, 2H), 4.9-5.0 (m, 1H), 6.9-7.0 (m, 1H), 7.0-7.1 (m, 2H), 8.0 (s, 1H), 8.4 (broad, s, 1H), 8.7 (m, 1H).

Example 10-11

Synthesis of 9-Cyclopentyl-6-{2-[3-(4-methyl-piperazin-1-yl)-propoxy]-phenylamino}-purine-2-carbonitrile A: 1-(3-Chloro-propoxy)-2-nitro-benzene 2-Nitrophenol (70 mmol), 1-bromo-3-chloropropane (360 mmol), potassium carbonate (water free, 110 mmol), potassium iodide (2 mmol) and tetrabutyl-ammonium bromide (1 mmol) are suspended in acetone (130 ml) and heated up to 50° C. and the mixture is then stirred at this temperature for 30 hours. After cooling down to RT the solid material is filtered off and the filtrate is evaporated. The excess of 1-bromo-3-chloropropane is distilled of under vacuum (70° C.). A yellow-orange oil with Rf=0.55 (hexane/ethyl acetate=2:1) is obtained, which is used in the next step without further purification.

B: 2-(3-Chloro-propoxy)-phenylamine 1-(3-Chloro-propoxy)-2-nitro-benzene (~60 mmol) is dissolved in ethanol (200 ml) and platinum dioxide (0.5 g) is added. The stirred mixture is treated with hydrogen under normal pressure until the hydrogen uptake stopped. The catalyst is filtered off and the filtrate is evaporated. A pale yellow oil with Rf=0.3 (CH$_2$Cl$_2$) is obtained, which is used in the next step without further purification.

C: [2-(3-Chloro-propoxy)-phenyl]-(2-chloro-9H-purin-6yl)-amine 2,6-Dichloropurine (10 mmol) and 2-(3-Chloro-propoxy)-phenylamine (~20 mmol) are dissolved in 1-pentanol and heated up to 70° C. and the mixture is stirred at this temperature for 5 hours. While cooling down to R the product precipitated. The solid material was filtered off and washed with 1-pentanol and diethyl ether. A solid powder with mp. 205° C., Rf=0.42 (CH$_2$Cl$_2$/MeOH=10:1) is obtained.

D: [2-(3-Chloro-propoxy)-phenyl]-(2-chloro-9-cyclopentyl-purin-6-yl)-amine

[2-(3-Chloro-propoxy)-phenyl]-(2-chloro-9H-purin-6-yl)-amine (3 mmol), bromo-cyclopentane (4.1 mmol) and potassium carbonate (water free, 3.6 mmol) are suspended in DMF (20 ml) and heated up to 50° C. and the mixture is stirred at this temperature for 5 hours. After cooling to RT the mixture is poured on water and extracted 3 times with ethyl acetate. The combined organic phases are washed twice with brine and the extract is dried over sodium sulfate and evaporated. The residue is purified by flash chromatography on silica gel with (CH$_2$Cl$_2$/MeOH=20:1) as mobile phase. The product containing fractions are combined and evaporated. The product is cristallized from diethyl ether/pentane, filtered off and dried. A solid powder with mp. 110-112° C., Rf=0.78 (CH$_2$Cl$_2$/MeOH=20:1) is obtained.

E: (2-Chloro-9-cyclopentyl-purin-6-yl)-{2-[3-(4-methyl-piperazin-1-yl)-propoxy]-phenyl}-amine

[2-(3-Chloro-propoxy)-phenyl]-(2-chloro-9-cyclopentyl-purin-6-yl)-amine (0.4 mmol) are stirred at RT in N-methylpiperazine (0.3 ml) for 12 hours. The mixture is diluted with water and extracted 3 times with ethyl acetate. The combined organic phases are washed with brine and the extract is dried over sodium sulfate and evaporated. The residue is purified by flash chromatography on silica gel with (CH$_2$Cl$_2$/MeOH=9:1) as mobile phase. The product containing fractions are combined and evaporated. A pale oil with Rf=0.25 (CH$_2$Cl$_2$/MeOH=9:2) is obtained.

F: 9-Cyclopentyl-6-{2-[3-(4-methyl-piperazin-1-yl)-propoxy]-phenylamino}-purine-2-carbonitrile (2-Chloro-9-cyclopentyl-purin-6-yl)-{2-[3-(4-methyl-piperazin-1-yl)-propoxy]-phenyl}-amine (0.1 mmol), sodium cyanide (50 mg), potassium iodide (5 mg) are suspended in DMA (2 ml) and heated up to 160° C. and the mixture is stirred at this temperature for 24 hours. The mixture is diluted with water and extracted 3 times with ethyl acetate. The combined organic phases are washed with brine and the extract is dried over sodium sulfate and evaporated. The residue is dissolved in diethylether, filtered over powdered charcoal and cooled to 4° C. The solid material formed is filtered of and dried (vacuum). A white powder with mp. 136-138° C. is obtained.

$^1$H-NMR (CDCl$_3$): 1.7-2.2 (m, 10H), 2.3 (s, 3H), 2.3-2.4 (m, 2H), 2.4-2.7 (m, 8H), 4.1-4.2 (m, 2H), 4.9-5.0 (m, 1H), 6.9-7.0 (m, 1H), 7.0-7.1 (m, 2H), 8.0 (s, 1H), 8.4 (broad s, 1H), 8.7 (m, 1H).

Example 11 describes the preparation of Quinazoline-carbonitriles

Example 11-1

Synthesis of 4-Cyclopentylamino-6-hydroxy-quinazoline-2-carbonitrile

A: Ethoxy-imino-acetic acid ethyl ester

Nitriloacetic acid ethyl ester (83 mmol) was dissolved in diethyl ether (water free, 25 ml) and ethanol (water free, 85 mmol) was added and the stirred mixture cooled to 40 ° C. At this temperature, HCl (gaz, dried through concentrated sulfuric acid; 18 g total consumption) was bubbled into the solution over 1 hour. The cooling bath was removed and at 0° C. the reaction mixture warmed up quickly (additional cooling required) and the product precipitated. The solid material was filtered off, washed with diethyl ether and dried.

B: 4,6-Dihydroxy-quinazoline-2-carboxylic acid ethyl ester 2-amino-5-hydroxy-benzoic acid (15 mmol) are suspended in ethanol (water free, 600 ml) and heated up to 60° C.

and stirred. Then triethylamine (30 mmol) is added and a clear solution is formed. Ethoxy-imino-acetic acid ethyl ester (1 6.5 mmol) is added at 60° C. and after 15 minutes another portion of triethylamine (15 mmol) is added and the mixture stirred for another 30 minutes. The mixture is cooled down to RT and left at RT without stirring over night. The solid material formed was filtered off, washed with ethanol/ether and dried (vacuum). A pale brown powder with mp. 258-260° C. (decomposition) is obtained.

C: 4,6-Dihydroxy-quinazoline-2-carboxylic acid amide 4,6-Dihydroxy-quinazoline-2-carboxylic acid ethyl ester (11 mmol) is dissolved in methanol (50 ml) containing ammonia (4N). The mixture is stirred for 3 hours and the solid material formed is filtered off. A pale powder with mp. 305° C. (decomposition) is obtained.

D: Acetic acid 2-carbamoyl-4-hydroxy-quinazolin-6-yl ester 4,6-Dihydroxy-quinazoline-2-carboxylic acid amide (12 mmol) are dissolved in warm DMF (20 ml) and triethylamine (13.2 mmol) is added to the stirred mixture. After cooling to RT a solution of acetic acid anhydride in DMF (10 ml) is added dropwise and the mixture is stirred overnight. The solvent is removed and the solid material formed is suspended in ethanol and the solid filtered of and dried (vacuum). A powder with mp. 250° C. is obtained.

E: Acetic acid 4-chloro-2-cyano-quinazolin-6-yl ester

To a mixture of acetic acid 2-carbamoyl-4-hydroxy-quinazolin-6-yl ester 8.1 mmol) and N,N-dimethylanilin (9 mmol) $POCl_3$ (72 mmol) is added and the stirred mixture is heated for 45 minutes at 100° C. The excess of $POCl_3$ is evaporated and the residue is treated with ice/water and extracted fast with ethyl acetate. The organic phase is washed with diluted aqueous HCL-solution (0.1 N), dried over sodium sulfate and evaporated. The residue was dissolved in ethanol and the solid material formed was filtered off and dried (vacuum). A powder with mp. 145-147° C., Rf=0.26 ($CH_2Cl_2$) is obtained.

F: 4-Cyclopentylamino-6-hydroxy-quinazoline-2-carbonitrile

To the stirred suspension of acetic acid 4-chloro-2-cyano-quinazolin-6-yl ester (4.4 mmol) in ethanol (40 ml) cyclopentylamine (3 ml) is added dropwise at RT. After stirring for 30 minutes a clear solution is formed and the mixture is stirred for 2 hours. Then, water (10 ml) is added and the mixture is left over night without stirring. The solvent is removed and the water phase is made basic with 2N NaOH (20 ml). The mixture is extracted with ethyl acetate. The water phase is then acidified with 4N aqueous HCl and extracted with ethyl acetate. The organic phase is dried over sodium sulfate and evaporated. The residue is suspended in $CH_2Cl_2$ and the solid material is filtered off and dried (vacuum). A pale brown, amorphous powder with Rf=0.16 ($CH_2C_2$/MeOH=15:1) is obtained.

$^1$H-NMR (DMSO): 1.5-1.8 (m, 6H), 1.9-2.1 (m, 2H), 4.5 (m, 1H), 7.4 (dd, 1H), 7.6-7.7 (m, 2H), 8.2 (d, 1H), 10.2-10.4 (broad s, 1H).

Example 11-2

Synthesis of 4-Cyclopentylamino-6-(2-dimethylamino-ethoxy)-quinazoline-2-carbonitrile 4-Cyclopentylamino-6-hydroxy-quinazoline-2-carbonitrile (0.4 mmol), (2-Chloro-ethyl)-dimethyl-amine hydrochloride (0.55 mmol) and cesiumcarbonate (3.5 mmol) are stirred in DMF (3 ml) at RT for 20 hours. The suspension is filtered, washed with little DMF and water is added to the filtrate until the solution gets turbid. The precipitate formed is filtered off and dried (vacuum). A white powder with mp. 158-160° C., Rf=0.51 ($CH_2C_2$/MeOH=9:2) is obtained.

$^1$H-NMR (DMSO): 1.5-1.8 (m, 6H), 1.9-2.1 (m, 2H), 2.2 (s, 6H), 2.65 (m, 2H), 4.15 (m, 2H), 4.55 (m, 1H), 7.5 (dd, 1H), 7.7 (d, 1H), 7.8 (m, 1H), 8.3 (broad d, 1H).

Example 11-3

Synthesis of 4-Cyclopentylamino-6-[2-(4-methyl-piperazin-1-yl)-ethoxy]-quinazoline-2-carbonitrile 4-Cyclopentylamino-6-hydroxy-quinazoline-2-carbonitrile (0.4 mmol), 1-(2-Chloro-ethyl)-4-methyl-piperazine dihydrochloride (0.55 mmol) and cesium carbonate (4 mmol) are stirred in DMF (5 ml) at RT for 20 hours. The suspension is filtered, washed with little DMF and water is added to the filtrate until the solution gets turbid. The precipitate formed is filtered off, washed with water and dried (vacuum). A powder with mp. 110-112° C., Rf=0.48 ($CH_2Cl_2$/MeOH=9:2) is obtained.

$^1$H-NMR ($CDCl_3$): 1.5-1.9 (m, 6H), 2.2 (m, 2H), 2.35 (s, 31), 2.4-2.75 (m, 8H), 2.9 (m, 2H), 4.25 (m, 2H), 4.6 (m, 1H), 6.85 (broad d, 1H), 7.05 (d, 1H), 7.45 (dd, 1H), 7.8 (d, 1H).

Example 11-4

4-(2,2-Dimethyl-propylamino)-6-[3-(4-propyl-piperazin-1-yl)-propoxy]-quinazoline-2-carbonitrile A: 4-(2,2-Dimethyl-propylamino)-6-hydroxy-quinazoline-2-carbonitrile To the stirred suspension of acetic acid 4-chloro-2-cyano-quinazolin-6-yl ester (4 mmol) in ethanol (30 ml) 2,2-dimethyl-propylamine (1.4 ml) is added dropwise at RT. The mixture is stirred for 3 hours. Then, water (3 ml) is added and the solvent is evaporated. The residue is dissolved in water and 1N NaOH to ensure basic conditions. The mixture is extracted once with ethyl acetate. The water phase is then acidified with 4N aqueous HCl and extracted with ethyl acetate. The organic phase is dried over sodium sulfate and evaporated. The residue is dissolved in hot ethanol an the solid material formed after cooling is filtered off and dried (vacuum). A powder with Rf=0.13 ($CH_2Cl_2$/MeOH=15:1) is obtained.

B: 4-(2,2-Dimethyl-propylamino)-6-[3-(4-propyl-piperazin-1-yl)-propoxy]-quinazoline-2-carbonitrile 4-(2,2-Dimethyl-propylamino)-6-hydroxy-quinazoline-2-carbonitrile (0.31 mmol), 1-(3-chloro-propyl)4-propyl-piperazine (0.62 mmol) and cesium carbonate (3.1 mmol) are stirred in DMF (3 ml) at RT for 20 hours. Water is added until a clear solution is formed. Then more water is added until the solution gets turbide. The precipitate formed is filtered off, washed with water and dried (vacuum). A powder with mp. 102-104° C., Rf=4 ($CH_2Cl_2$/MeOH=9:2) is obtained.

$^1$H-NMR ($CDCl_3$): 0.9 (t, 3H), 1.05 (s, 9H), 1.4-1.6 (m, 2H), 2.0-2.1 (m, 2H), 2.3 (m, 2H), 2.4-2.6 (m, 8H), 3.55 (m, 2H), 4.15 (m, 2H), 5.85 (broad m, 1H), 6.95 (m, 1H), 7.45 (dd, 1H), 7.8 (d, 1H).

Example 11-5

4-(2,2-Dimethyl-propylamino)-6-{3-[4-(2-methoxy-ethyl)-piperazin-1-yl]-propoxy}-quinazoline-2-carbonitrile 4-(2,2-Dimethyl-propylamino)-6-hydroxy-quinazoline-2-carbonitrile (0.31 mmol), 1-(3-chloro-propyl)-4-propyl-piperazine (0.62 mmol) and cesium carbonate (3.1 mmol) are stirred in DMF (3 ml) at RT for 20 hours. Water is added until a clear solution is formed. Then more water is added until the solution gets turbide. The precipitate formed is filtered off, washed with water and dried (vacuum). A powder with mp. 92-94° C., Rf=0.45 ($CH_2Cl_2$/MeOH=9:2) is obtained.

$^1$H-NMR ($CDCl_3$): 1.05 (s, 9H), 2.0-2.1 (m, 2H), 2.3 (m, 2H), 2.4-2.6 (m, 12H), 3.35 (s, 3H), 3.45-3.6 (m, 4H), 4.15 (m, 2H), 5.75 (broad m, 1H), 6.95 (m, 1H), 7.45 (dd, 1H), 7.8 (d, 1H).

Example 11-6

4-(2,2-Dimethyl-propylamino)-6-[3-(4-isopropyl-piperazin-1-yl)-propoxy]-quinazoline-2-carbonitrile 4-(2,2-Dimethyl-propylamino)-6-hydroxy-quinazoline-2-carbonitrile (0.31 mmol), 1-(3-chloro-propyl)-4-propyl-piperazine (0.62 mmol) and cesium carbonate (3.1 mmol) are stirred in DMF (3 ml) at RT for 20 hours. Water is added until a clear solution is formed. Then more water is added until the solution gets turbide. The precipitate formed is filtered off, washed with water and dried (vacuum). A powder with mp. 103-105° C., Rf=0.4 ($CH_2Cl_2$/MeOH=9:2) is obtained.

$^1$H-NMR ($CDCl_3$): 1.0-1.1 (m, 15H), 2.0-2.1 (m, 2H), 2.4-2.7 (m, 11H), 3.55 (m, 2H), 4.15 (m, 2H), 5.85 (broad m, 1H), 6.95 (m, 1H), 7.45 (dd, 1H), 7.8. (d, 11).

Example 11-7

4-(2,2-Dimethyl-propylamino)-6-(pyridin-4-yl-methoxy)-quinazoline-2-carbonitrile 4-(2,2-Dimethyl-propylamino)-6-hydroxy-quinazoline-2-carbonitrile (0.23 mmol), 4-chloromethyl-pyridine hydrochloride (0.35 mmol) and cesium carbonate (2.3 mmol) are stirred in DMF (3 ml) at RT for 20 hours. Water is added until a clear solution is formed. Then more water is added until the solution gets turbide. The precipitate formed is filtered off, washed with water and dried (vacuum). A powder with mp. 203-205° C., Rf=0.2 ($CH_2Cl_2$/MeOH=15:1) is obtained.

$^1$H-NMR ($CDCl_3$): 1.0 (m, 9H), 3.55 (m, 2H), 5.2 (m, 2H), 5.8 (broad m, 1H), 7.05 (m, 1H), 7.4 (m, 2H), 7.55 (d, 1H), 7.85 (d, 1H), 8.65 (m, 2H).

Example 11-8

4-(2,2-Dimethyl-propylamino)-6-(pyridin-3-yl-methoxy)-quinazoline-2-carbonitrile 4-(2,2-Dimethyl-propylamino)-6-hydroxy-quinazoline-2-carbonitrile (0.25 mmol), 3-chloromethyl-pyridine hydrochloride (0.38 mmol) and cesium carbonate (2.5 mmol) are stirred in DMF (3 ml) at RT for 20 hours. Water is added until a clear solution is formed. Then more water is added until the solution gets turbide. The precipitate formed is filtered off, washed with water and dried (vacuum). A powder with mp. 156-158° C., Rf=0.35 ($CH_2Cl_2$/MeOH=15:1) is obtained.

$^1$H-NMR ($CDCl_3$): 1.0 (m, 9H), 3.55 (m, 2H), 5.2 (m, 2H), 5.8 (broad m, 1H), 7.05 (m, 1H), 7.35 (m, 1H), 7.55 (m, 1H), 7.8-7.9 (m, 2H). 8.65 (m, 1H), 8.75 (m, 1H).

Example 11-9

4-(2,2-Dimethyl-propylamino)-6-(pyridin-2-yl-methoxy)-quinazoline-2-carbonitrile 4-(2,2-Dimethyl-propylamino)-6-hydroxy-quinazoline-2-carbonitrile (0.23 mmol), 2-chloromethyl-pyridine hydrochloride (0.35 mmol) and cesium carbonate (2.3 mmol) are stirred in DMF (3 ml) at RT for 20 hours. Water is added until a clear solution is formed. Then more water is added until the solution gets turbide. The precipitate formed is filtered off, washed with water and dried (vacuum). A powder with mp. 160° C., R=0.4 ($CH_2Cl_2$/MeOH=15:1) is obtained.

$^1$H-NMR ($CDCl_3$): 1.0 (m, 9H), 3.55 (m, 2H), 5.35 (m, 2H), 6.05 (broad m, 1H), 7.2-7.3 (m, 2H), 7.45-7.6 (m, 2H), 7.7-7.85 (m, 2H), 8.6 (m, 1H).

Example 11-10

4-(2,2-Dimethyl-propylamino)-6-(1-methyl-piperidin-2-ylmethoxy)-quinazoline-2-carbonitrile 4-(2,2-Dimethyl-propylamino)-6-hydroxy-quinazoline-2-carbonitrile (0.3 1 mmol), 1-methyl-2-chloromethyl-piperidine hydrochloride (0.41 mmol) and potassium carbonate (7.2 mmol) are stirred in DMF (3 ml) at 80° C. for 8 hours. The solvent is evaporated, the residue is dissolved in water and extracted with ethyl acetate. The organic phase is dried over sodium sulfate and evaporated. The residue is purified by flash chromatography on silica gel with ($CH_2Cl_2$/MeOH=9:1) as mobile phase. The product containing fractions are combined and evaporated. A pale oil with Rf=0.54 ($CH_2Cl_2$/MeOH=10:1) is obtained.

$^1$H-NMR ($CDCl_3$): 1.05 (m, 9H), 1.3-1.45 (m, 1H), 1.6-1.9 (m, 5H), 2.2 (m,1H), 2.35 (m, 1H), 2.4 (s, 3H), 2.9-3.0 (m, 1H) 3.55 (m, 2H), 4.1-4.25 (m, 2H), 5.8 (broad m, 1H), 7.05 (m, 1H), 7.5 (dd, 1H), 7.85 (d, 1H).

The following compounds of formula 11-1, as identified in Table 11-1 below are prepared Analogously to the above examples, starting from the corresponding substituted 4-amino-6-hydroxy-quinazoline-2-carbonitrile.

TABLE 11-1
| Ex. No | R1 (* indicates the bond to the nitrogen) | R2 (* indicates the bond to the oxygen) | RF-value (mobile phase) | Melting point or molecular weight by MS. |
|---|---|---|---|---|
| 11-11 | 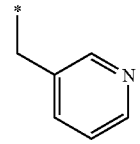 |  | 0.1 (CH$_2$Cl$_2$/MeOH = 15:1) | 144-146° C. |
| 11-12 | 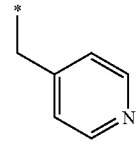 |  | 0.29 (CH$_2$Cl$_2$/MeOH = 15:1) | 212-214° C. |
| 11-13 | 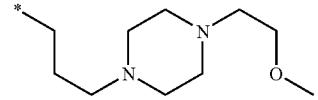 |  | 0.5 (CH$_2$Cl$_2$/MeOH = 9:2) | M$^+$ = 439.3 |
| 11-14 | 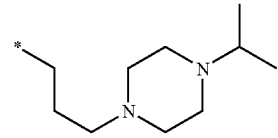 |  | 0.42 (CH$_2$Cl$_2$/MeOH = 9:2) | 155° C. |
| 11-15 | 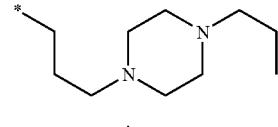 |  | 0.6 (CH$_2$Cl$_2$/MeOH = 9:2) | 145-148° C. |
| 11-16 | 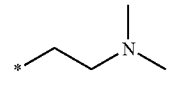 |  | 0.4 (CH$_2$Cl$_2$/MeOH = 9:2) | 118-120° C. |
| 11-17 | 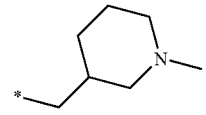 |  | 0.18 (CH$_2$Cl$_2$/MeOH = 9:2) | M$^+$ = 368.3 |
| 11-18 | 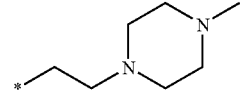 |  | 0.3 (CH$_2$Cl$_2$/MeOH = 9:2) | 105-107° C. |
| 11-19 | 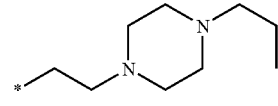 |  | 0.45 (CH$_2$Cl$_2$/MeOH = 9:2) | 65-67° C. |
| 11-20 | 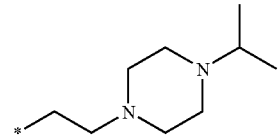 |  | 0.25 (CH$_2$Cl$_2$/MeOH = 9:2) | 70-72° C. |

TABLE 11-1-continued 11-1

| Ex. No | R1 (* indicates the bond to the nitrogen) | R2 (* indicates the bond to the oxygen) | RF-value (mobile phase) | Melting point or molecular weight by MS. |
|---|---|---|---|---|
| 11-21 | neopentyl * | piperazine-ethyl-OMe * | 0.65 (CH$_2$Cl$_2$/MeOH = 9:2) | 95° C. |
| 11-22 | isobutyl * | piperazine-ethyl-OMe * | 0.74 (CH$_2$Cl$_2$/MeOH = 9:2) | 100° C. |
| 11-23 | isobutyl * | 4-methylpiperazine-ethyl * | 0.35 (CH$_2$Cl$_2$/MeOH = 9:2) | 95-97° C. |
| 11-24 | isobutyl * | dimethylamino-ethyl * | 0.4 (CH$_2$Cl$_2$/MeOH = 9:2) | 133-135° C. |

Example 12 describes the preparation of 5-substituted -pyrimidine-2-carbonitriles Example 12-1

4-Cyclopentylamino-5-(4-phenyl-but-1-ynyl)-pyrimidine-2-carbonitrile

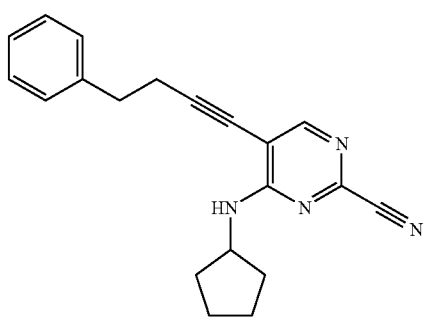

5-Bromo-4-cyclopentylamino-pyrimidine-2-carbonitrile (0.69 mmol), 4-phenyl-1-butyne (1.66 mmol), dichlorobis (triphenylphosphine)palladium(II) (0.035 mmol), copper (I) iodide (0.07 mmol) and triethylamine (2.1 mmol) in DMF (5 ml) is stirred at 75° C. for 2.5 h. The reaction mixture is treated with saturated ammonium chloride and extracted with AcOEt. The organic layer is washed with brine, dried over magnesium sulfate and evaporated down. The crude product is applied to a silica gel column chromatography, which is eluted with following solvents: n-hexane:AcOEt=12:1 (v/v) and n-hexane:AcOEt=10:1 (v/v). The solvent of the latter effluent is removed by evaporation and dried in vacuo to afford the title compound. yield 89.9%, Rf=0.65 (n-hexane: AcOEt=2:1).

$^1$H-NMR (400 MHz, CDCl$_3$) δ 1.26-1.33(m, 2H), 1.64-1.71(m, 4H), 2.05-2.09(m, 3H), 2.79-2.86(m, 2H), 2.94-3.00 (m, 2H), 4.30-4.38(m, 2H), 5.36-534(m, 1H), 7.35-7.21(m, 5H), 8.10(s, 1H), 12-2

4-(2,2-Dimethyl-propylamino)-5-{3-[4-(4-methyl-piperazin-1-yl)-phenyl]-prop-1-ynyl}-pyrimidine-2-carbonitrile

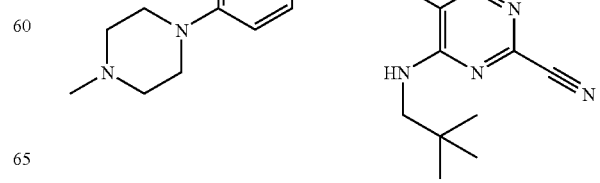

A. 1-[4-(4-Methyl-piperazin-1-yl)-phenyl]-prop-2-yn-1-ol

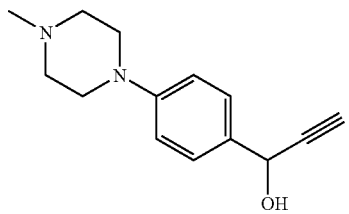

To a solution of 4-(4-methyl-piperazin-1-yl)-benzaldehyde (28.9 mmol) in THF (100 ml), ethnylmagnesium bromide (0.5M solution in THF) (43.4 mmol) is added at −78° C. The solution is then stirred at room temperature for 18 h. The reaction mixture is treated with saturated ammonium chloride and extracted with ethyl acetate. The organic layer is washed with brine, dried over magnesium sulfate and evaporated down. $CH_2Cl_2$ is added to the residue to afford a precipitate, which is collected by filtration. yield 84.2%, Rf=0.23 ($CH_2Cl_2$:MeOH=9:1).

B. 1-Methyl4-(4-prop-2-ynyl-phenyl)-piperazine

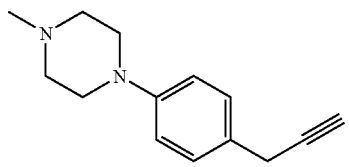

To a stirred mixture of glacial acetic acid (72 ml) and trifluoroacetic acid (8 ml), $NaBH_4$ (79.1 mmol) is added slowly under nitrogen at −15° C. The solution of 1-[4-(4-methyl-piperazin-1-yl)-phenyl]-prop-2-yn-1-ol (1 1.3 mmol) in $CH_2Cl_2$ (80 ml) is added dropwise over 0.5 h and the mixture is stirred at room temperature for 1 h. The solvents are removed under reduced pressure and the residue is added to saturated sodium bicarbonate. The aqueous solution is extracted with $CH_2Cl_2$. The organic layer is washed with brine, dried over magnesium sulfate and evaporated down. The crude product is applied to silica gel column chromatography, which is eluted with following solvents: $CH_2Cl_2$ and 5% MeOH in $CH_2Cl_2$. The solvent of the latter effluent is removed by evaporation and dried in vacuo to afford the title compound. yield 86.8%, Rf=0.52 ($CH_2Cl_2$:MeOH=9:1).

C. 4-(2,2-Dimethyl-propylamino)-5-{3-[4-(4-methyl-piperazin-1-yl)-phenyl]-prop-1-ynyl}-pyrimidine-2-carbonitrile

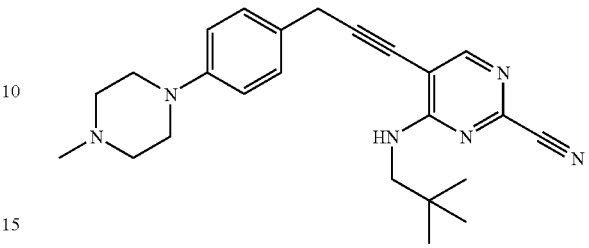

To a solution of 1-methyl-4-(4-prop-2-ynyl-phenyl)-piperazine (0.75 mmol) and 5-bromo-4-(2,2-dimethyl-propylamino)-pyrimidine-2-carbonitrile (0.5 mmol) in THF (7 ml), triethylamine (1.5 mmol), dichlorobis(triphenylphosphine) palladium (II) (0.025 mmol) and copper (I) iodide (0.05 mmol) are added. The reaction mixture is heated at 60° C. ca. for 3 h. Saturated aqueous solution of ammonium chloride is added to the reaction mixture and then aqueous layer is extracted with two 50 ml portions of AcOEt. The combined extracts are washed with brine, dried over sodium sulfate and concentrated under vacuum to give crude product which is purified by reverse phase HPLC. Yield: 25%. Rf=0.5 (MeOH:$CH_2Cl_2$=5:95)

$^1$H NMR(400 MHz, $CDCl_3$) δ 0.91(s, 9H), 2.38(s, 3H), 2.61 (m, 4H), 3.21(t, 4H), 3.32(d, 2H), 3.83(s, 2H), 5.75(s, 1H), 6.91(d, 2H), 7.24(d, 2H), 8.19(s, 1H)

The preparation of starting materials.

2-Prop-2-ynyl-1,2,3,4-tetrahydro-isoquinoline

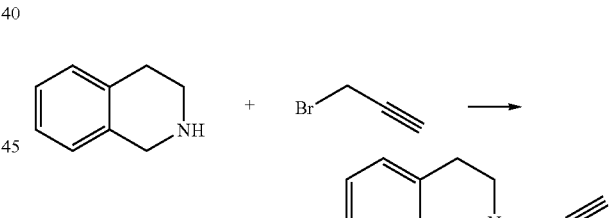

To 1,2,3,4-tetrahydro-isoquinoline (9.4 mmol) in DMF (10 ml), 3-bromo-propyne (4.5 mmol) is added at 0° C. and stirred at room temperature for 18 h. After the reaction mixture is treated with saturated ammonium chloride, the mixture is extracted with AcOEt. The organic layer is washed with brine, dried over magnesium sulfate and evaporated down. The crude product is applied to a silica gel column chromatography, which is eluted with following solvents: n-hexane and n-hexane:AcOEt=1:1 (v/v). The solvent of the latter effluent is removed by evaporation and dried in vacuo to afford the title compound. yield 91.2%, Rf=0.67 (n-hexane:AcOEt=1:5).

By repeating the procedures described immediately above using appropriate starting materials and conditions the following compounds of formula 12-1 are obtained as identified below in Table 12-1.

TABLE 12-1

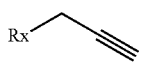

12-1

| Rx | Yield (%) | Rf (Solvent) | ¹H-NMR(400 MHz, δ) |
|---|---|---|---|
| 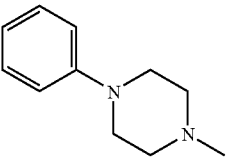 | 10.0 | 0.67 (CH$_2$Cl$_2$:MeOH = 9:1) | (CDCl$_3$): 2.28(t, 1H), 2.73-2.76(m, 4H), 3.23-3.26(m, 4H), 3.37(d, 2H), 6.86(t, 1H), 6.93(d, 2H), 7.24-7.31(m, 2H), |
| 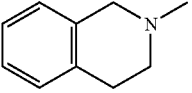 | 91.2 | 0.67 (n-hexane:AcOEt = 1:5) | (CDCl$_3$): 2.27(t, 1H), 2.83-2.86(m, 4H), 2.91-2.95(m, 4H), 3.51(d, 2H), 3.77(s, 2H), 7.05-7.13(m, 4H), |
| 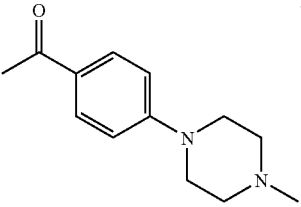 | 73.7 | 0.37 (CH$_2$Cl$_2$:MeOH = 9:1) | (CDCl$_3$): 2.28(t, 1H), 2.52(s, 3H), 2.66-2.68(m, 4H), 3.37-3.44(m, 6H), 6.86(d, 2H), 7.86(d, 2H), |
| 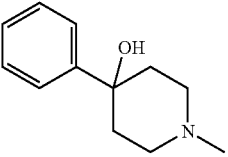 | 65.3 | 0.32 (n-hexane:AcOEt = 1:5) | (CDCl$_3$): 1.78-1.82(m, 2H), 2.17-2.24(m, 2H), 2.28(t, 1H), 2.67-2.73(m, 2H), 2.82-2.85(m, 2H), 3.36(d, 2H), 2.25-2.29(m, 1H), 7.38(t, 2H), 7.50(d, 2H), |
| 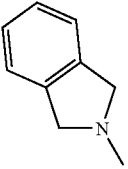 | 87.9 | 0.41 (n-hexane:AcOEt = 1:1) | (CDCl$_3$): 2.29(t, 1H), 3.64(d, 2H), 4.07(s, 4H), 7.21(s, 4H), |

12-3

5-[3-(3,4-Dihydro-1H-isoquinolin-2-yl)-prop-1-ynyl]-4-(2,2-dimethyl-propylamino)-pyrimidine-2-carbonitrile

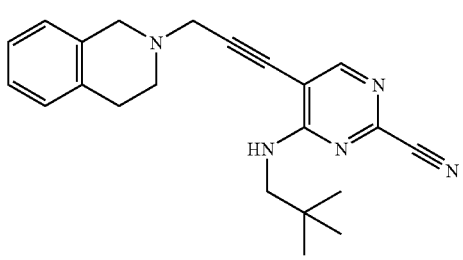

2-Prop-2-ynyl-1,2,3,4-tetrahydro-isoquinoline (0.72 mmol), 5-bromo-4-(2,2-dimethyl-propylamino)-pyrimidine-2-carbonitrile (0.86 mmol), Bis(benzonitrile)-palladium(II) chloride (0.02 mmol), copper (I) iodide (0.015 mmol), tri-tert-butylphosphine (0.04 mmol) and diisopropyl amine (0.86 mmol) in dioxane (4 ml) is stirred at room temperature for 2.5 h. After filtration, the reaction mixture is treated with saturated ammonium chloride. The mixture is extracted with AcOEt. The organic layer is washed with brine, dried over magnesium sulfate and evaporated down. The crude product is applied to a column of silica gel, which is eluted with following solvents: n-hexane:AcOEt=1:1 (v/v) and n-hexane:AcOEt=1:5 (v/v). The solvent of the latter effluent is removed by evaporation and dried in vacuo to afford the title compound. yield 46.5%, Rf=0.31 (n-hexane:AcOEt=1:1).

By repeating the procedures described above using appropriate starting materials and conditions the following compounds of formula 12-2 are obtained as identified below in Table 12-2.

TABLE 12-2

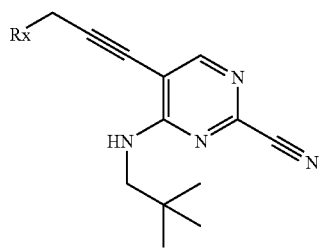

| Expl. No. | Rx | Yield (%) | Rf (Solvent) | $^1$H-NMR (400 MHz, δ) |
|---|---|---|---|---|
| 12-4 | 1-methyl-4-phenylpiperazine | 41.0 | 0.43 (CH$_2$Cl$_2$:MeOH = 9:1) | (CDCl$_3$): 0.97(s, 9H), 2.78-2.81(m, 4H), 3.25-3.27(m, 4H), 3.37(d, 2H), 3.69(s, 2H), 5.84(br, 1H), 6.87-6.94(m, 3H), 7.26-7.30(m, 2H), 8.22(s, 1H), |
| 12-3 | 2-methyl-1,2,3,4-tetrahydroisoquinoline | 46.5 | 0.31 (n-hexane:AcOEt = 1:1) | (CDCl$_3$): 0.95(s, 9H), 2.88-2.99(m, 4H), 3.36(d, 2H), 3.76(s, 4H), 5.84(br, 1H), 7.00-7.04(m, 1H), 7.12-7.18(m, 3H), 8.21(s, 1H), |
| 12-5 | 1-(4-(4-methylpiperazin-1-yl)phenyl)ethanone | 63.0 | 0.21 (n-hexane:AcOEt = 1:5) | (CDCl$_3$): 0.97(s, 9H), 2.53(s, 3H), 2.76-2.79(m, 4H), 3.36-3.43(m, 6H), 3.70(s, 2H), 5.79(br, 1H), 6.87(d, 2H), 7.88(d, 2H), 8.22(s, 1H), |
| 12-6 | 1-methyl-4-phenylpiperidin-4-ol | 26.1 | 0.28 (n-hexane:AcOEt = 1:5) | (CDCl$_3$): 0.98(s, 9H), 1.46(s, 1H), 1.81-1.85(m, 2H), 2.17-2.25(m, 2H), 2.75-2.89(m, 4H), 3.38(d, 2H), 3.68(s, 2H), 5.89(br, 1H), 7.26-7.30(m, 1H), 7.38(t, 2H), 7.50(d, 2H), 8.22(s, 1H), |
| 12-7 | 2-methylisoindoline | 65.1 | 0.32 (n-hexane:AcOEt = 1:5) | (CDCl$_3$): 0.91(s, 9H), 3.33(d, 2H), 3.95(s, 2H), 4.13(s, 4H), 5.78(br, 1H), 7.22(s, 4H), 8.13(s, 1H), |

12-8

4-(2,2-Dimethyl-propylamino)-5-[3-(4-pyridin-2-yl-piperazin-1-yl)-prop-1-ynyl]-pyrimidine-2-carbonitrile

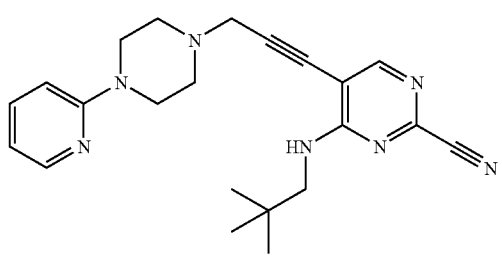

1-(2-Propynyl)-4-(2-pyridinyl)-piperazine (prepared from 1-(2-pyridinyl)-piperazine and propargyl bromide) (1.5 mmol) is dissolved in DMF at room temperature under nitrogen atmosphere. To the solution, 5-bromo-4-(2,2-dimethyl-propylamino)-pyrimidine-2-carbonitrile (1 mmol), triethylamine (3 mmol), copper(I) iodide (0.1 mmol), and dichlorobis(triphenylphosphine)palladium(II) (0.05 mmol) are added successively. The mixture is heated at 80° C. under nitrogen atmosphere for 3 h. After cooling at room temperature, the mixture is diluted with H$_2$O and extracted with AcOEt. The organic layer is dried over magnesium sulfate and evaporated in vacuo. The residue is purified by silica gel column chromatography (n-hexane:AcOEt=1:5) to give 4-(2,2-dimethyl-propylamino)-5-[3-(4-pyridin-2-yl-piperazin-1-yl)-prop-1-ynyl]-pyrimidine-2-carbonitrile. Yield 97%. Rf=0.30 (n-hexane:AcOEt=1:5). $^1$H NMR (400 MHz, CDCl$_3$) δ 0.95(s, 9H), 2.75-2.73(m, 4H), 3.36(d, 2H), 3.63-3.60(m, 4H), 3.69(s, 2H), 5.78(brs, 1H), 6.63-6.67(m, 2H), 7.47-7.52(m, 1H), 8.19-8.21(m, 2H).

By repeating the procedure described above using appropriate starting materials and conditions, the following compounds of Formula 12-3 are obtained as identified below in Table 12-3.

TABLE 12-3

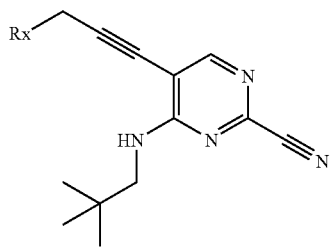

12-3

| Expl. No. | Rx | Yield (%) | Rf (Solvent) | $^1$H NMR(400 MHz, δ) |
|---|---|---|---|---|
| 12-9 | | 17 | 0.45 (n-hexane:AcOEt = 1:1) | 0.82(s, 9H), 3.30(d, 2H), 4.42(s, 2H), 4.55(s, 2H), 6.50(brs, 1H), 7.44(d, 1H), 7.57(t, 1H), 7.64-7.68(m, 1H), 7.81(d, 1H), 8.14(s, 1H) |
| 12-10 | | 10 | 0.47 (n-hexane:AcOEt = 1:1) | (CDCl$_3$): 1.12(s, 9H), 4.17(s, 2H), 5.64(s, 2H), 6.18(s, 1H), 7.23(d, 1H), 7.29-7.37(m, 2H), 7.89(d, 1H), 7.95(s, 1H), 8.85(s, 1H) |
| 12-11 | | 72 | 0.26 (AcOEt) | (CDCl$_3$): 0.89(s, 9H), 3.32(d, 2H), 5.06(s, 2H), 5.64(brs, 1H), 7.27-7.34(m, 1H), 8.22(s, 1H), 8.31(brd, 1H), 8.42(brd, 1H) |
| 12-12 | | 44 | 0.34 (CH$_2$Cl$_2$:MeOH = 95:5) | (CDCl$_3$): 1.16-1.29(m, 2H), 1.38-1.50(m, 2H), 1.64-1.79(m, 3H), 1.94-2.04(m, 2H), 3.96-4.08(m, 1H), 5.07(s, 2H), 5.32-5.41(m, 1H), 7.09(bs, 1H), 7.17(bs, 1H), 7.64(bs, 1H), 8.23(s, 1H) |
| 12-13 | | 57 | 0.49 (n-hexane:AcOEt = 1:1) | (CDCl$_3$): 0.95(s, 9H), 3.37(d, 2H), 5.01(s, 2H), 5.63(bs, 1H), 7.55(s, 1H), 8.24(s, 1H) |

12-14

4-Cyclohexylamino-5-{3-[4-(4-methyl-piperazin-1-ylmethyl)-phenoxy]-prop-1-ynyl}-pyrimidine-2-carbonitrile

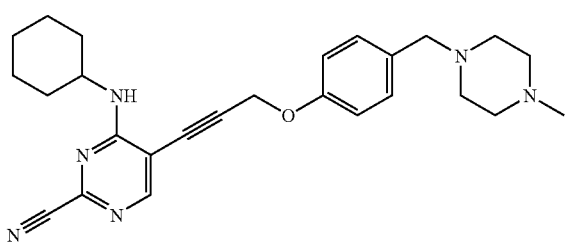

A. 5-[3-(4-Chloromethyl-phenoxy)-prop-1-ynyl]-4-cyclohexylamino-pyrimidine-2-carbonitrile

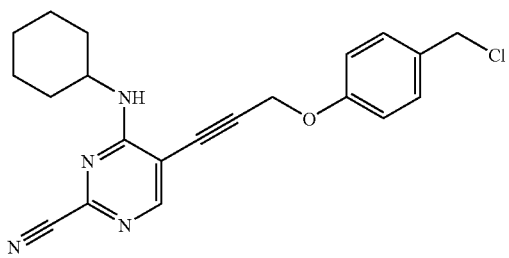

5-Bromo-4-cyclohexylamino-pyrimidine-2-carbonitrile (0.19 mmol) and chloromethyl-4-prop-2-ynyloxy-benzene (0.22 mmol) in DMF (5 ml) are treated with triethylamine (0.56 mmol), copper (I) iodide (0.019 mmol), and dichlorobis(triphenylphosphine)palladium(II) (0.0093 mmol) at room temperature. The mixture is stirred for 2 h at 65° C., poured into an ice water, extracted with AcOEt. The organic layer is washed with brine, dried over magnesium sulfate and concentrated. The crude product is purified by silica gel column chromatography to give the product in 21% yield. Rf=0.75 (n-hexanes:AcOEt=1:2). $^1$H-NMR (400 MHz, CDCl$_3$) δ 1.02-1.48 (m, 5H), 1.57-1.78 (m, 3H), 1.80-1.98 (m, 2H), 3.94-4.04 (m, 1H), 4.61(s, 2H), 5.03 (s, 2H), 5.38 (d, 1H), 7.04 (d, 2H), 7.41 (d, 2H), 8.21 (s, 1H).

B. 4-Cyclohexylamino-5-{3-[4-(4-methyl-piperazin-1-ylmethyl)-phenoxy]-prop-1-ynyl}-pyrimidine-2-carbonitrile

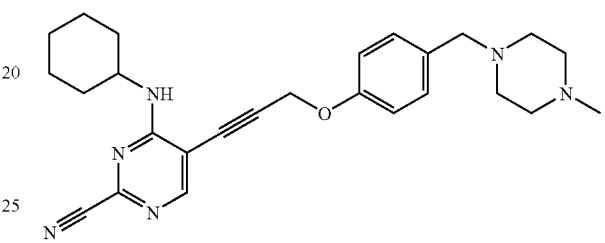

5-[3-(4-Chloromethyl-phenoxy)-prop-1-ynyl]4-cyclohexylamino-pyrimidine-2-carbonitrile (0.050 mmol) is dissolved in CH$_2$Cl$_2$ (2 ml) and 1-methyl-piperazine (0.10 mmol) is added at room temperature and the mixture is stirred at room temperature for overnight. Water is added and the organic layer is washed with brine, dried over magnesium sulfate and concentrated. The crude product is purified by silica gel column chromatography to give the product in 40% yield.

By repeating the procedures described in the above example using appropriate starting materials and conditions the following compounds of formula 12-4 are obtained as identified below in Table 12-4.

TABLE 12-4

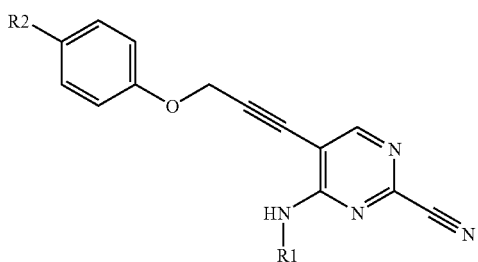

| Expl. Nos. | R1 | R2 | Yield (%) | Rf (Solvent) | $^1$H-NMR (400 MHz, δ) |
|---|---|---|---|---|---|
| 12-15 | cyclohexyl | N-ethyl-piperazinylmethyl | 40 | 0.60 (CH$_2$Cl$_2$:MeOH = 5:1) | (CDCl$_3$): 1.02-1.43(m, 5H), 1.61-1.75(m, 3H), 1.86-1.98(m, 2H), 2.28(s, 3H), 2.54(brs, 8H), 3.46(s, 2H), 3.89-4.01(m, 1H), 4.97(s, 2H), 5.38(d, 1H), 6.89(d, 2H), 7.28(d, 2H), 8.19(s, 1H). |

TABLE 12-4-continued 12-4

| Expl. Nos. | R1 | R2 | Yield (%) | Rf (Solvent) | $^1$H-NMR (400 MHz, δ) |
|---|---|---|---|---|---|
| 12-16 | (cyclohexylmethyl) | (4-ethyl-1,4-diazepan-1-yl)methyl | 24 | 0.57 (CH$_2$Cl$_2$:MeOH = 5:1) | (CDCl$_3$): 0.99-1.46(m, 6H), 1.75-1.95(m, 4H), 2.38(s, 3H), 2.56-2.74(m, 6H), 3.59(s, 2H), 3.89-4.01(m, 1H), 4.97(s, 2H), 5.38(d, 1H), 6.98(d, 2H), 7.30(d, 2H), 8.19(s, 1H). |
| 12-17 | (2,2-dimethylpropyl variant) | (4-ethylpiperazin-1-yl)methyl | 82 | 0.58 (CH$_2$Cl$_2$:MeOH = 5:1) | (CDCl$_3$): 0.89(s, 9H), 2.35(s, 3H), 2.47(brs, 8H), 3.29(s, 2H), 3.51(s, 2H), 5.03(s, 2H), 5.68(brt, 1H), 7.00(d, 2H), 7.32(d, 2H), 8.25(s, 1H). |

12-18

4-(2,2-Dimethyl-propylamino)-5-[3-oxo-3-(4-[1,2,3] triazol-1-yl-phenyl)-prop-1-ynyl]-pyrimidine-2-carbonitrile

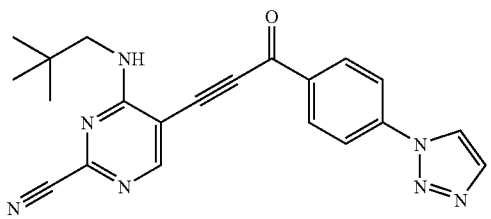

A. 4-(2,2-Dimethyl-propylamino)-5-ethynyl-pyrimidine-2-carbonitrile

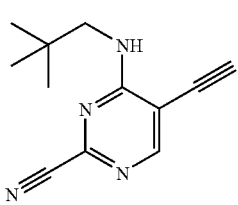

5-Bromo-4-(2,2-dimethyl-propylamino)-pyrimidine-2-carbonitrile (7.58 mmol) and ethynyl-trimethyl-silane (22.74 mmol) in DMF (20 ml) are treated with triethylamine (38.0 mmol), copper (I) iodide (0.76 mmol), and dichlorobis(triphenylphosphine)palladium(II) (0.38 mmol) at room temperature. The mixture is stirred for 1.5 h at room temperature, poured into an ice water and extracted with AcOEt. The organic layer is washed with brine, dried over magnesium sulfate and concentrated. The crude product is dissolved in methanol (60 ml)—water (10 ml) and cesium fluoride (4.2 mmol) is added at room temperature and the mixture is stirred at room temperature for 5 min. The reaction mixture is evaporated, then water and CH$_2$Cl$_2$ are added. The organic layer is washed with brine, dried over magnesium sulfate and concentrated. The crude product is purified by silica gel column chromatography to give the product in 76% yield. Rf=0.67 (n-hexane:AcOEt=2:1)

$^1$H-NMR (400 MHz, CDCl$_3$) δ 1.00 (s, 9H), 3.50 (d, 2H), 3.57 (s, 1H), 5.79 (brt, 1H). 8.25 (s, 1H).

B. 4-(2,2-Dimethyl-propylamino)-5-[3-oxo-3-(4-[1,2,3]triazol-1-yl-phenyl)-prop-1-ynyl]-pyrimidine-2-carbonitrile

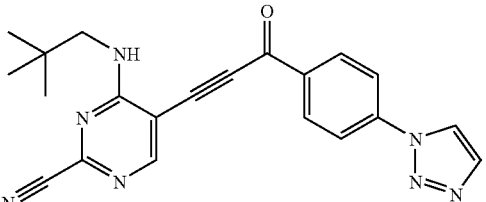

4-[1,2,3]Triazol-1-yl-benzoic acid (5.0 mmol) is dissolved in CH$_2$Cl$_2$ (20 ml). Oxalyl chloride (3.5 mmol) and DMF (1 drop) are added at room temperature and the reaction mixture is stirred at room temperature for 3 h, then evaporated. The residue is dissolved in CH$_2$C$_2$ (20 ml) and the mixture is added to 4-(2,2-dimethyl-propylamino)-5-ethynyl-pyrimidine-2-carbonitrile, copper (I) iodide (0.13 mmol) and triethylamine (13.0 mmol) at room temperature. The reaction mixture is stirred for overnight at room temperature. The organic layer is washed with brine, dried over magnesium sulfate and concentrated. The crude product is purified by silica gel column chromatography to give the product in 31% yield. Rf=0.02 (n-hexane:AcOEt=2:1)

$^1$H-NMR (400 MHz, CDCl$_3$) δ 1.03 (s, 9H), 3.40 (d, 2H), 6.09 (brt, 1H), 7.92 (d, 1H), 8.01 (d, 2H), 8.16 (d, 1H), 8.33 (d, 2H), 8.49 (s, 1H).

12-19

5-{3-[4-(3-Chloro-propane-1-sulfonyl)-piperazin-1-yl]-prop-1-ynyl}-4-(2,2-dimethyl-propylamino)-pyrimidine-2-carbonitrile

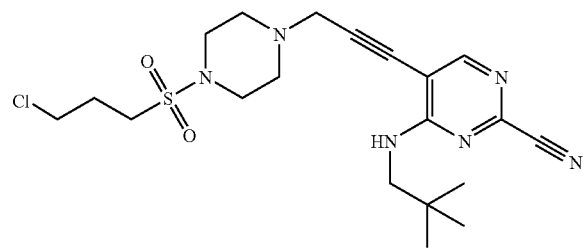

A. 4-{3-[2-Cyano-4-(2,2-dimethyl-propylamino)-pyrimidin-5-yl]-prop-2-ynyl}-piperazine-1-carboxylic acid .tert.-butyl ester

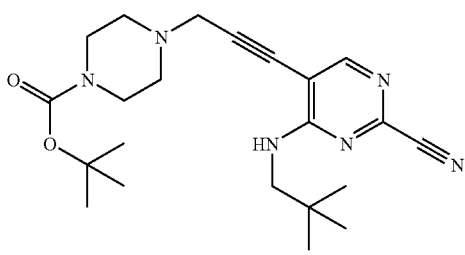

To a solution of 4-prop-2-ynyl-piperazine-1-carboxylic acid tert.-butyl ester (1.5 mmol) and 5-bromo-4-(2,2-dimethyl-propylamino)-pyrimidine-2-carbonitrile (1 mmol) in DMF (6 ml), triethylamine (3.0 mmol), dichlorobis(triphenylphosphine)palladium(II) (0.1 mmol) and copper (I) iodide (0.2 mmol) are added. The reaction mixture is heated at 85° C. ca. for 1 day. The mixture is quenched with ammonium chloride and extracted with AcOEt. The combined extracts are washed with brine, dried over sodium sulfate and concentrated under vacuum to give 402 mg of crude product, which is purified by silica gel column chromatography to afford the title compound. Yield: 85%. Rf=0.3 (AcOEt only)

$^1$H NMR(400 MHz, CDCl$_3$) δ 0.98(s, 9H), 1.46(s, 9H), 2.56 (t, 4H), 3.37(d, 2H), 3.49(t, 4H), 3.64(s, 2H), 5.74-5.84 (m, 1H), 8.20(s, 1H)

B. 4-(2,2-Dimethyl-propylamino)-5-(3-piperazin-1-yl-prop-1-ynyl)-pyrimidine-2-carbonitrile

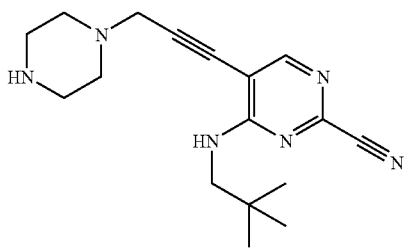

To a solution of 4-{3-[2-cyano-4-(2,2-dimethyl-propylamino)-pyrimidin-5-yl]-prop-2-ynyl}-piperazine-1-carboxylic acid .tert.-butyl ester (2.9 mmol) in dioxane (5 ml), 4N hydrogenchloride in dioxane(15 ml) is added at 0° C. The reaction mixture is stirred at room temperature for 1 day and then evaporated under reduced pressure. To a solution of residual solid, CH$_2$Cl$_2$ is added at room temperature, pH is adjusted to 9.0 by triethylamine. The mixture is quenched with ammonium chloride and extracted with CH$_2$Cl$_2$. The combined extracts are washed with brine, dried over sodium sulfate and concentrated under vacuum. The residue is purified by silica gel column chromatography to afford title compound in 72% yield. Rf=0.11 (MeOH:CH$_2$C$_2$=1:9)

$^1$H NMR(400 MHz, CDCl$_3$) δ 0.98(s, 9H), 2.6-2.7(m, 4H), 2.9-3.0 (m, 4H), 3.38(d, 2H), 3.62(s, 2H), 5.75-5.82(m, 1H), 8.22(s, 1H)

C. 5-{3-[4-(3-Chloro-propane-1-sulfonyl)-piperazin-1-yl]-prop-1-ynyl}-4-(2,2-dimethyl-propylamino)-pyrimidine-2-carbonitrile

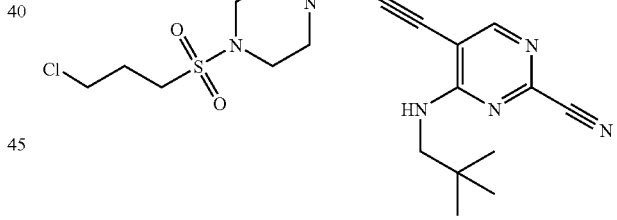

To a solution of 4-(2,2-dimethyl-propylamino)-5-(3-piperazin-1-yl-prop-1-ynyl)-pyrimidine-2-carbonitrile (0.16 mmol) in CH$_2$Cl$_2$ (5 ml), 3-chloropropanesulfonyl chloride (0.192 mmol) and triethylamine (0.192 mmol) are added at 0° C. The reaction mixture is stirred at room temperature for 14 h and then saturated aqueous solution of ammonium chloride is added to the reaction mixture. The mixture is extracted with two 50 ml portions of AcOEt. The combined extracts are washed with brine, dried over sodium sulfate and concentrated under vacuum. The purification of the residue by silica gel column chromatography affords 37 mg of title compound in 51% yield. Rf=0.33(AcOEt only)

$^1$H NMR(400 MHz CDCl$_3$) δ 0.98(s, 9H), 2.25-2.35(m, 2H), 2.71 (t, 4H), 3.10(t, 3H), 2H), 3.68(s, 2H), 3.69(t, 3H), 5.75(m, 1H), 8.22(s, 1H)

By repeating the procedures described in the above example using appropriate starting materials and conditions the following compounds of formula 12-5 are obtained as identified below in Table 2-5.

TABLE 12-5

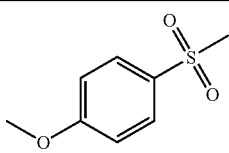

12-5

| Expl. No. | R | Yield (%) | Rf (Solvent) | ¹H NMR(400 MHz, δ) |
|---|---|---|---|---|
| 12-20 | 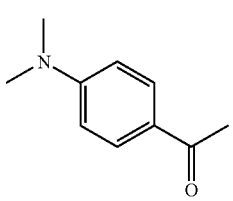 | 31 | 0.60 (AcOEt only) | (CDCl$_3$): 0.97(s, 9H), 2.70(t, 4H), 3.04-3.12(m, 4H), 3.37(d, 2H), 3.60(s, 2H), 3.87(s, 3H), 5.70-5.78(m, 1H), 7.00(d, 2H), 7.70(d, 2H), 8.19(s, 1H) |
| 12-21 | 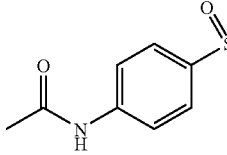 | 71 | 0.67 (MeOH:CH$_2$Cl$_2$ = 1:19) | (CDCl$_3$): 0.97(s, 9H), 2.62(t, 4H), 3.00(s, 6H), 3.38(d, 2H), 3.66(s, 2H), 3.69-3.75(m, 4H), 5.75-5.81(m, 1H), 6.67(d, 2H), 7.35(d, 2H), 8.21(s, 1H) |
| 12-22 | 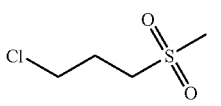 | 79 | 0.16 (AcOEt only) | (CDCl$_3$): 0.97(s, 9H), 2.24(s, 3H), 2.68(t, 4H), 3.05-3.15(m, 4H), 3.37(d, 2H), 3.60(s, 2H), 5.68-5.76(m, 1H), 7.70(m, 4H), 8.17(s, 1H) |
| 12-19 | 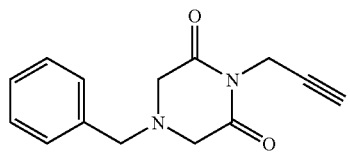 | 51 | 0.33 (AcOEt only) | (CDCl$_3$): 0.98(s, 9H), 2.25-2.35(m, 2H), 2.71(t, 4H), 3.10(t, 3H), 3.35-3.42(m, 4H), 3.38(d, 2H), 3.68(s, 2H), 3.69(t, 3H), 5.75(m, 1H), 8.22(s, 1H) |

12-23

5-[3-(4-Benzyl-2,6-dioxo-piperazin-1-yl)-prop-1-ynyl]-4-(2,2-dimethyl-propylamino)-pyrimidine-2-carbonitrile

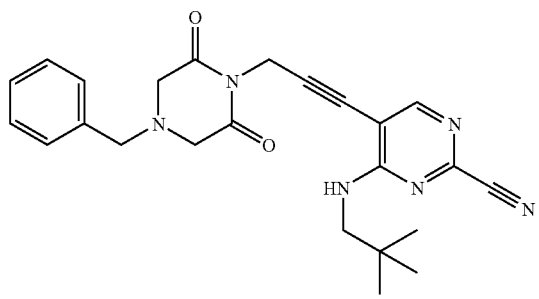

A. 4-Benzyl-1-prop-2-ynyl-piperazine-2,6-dione

To a suspension of N-benzyliminodiacetic acid (10 mmol) in THF (30 ml), 1,1'-carbonyldiimidazole (22 mmol) is added with stirring. The reaction mixture is refluxed with stirring for 15 minutes. Propargylamine (100 mmol) is added and then reaction mixture is stirred at 90° C. for 1 day. The organic solvent is evaporated and then the residue is dissolved in AcOEt. The organic layer is washed with 2×100 ml 0.1N HCl and then dried over sodium sulfate. The solvent is concentrated under vacuum. The purification of the residue by silica gel column chromatography affords 1.5 g of title compound in 62% yield. Rf=0.24 (n-hexane:AcOEt=3:1)

B. 5-[3-(4-Benzyl-2,6-dioxo-piperazin-1-yl)-prop-1-ynyl]-4-(2,2-dimethyl-propylamino)-pyrimidine-2-carbonitrile

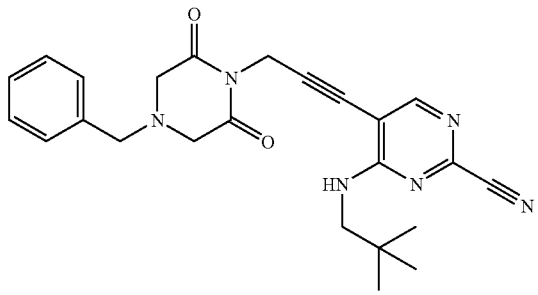

To a solution of 4-benzyl-1-prop-2-ynyl-piperazine-2,6-dione (1.5 mmol) and 5-bromo-4-(2,2-dimethyl-propylamino)-pyrimidine-2-carbonitrile (1 mmol) in DMF (5 ml), triethylamine (3.0 mmol), dichlorobis(triphenylphosphine)palladium (II) (0.1 mmol) and copper (I) iodide (0.2 mmol) are added. The reaction mixture is heated at 85° C. ca. for 1 day. Saturated aqueous solution of ammonium chloride is added to the reaction mixture and then aqueous layer is extracted with two 50 ml portions of AcOEt. The combined extracts are washed with brine, dried over magnesium sulfate and concentrated under vacuum to give crude product, which is purified by silica gel column chromatography. Yield: 93%. Rf=0.3 (AcOEt only)

$^1$H NMR(400 MHz, CDCl$_3$) δ 0.96(s, 9H), 3.36(d, 2H), 3.46(s, 4H), 3.65(s, 2H), 4.77(s, 2H), 6.02-6.04(m, 1H), 7.27 (d, 2H), 7.34(t, 3H), 8.16(s, 1H)

Example 13 describes the preparation of substituted 4-amino-pyrimidine-2-carbonitriles

Example 13-1

4-[{4-[3-(4-Acetyl-piperazin-1-yl)-prop-1-ynyl]-benzyl}-(2,2-dimethyl-propyl)-amino]-pyrimidine-2-carbonitrile

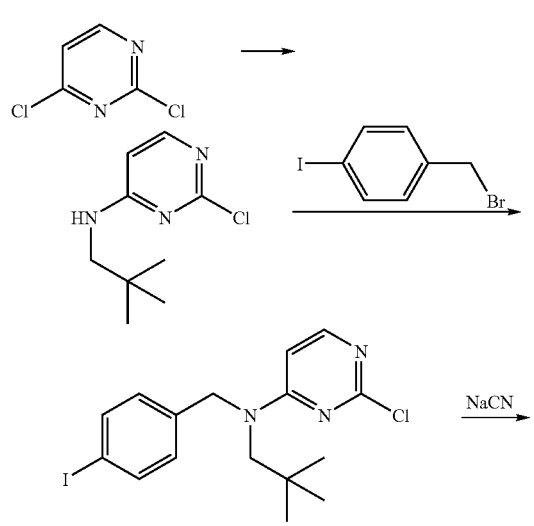

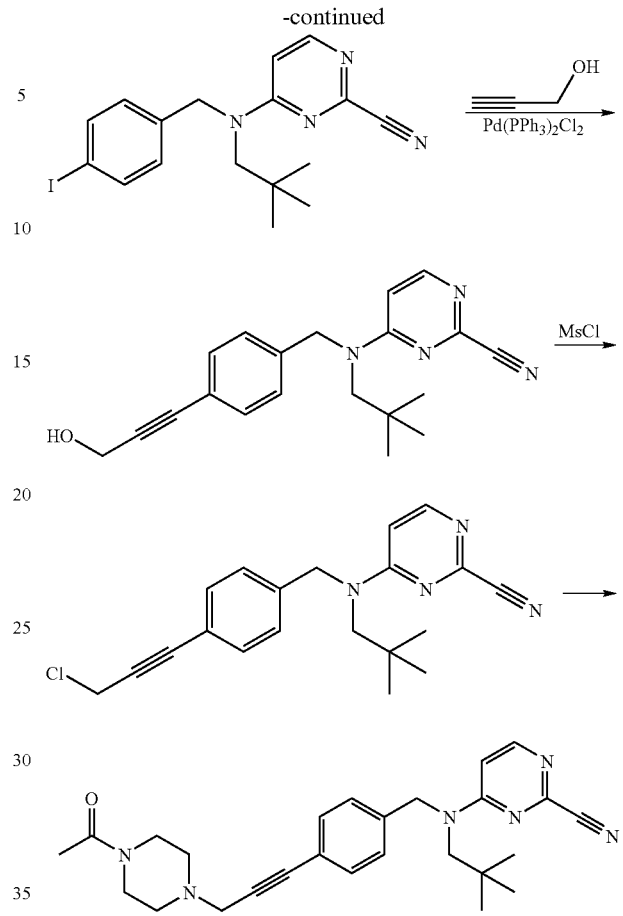

A) (2-Chloro-pyrimidin-4-yl)-(2,2-dimethyl-propyl)-amine

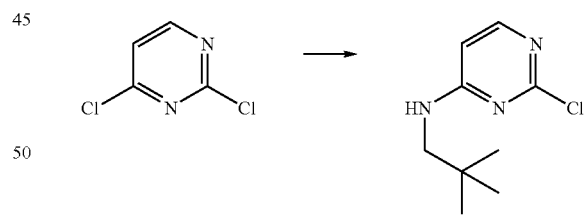

2,4-Dichloropyrimidine (25 g, 0.16 moles) and 2,2-dimethyl-propylamine (25 ml, 0.21 moles) are dissolved in 250 ml of THF and K$_2$CO$_3$ (33.1 g, 0.24 mmoles) is added at rt. The mixture is refluxed at rt for 8 h. Water is added and the organic layer is extracted with AcOEt, washed with brine, dried over magnesum sulfate and concentrated. The crude product is purified by silica gel column chromatography to give 22 g of desired (2-chloro-pyrimidin-4-yl)-(2,2-dimethyl-propyl)-amine in 67% yield.

$^1$H NMR (400 MHz, CDCl$_3$) δ 0.98 (s, 9H), 3.02 (brs, 2H), 5.15 (brs, 1H), 6.25 (d, 1H), 8.03 (brs, 2H) Rf=0.32 (n-Hexane:AcOEt=1:1)

B) (2-Chloro-pyrimidin-4-yl)-(2,2-dimethyl-propyl)-(4-iodo-benzyl)-amine

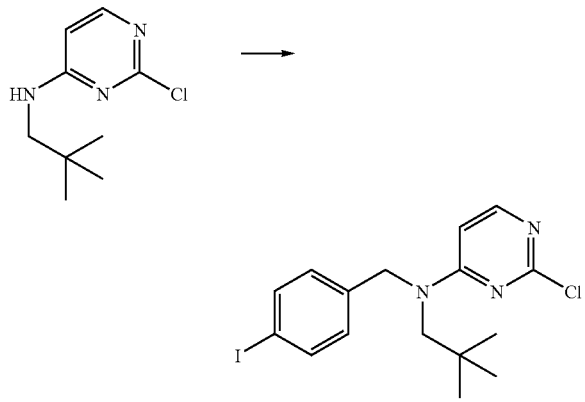

13-1A (4.8 g, 24.0 mmoles) and 1-bromomethyl-4-iodobenzene (8.6 g, 28.5 mmoles) are dissolved in 25 ml of DMF and NaH (1.6 g, 40.9 mmoles, 60% oil suspenstion) is added at 0° C. The mixture is stirred at rt for 4 h. Water is added and the organic layer is extracted with AcOEt, washed with brine, dried over magnesum sulfate and concentrated. The crude product is purified by silica gel column chromatography to give 10.1 g of desired (2-chloro-pyrimidin-4-yl)-(2,2-dimethyl-propyl)-(4-iodo-benzyl)-amine in 100% yield.

$^1$H NMR (400 MHz, CDCl$_3$) δ 1.01 (s, 9H), 3.44 (brs, 2H), 4.77 (brs, 2H), 6.30 (brs, 11), 6.88 (d, 2H), 7.65 (d, 2H), 7.97 (d, 2H) Rf=0.50 (n-Hexane:AcOEt=1:1)

C) 4-[(2,2-Dimethyl-propyl)-(4-iodo-benzyl)-amino]-pyrimidine-2-carbonitrile

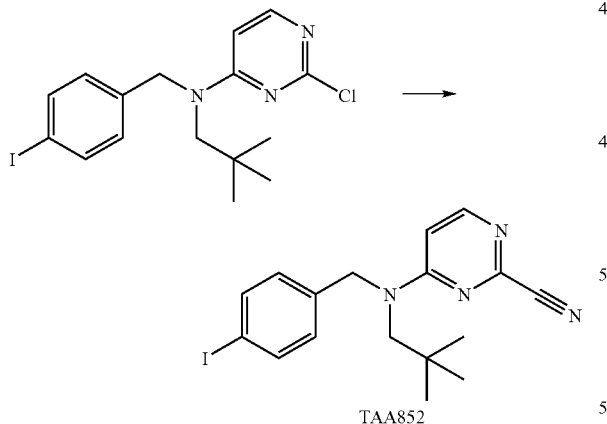

(2-Chloro-pyrimidin-4-yl)-(2,2-dimethyl-propyl)-(4-iodo-benzyl)-amine (10.0 g, 24.0 mmoles) and sodium cyanide (5.6 g, 0.12 moles) are dissolved in 40 ml of DMSO and 1,4-diaza bicyclo[2,2,2]octane (0.27 g, 2.4 mmoles) is added at rt. The mixture is stirred at 75° C. for 21 h. Water is added and the organic layer is extracted with AcOEt, washed with brine, dried over magnesum sulfate and concentrated. The crude product is purified by silica gel column chromatography to give 8.4 g of desired 4-[(2,2-dimethyl-propyl)-(4-iodo-benzyl)-amino]-pyrimidine-2-carbonitrile in 86% yield.

$^1$H NMR (400 MHz, CDCl$_3$) δ 1.01 (s, 9H), 3.32 (brs, 2H), 4.75 (brs, 2H), 6.46 (brs, 1H), 6.99 (d, 2H), 7.69 (d, 2H), 8.27 (brs, 2H) Rf=0.50 (n-Hexane:AcOEt)=1:1

D) 4-{(2,2-Dimethyl-propyl)-[4-(3-hydroxy-prop-1-ynyl)-benzyl]-amino}-pyrimidine-2-carbonitrile

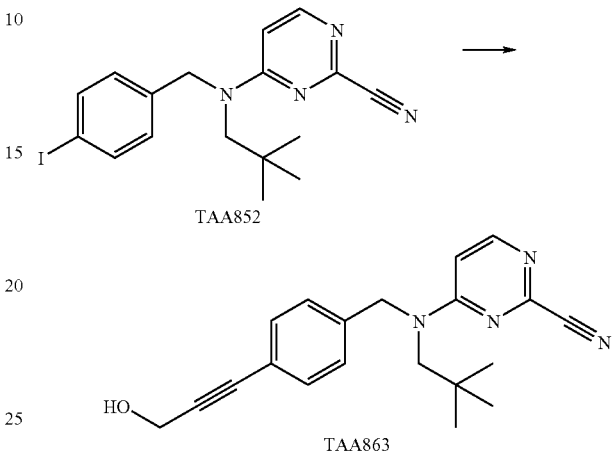

13-1C (8.4 g, 20.7 mmoles), prop-2-yn-1-ol (3.6 ml, 62.0 mmoles), CuI (0.4 g, 2.1 mmol) and ethyl-diisopropyl-amine (17.8 ml, 1.1 moles) are dissolved in 100 ml of DMF and Pd(PPh$_3$)$_2$Cl$_2$ (0.7 g, 1.1 mmoles) is added at rt. The mixture is stirred at rt for 1 h. Water is added and the organic layer is extracted with AcOEt, washed with brine, dried over magnesum sulfate and concentrated. The crude product is purified by silica gel column chromatography to give 6.1 g of desired 4-{(2,2-dimethyl-propyl)-[4-(3-hydroxy-prop-1-ynyl)-benzyl]-amino}-pyrimidine-2-carbonitrile in 82% yield.

$^1$H NMR (400 MHz, CDCl$_3$) δ 1.03 (s, 9H), 1.69 (t, 1H), 3.65 (brs, 2H), 4.43 (d, 2H), 4.79 (brs, 2H), 6.48 (brs, 1H), 7.18 (d, 2H), 7.43 (d, 2H), 8.11 (brs, 2H) Rf=0.29 (n-Hexane:AcOEt=1:1)

E) 4-[[4-(3-Chloro-prop-1-ynyl)-benzyl]-(2,2-dimethyl-propyl)-amino]-pyrimidine-2-carbonitrile

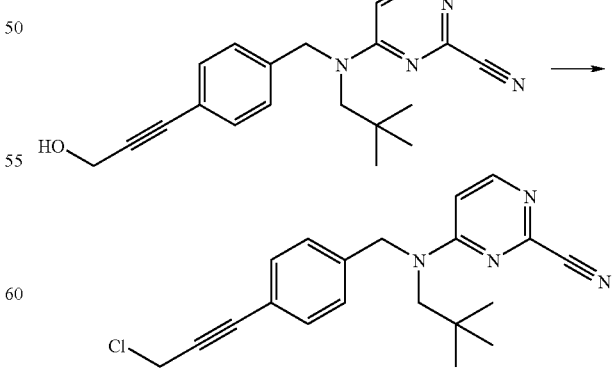

13-1D (6.0 g, 18.1 mmoles) and ethyl-diisopropyl-amine (15.7 ml, 90.7 mmoles) are dissolved in 120 ml of dichloromethane and methansulfonyl chloride (3.5 ml, 45.3 mmoles) is added at 0° C. The mixture is stirred at rt for overnight. Water is added and the organic layer is extracted with dichloromethane, dried over magnesum sulfate and concentrated. The crude product is purified by silica gel column chromatography to give 5.4 g of desired 4-[[4-(3-chloro-prop-1-ynyl)-benzyl]-(2,2-dimethyl-propyl)-amino]-pyrimidine-2-carbonitrile in 85% yield.

$^1$H NMR (400 MHz, CDCl$_3$) δ 1.02 (s, 9H), 3.65 (brs, 2H), 4.36 (s, 2H), 4.81 (brs, 2H), 6.45 (brs, 1H), 7.06 (d, 2H), 7.40 (d, 2H), 8.11 (brs, 2H) Rf=0.65 (n-Hexane:AcOEt=1:1)

F) 4-[{4-[3-(4-Acetyl-piperazin-1-yl)-prop-1-ynyl]-benzyl}-(2,2-dimethyl-propyl)-amino]-pyrimidine-2-carbonitrile

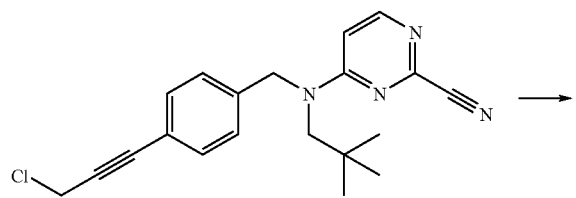

→

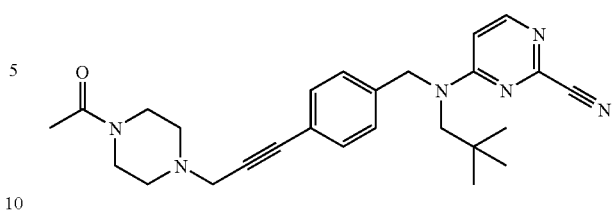

13-1E (70 mg, 0.20 mmoles) is dissolved in 3 ml of DMF and 1-piperazin-1-yl-ethanone (50.1 mg, 0.40 mmoles) is added at rt. The mixture is stirred at rt for overnight. Water is added and the organic layer is extracted with AcOEt, dried over magnesum sulfate and concentrated. The crude product is purified by silica gel column chromatography to give 67 mg of desired 4-[{4-[3-(4-acetyl-piperazin-1-yl)-prop-1-ynyl]-benzyl}-(2,2-dimethyl-propyl)-amino]-pyrimidine-2-carbonitrile in 75% yield.

By repeating the procedure described above using appropriate starting material and conditions the following compounds of formula 13-1 are obtained as identified below in Table 13-1.

TABLE 13-1

13-1

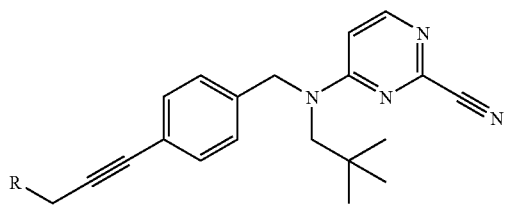

| Expl. No | R | Yield (%) | Rf (solvent) | $^1$H NMR(400 MHz, CDCl3, δ) |
|---|---|---|---|---|
| 13-1 | ![structure] acetyl-piperazine | 75 | 0.50 (MeOH:CH$_2$Cl$_2$ = 1:5) | 1.02(s, 9H), 2.10(s, 3H), 2.60(pent, 4H), 3.52(t, 2H), 3.54(s, 2H), 3.68(t, 2H), 4.79(brs, 2H), 6.47(brs, 1H), 7.03(d, 2H), 7.37(d, 2H), 8.19(brs, 2H) |
| 13-2 | ![structure] formyl-piperazine | 90 | 0.19 (AcOEt:MeOH = 9:1) | 1.02(s, 9H), 2.56-2.66(m, 4H), 3.44(t, 2H), 3.55(s, 2H), 3.62(t, 2H), 3.68(brs, 2H), 4.86(br, 2H), 6.47(br, 1H), 7.04(d, 2H), 7.37(d, 2H), 8.03(s, 1H), 8.10(s, 1H) |
| 13-3 | ![structure] piperidine | 88 | 0.34 (MeOH:CH$_2$Cl$_2$ = 1:10) | 1.02(s, 9H), 1.35-1.46(m, 2H), 1.49-1.68(m, 4H), 2.55(brs, 4H), 3.49(s, 2H), 3.65(brs, 2H), 4.79(brs, 2H), 6.37(brs, 1H), 7.03(d, 2H), 7.37(d, 2H), 8.10(s, 1H) |

TABLE 13-1-continued

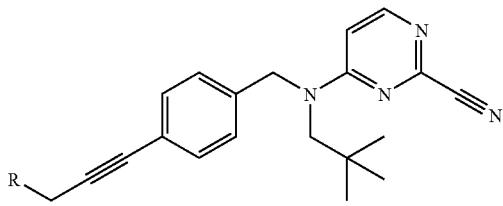

13-1

| Expl. No | R | Yield (%) | Rf (solvent) | ¹H NMR(400 MHz, CDCl3, δ) |
|---|---|---|---|---|
| 13-4 | (4-methylpiperazin-1-yl) | 52 | 0.21 (MeOH) | 1.02(s, 9H), 2.31(s, 3H), 2.51(brs, 4H), 2.67(brs, 4H), 3.51(s, 2H), 3.57(brs, 2H), 4.80(brs, 2H), 6.40(brs, 1H), 7.03(d, 2H), 7.37(d, 2H), 8.10(br, 1H) |
| 13-5 | (1-methylpyrrolidin-2-yl) | 51 | 0.17 (AcOEt:MeOH = 91:1) | 1.02(s, 9H), 1.83(brs, 4H), 2.69(brs, 4H), 3.57(brs, 2H), 3.62(s, 2H), 4.82(brs, 2H), 6.45(br, 1H), 7.03(d, 2H), 7.37(d, 2H), 8.10(br, 1H) |
| 13-6 | (4-methyl-1,4-diazepan-1-yl) | 45 | 0.05 (MeOH) | 1.02(s, 9H), 1.76-1.92(m, 2H), 2.40(s, 3H), 2.78(brs, 4H), 2.78-2.89(m, 4H), 3.57(s, 2H), 3.59(brs, 2H), 4.78(brs, 2H), 6.39(brs, 1H), 7.03(d, 2H), 7.37(d, 2H), 8.10(brs, 1H) |
| 13-7 | (azepan-1-yl) | 90 | 0.15 (AcOEt:Hexane = 1:1) | 1.02(s, 9H), 1.59-1.64(m, 4H), 1.69-1.74(m, 4H), 2.74(t, 4H), 3.57(s, 2H), 3.59(brs, 2H), 4.79(brs, 2H), 6.39(brs, 1H), 7.03(d, 2H), 7.37(d, 2H), 8.10(brs, 1H) |
| 13-8 | (1-methylpiperidin-4-yl)piperidin-1-yl | 90 | 0.35 (MeOH:CH₂Cl₂ = 1:2) | 1.02(s, 9H), 1.25-1.78(m, 10H), 1.80-1.99(m, 1H), 2.25(t, 2H), 2.57(brs, 4H), 3.04(d, 2H), 3.49(s, 2H), 3.66(brs, 2H), 4.75(brs, 2H), 6.58(brs, 1H), 7.03(d, 2H), 7.37(d, 2H), 8.10(brs, 1H) |
| 13-9 | (1-methylpiperidin-4-yl)pyrrolidin-1-yl | 85 | 0.05 (MeOH) | 1.02(s, 9H), 1.55-1.68(m, 2H), 1.75-1.83(m, 4H), 1.90-2.03(m, 2H), 2.28(t, 2H), 2.55-2.63(m, 4H), 2.94(d, 2H), 3.49(s, 2H), 3.30-3.85(m, 3H), 4.79(br, 2H), 6.394(br, 1H), 7.03(d, 2H), 7.38(d, 2H), 8.10(s, 1H) |

TABLE 13-1-continued

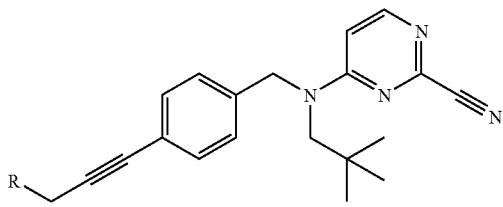

13-1

| Expl. No | R | Yield (%) | Rf (solvent) | ¹H NMR(400 MHz, CDCl3, δ) |
|---|---|---|---|---|
| 13-10 | (1-methylpiperazinyl-CH₂–) | 69 | 0.10 (AcOEt:MeOH = 5:1) | 1.02(s, 9H), 1.10(t, 3H), 2.45(q, 2H), 2.33-2.89(m, 8H), 3.57(s, 2H), 3.66(brs, 2H), 4.78(brs, 2H), 6.39(brs, 1H), 7.03(d, 2H), 7.37(d, 2H), 8.10(brs, 1H) |
| 13-11 | (4-methylpiperazinyl-CH(CH₃)–) | 92 | 0.07 (AcOEt:MeOH = 5:1) | 1.02(s, 9H), 1.05(d, 6H), 2.58-2.82(m, 9H), 3.50(s, 2H), 3.67(brs, 2H), 4.78(brs, 2H), 6.44(brs, 1H), 7.03(d, 2H), 7.37(d, 2H), 8.10(s, 1H) |
| 13-12 | (4-ethylsulfonylpiperazinyl-CH₂–) | 68 | 0.23 (AcOEt) | 1.02(s, 9H), 1.38(t, 3H), 2.70(t, 4H), 2.96(q, 2H), 3.38(t, 4H), 3.55(s, 2H), 3.66(brs, 2H), 4.78(brs, 2H), 6.39(brs, 1H), 7.03(d, 2H), 7.37(d, 2H), 8.10(brs, 1H) |
| 13-13 | (1-methyl-4-hydroxypiperidin-4-yl) | 88 | 0.20 (AcOEt) | 1.02(s, 9H), 1.48-1.58(m, 1H), 1.59-1.72(m, 2H), 1.92-2.02(m, 2H), 2.40(t, 2H), 2.88-2.93(m, 2H), 3.49(s, 2H), 3.52-3.82(m, 3H), 4.79(brs, 2H), 6.37(brs, 1H), 7.03(d, 2H), 7.37(d, 2H), 8.10(s, 1H) |
| 13-14 | (1-methyl-4-oxopiperidin-3-yl) | 77 | 0.50 (AcOEt) | 1.02(s, 9H), 2.52(t, 4H), 2.97(t, 4H), 3.49(brs, 2H), 3.64(s, 2H), 4.79(brs, 2H), 6.37(brs, 1H), 7.03(d, 2H), 7.37(d, 2H), 8.10(s, 1H) |
| 13-15 | (cyclohexyl-NH–) | 83 | 0.19 (AcOEt) | 1.02(s, 9H), 1.07-1.41(m, 6H), 1.58-1.66(m, 1H), 1.72-1.81(m, 2H), 1.88-1.95(m, 2H), 2.67-2.76(m, 1H), 2.40(t, 2H), 3.46(brs, 2H), 3.66(s, 2H), 4.76(brs, 2H), 6.37(brs, 1H), 7.03(d, 2H), 7.37(d, 2H), 8.10(s, 1H) |

TABLE 13-1-continued 13-1

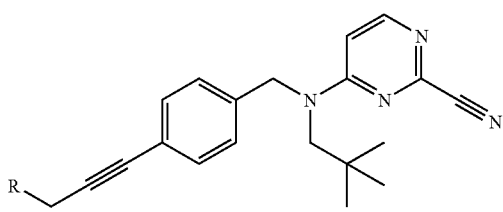

| Expl. No | R | Yield (%) | Rf (solvent) | ¹H NMR(400 MHz, CDCl3, δ) |
|---|---|---|---|---|
| 13-16 | piperidine-N-NH-CH< | 11 | 0.45 (AcOEt) | 1.02(s, 9H), 1.40-1.83(m, 7H), 2.52-2.63(m, 4H), 3.49(s, 2H), 3.66(brs, 2H), 4.76(brs, 2H), 6.37(brs, 1H), 7.03(d, 2H), 7.37(d, 2H), 8.10(s, 1H) |
| 13-17 | 1-methylpiperidin-4-yl-CH₂NH₂ | 52 | 0.25 (MeOH:CH₂Cl₂ = 1:3) | 1.02(s, 9H), 1.26-1.38(m, 1H), 1.42-1.63(m, 4H), 1.77(d, 2H), 2.22(t, 2H), 2.59(d, 2H), 3.00(d, 2H), 3.49(s, 2H), 3.63(brs, 2H), 4.79(brs, 2H), 6.37(brs, 1H), 7.03(d, 2H), 7.37(d, 2H), 8.10(s, 1H), |
| 13-18 | 1-methylpiperidine-4-carboxylic acid | 33 | 0.01 (AcOEt) | 1.02(s, 9H), 1.78-2.28(m, 5H), 2.38-2.46(m, 2H), 2.98-3.04(m, 2H), 3.54(s, 2H), 3.63(brs, 2H), 4.79(brs, 2H), 6.37(brs, 1H), 7.03(d, 2H), 7.37(d, 2H), 8.10(s, 1H), 10.05(brs, 1H) |
| 13-19 | (1-methylpiperidin-4-yl)methanol | 63 | 0.05 (AcOEt) | 1.02(s, 9H), 1.27-1.38(m, 2H), 1.47-1.62(m, 2H) 1.77(d, 2H), 2.26(t, 2H), 3.01(d, 2H), 3.54(s, 2H), 3.41-3.59(m, 2H), 3.63(brs, 2H), 4.79(brs, 2H), 6.37(brs, 1H), 7.03(d, 2H), 7.37(d, 2H), 8.10(s, 1H) |
| 13-20 | 2-morpholinoethyl-NH- | 68 | 0.11 (MeOH) | 1.02(s, 9H), 1.59(brs, 1H), 2.46(t, 4H), 2.52(t, 2H), 2.84(t, 2H), 3.44(brs, 2H), 3.66(s, 2H), 3.70(t, 4H), 4.80(brs, 2H), 6.37(brs, 1H), 7.03(d, 2H), 7.37(d, 2H), 8.10(s, 1H) |
| 13-21 | 2-piperidinoethyl-NH- | 78 | 0.14 (MeOH) | 1.02(s, 9H), 1.32-1.64(m, 7H), 2.27-2.43(m, 4H), 2.47(t, 2H), 2.83(t, 2H), 3.49(s, 2H), 3.66(brs, 2H), 4.80(brs, 2H), 6.37(brs, 1H), 7.03(d, 2H), 7.37(d, 2H), 8.10(s, 1H) |

TABLE 13-1-continued
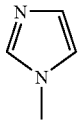
13-1
| Expl. No | R | Yield (%) | Rf (solvent) | $^1$H NMR(400 MHz, CDCl3, δ) |
|---|---|---|---|---|
| 13-22 | 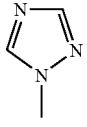 | 100 | 0.36 (AcOEt:MeOH = 9:1) | 1.02(s, 9H), 3.52(brs, 2H), 4.82(brs, 2H), 4.94(s, 2H), 6.46(brs, 1H), 7.06-7.14(m, 4H), 7.39(d, 2H), 7.64(s, 1H), 8.11(s, 1H) |
| 13-23 | | 64 | 0.40 (AcOEt:Hexane = 1:1) | 1.02(s, 9H), 3.65(brs, 1H), 4.89(brs, 2H), 5.20(s, 1H), 6.57(brs, 1H), 7.08(d, 2H), 7.42(d, 2H), 7.98(s, 1H), 8.12(s, 1H), 8.33(s, 1H) |
| 13-24 | —NH$_2$ | 62 | 0.07(AcOEt:MeOH = 9:1) | 1.02(s, 9H), 1.36-1.45(m, 2H), 3.50, (brs, 2H), 3.63(d, 2H), 4.93(brs, 2H), 6.39(br, 1H), 7.03(d, 2H), 7.35(d, 2H), 8.10(s, 1H) |
13-25
1-[3-(4-{[(2-Cyano-pyrimidin-4yl)-(2,2-dimethyl-propyl)-amino]-methyl}-phenyl)-prop-2-ynyl]-piperidine-4-carboxylic acid [1,2,4]triazol-4-ylamide
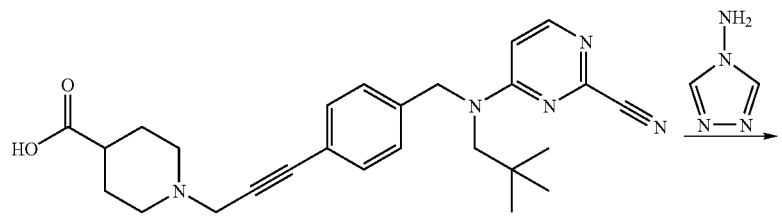
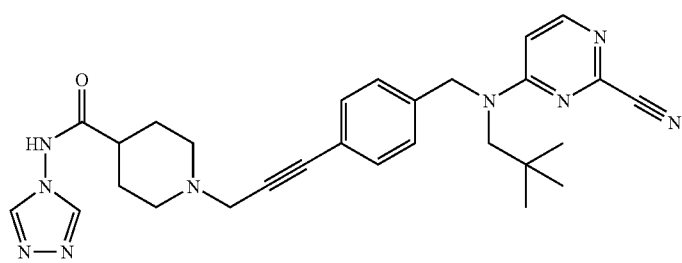

13-18 (56 mg, 0.13 mmoles) and 4-amino-1,2,4-triazole (21 mg, 0.25 mmoles) are dissolved in 3 ml of DMF and HOBT (36 mg, 0.26 mmoles) and WSCD (34 mg, 0.18 mmoles) are added at 0° C. The mixture is stirred at rt for overnight. Water is added and the organic layer is extracted with AcOEt, dried over magnesum sulfate and concentrated. The crude product is purified by silica gel column chromatography to give 56 mg of desired 1-[3-(4-{[(2-cyano-pyrimidin-4-yl)-(2,2-dimethyl-propyl)-amino]-methyl}-phenyl)-prop-2-ynyl]-piperidine-4-carboxylic acid [1,2,4]triazol-4-ylamide in 56% yield.

By repeating the procedure described above using appropriate starting material and conditions the following compounds of formula 13-2 are obtained as identified below in Table 13-2.

TABLE 13-2

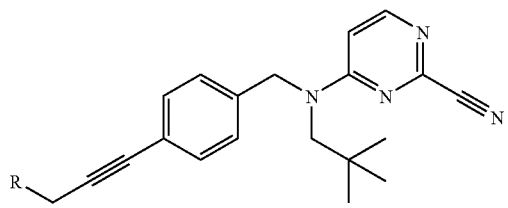

| Expl. No | R | Yield (%) | Rf (solvent) | $^1$H NMR(400 MHz, CDCl3, δ) |
|---|---|---|---|---|
| 13-25 | 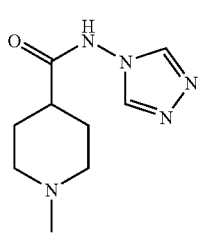 | 56 | 0.45 (CH$_2$Cl$_2$:MeOH = 4:1) | 1.02(s, 9H), 1.91-2.07(m, 4H), 2.31-2.48(m, 3H), 3.01-3.29(m, 2H), 3.49(s, 1H), 3.53(s, 2H), 3.69(brs, 2H), 4.80(brs, 2H), 6.57(brs, 1H), 7.04(d, 2H), 7.39(d, 2H), 8.12(s, 3H) |
| 13-26 | 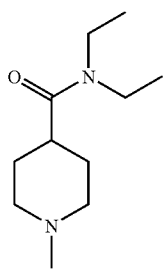 | 76 | 0.43 (AcOEt:MeOH = 5:1) | 1.02(s, 9H), 1.10(t, 3H), 1.19(t, 3H), 1.89-2.20(m, 2H), 2.23-2.43(m, 3H), 3.01(d, 2H), 3.34(q, 2H), 3.37(q, 2H), 3.52(s, 2H), 3.66(brs, 2H), 4.80(brs, 2H), 6.57(brs, 1H), 7.04(d, 2H), 7.39(d, 2H), 8.10(s, 1H) |

13-27

4-{(2,2-Dimethyl-propyl)-[2-fluoro-4-(3-piperidin-1-yl-prop-1-ynyl)-benzyl]-amino}-pyrimidine-2-carbonitrile

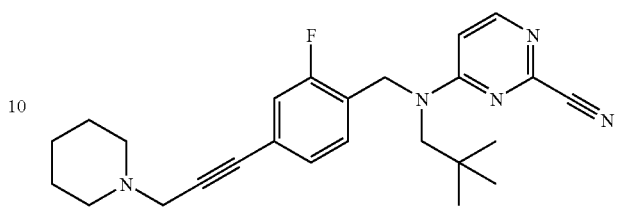

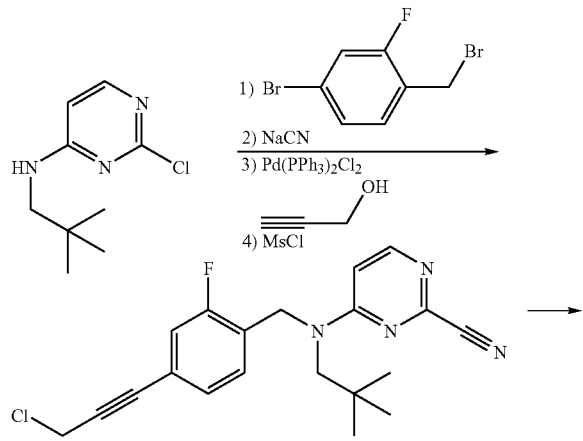

-continued

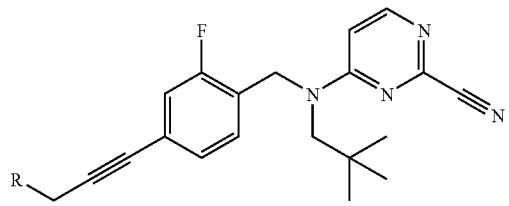

By repeating the procedure described in Example 11-1 using appropriate starting material and conditions the following compounds of formula 13-3 are obtained as identified below in Table 13-3.

TABLE 13-3

13-3

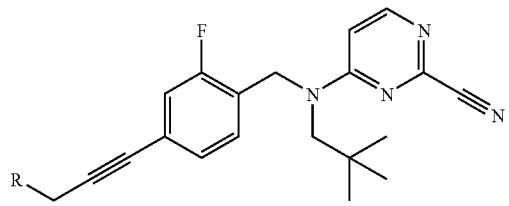

| Expl. No | R | Yield (%) | Rf (solvent) | $^1$H NMR(400 MHz, CDCl3, δ) |
|---|---|---|---|---|
| 13-27 | 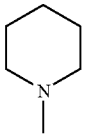 | 61 | 0.12 (AcOEt:Hexane = 1:1) | 1.02(s, 9H), 1.39-1.52(m, 2H), 1.59-1.68(m, 4H), 2.47-2.52(m, 4H), 3.45(s, 2H), 3.66(brs, 2H), 4.83(br, 2H), 6.57(br, 1H), 6.81-7.08(m, 1H), 7.09-7.15(m, 2H), 8.12(s, 1H) |
| 13-28 | 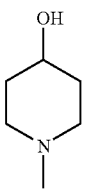 | 92 | 0.28 (AcOEt:MeOH = 5:1) | 1.02(s, 9H), 1.39(brs, 1H), 1.61-1.73(m, 2H), 1.91-2.02(m, 2H), 2.39(t, 2H), 2.81-2.90(m, 2H), 3.23-3.82(m, 3H), 3.49(s, 2H), 4.84(br, 2H), 6.66(brs, 1H), 6.89-7.13(m, 3H), 8.13(d, 1H) |

13-29

4-[(2,2-Dimethyl-propyl)-(4-[1,2,4]triazol-1-yl-benzyl)-amino]-pyrimidine-2-carbonitrile

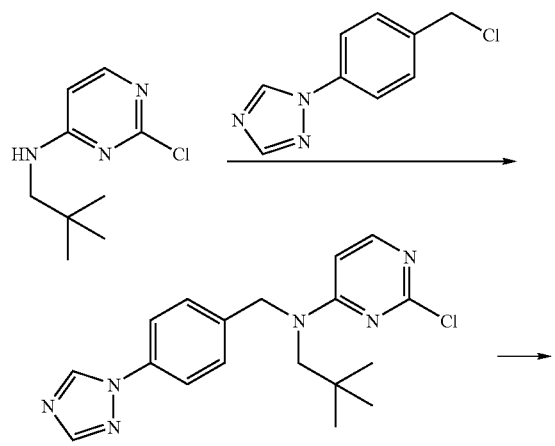

-continued

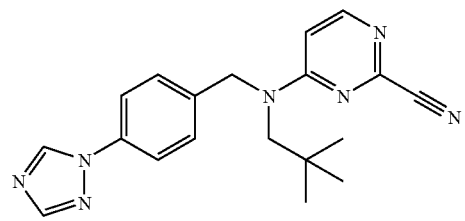

By repeating the procedures described in Examples 13-1-B and 13-1-C using appropriate starting material and conditions, the following compounds of formula 13-4 are obtained as identified below in Table 13-4.

TABLE 13-4

13-4

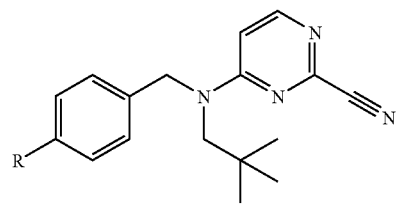

| Expl. No | R | Yield (%) | Rf (solvent) | $^1$H NMR (400 MHz, CDCl3, δ) |
|---|---|---|---|---|
| 13-30 | imidazol-1-yl | 38 | 0.50 (MeOH:CH$_2$Cl$_2$ = 1:9) | 1.05(s, 9H), 3.48(brs, 2H), 4.90(brs, 2H), 6.57(brs, 1H), 7.23(d, 2H), 7.25(brs, 1H), 7.36(d, 2H), 8.10(s, 1H), 8.15(brs, 2H) |
| 13-29 | 1,2,4-triazol-1-yl | 91 | 0.45 (AcOEt) | 1.05(s, 9H), 3.48(brs, 2H), 4.89(brs, 2H), 6.51(brs, 1H), 7.25(d, 2H), 7.63(d, 2H), 8.07(s, 1H), 8.10(s, 1H), 8.53(s, 1H) |
| 13-31 | —CH=CH$_2$ | 59 | 0.40 (AcOEt:Hexane = 1:2) | 1.02(s, 9H), 3.64(brs, 2H), 4.76(brs, 2H), 5.26(t, 1H), 5.72(d, 1H), 6.48(brs, 1H), 6.68(dd, 1H), 7.06(d, 2H), 7.35(s, 2H), 8.09(s, 1H) |

13-32

4-{(2,2-Dimethyl-propyl-[4-(3-methyl-3H-imidazol-4-yl)-benzyl]-amino}-pyrimidine-2-carbonitrile

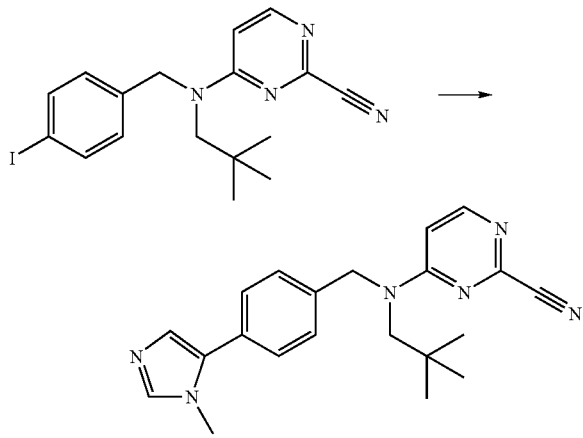

4-{(2,2-Dimethyl-propyl)-[4-iodo-benzyl]-amino}-pyrimidine-2-carbonitrile (200 mg, 0.5 mmoles), 1-methyl imidazole (0.2 ml, 2.5 mmoles), triphenylphosphine (26 mg, 0.10 mmoles) and CsCO3 (160 mg, 0.5 mmoles) are dissolved in 3 ml of DMF and Pd(OAc)2 (10 mg, 0.05 mmoles) is added at rt. The mixture is stirred at 120° C. for 18 h. Water is added and the organic layer is extracted with AcOEt, washed with brine, dried over magnesum sulfate and concentrated. The crude product is purified by silica gel column chromatography to give 104 mg of desired 4-{(2,2-dimethyl-propyl)-[4-(3-methyl-3H-imidazol-4-yl)-benzyl]-amino}-pyrimidine-2-carbonitrile in 59% yield.

$^1$H NMR (400 MHz, CDCl$_3$) δ 1.02 (s, 9H), 3.47 (brs, 2H), 3.66 (s, 3H), 4.87 (brs, 2H), 6.49 (brs, 1H), 6.97 (brs, 1H), 7.18 (d, 2H), 7.35 (d, 2H), 7.52 (s, 1H), 8.14 (brs, 2H), Rf=0.07 (AcOEt)

13-33

4-[(2,2-Dimethyl-propyl)-(4-oxazol-2-yl-benzyl)-amino]-pyrimidine-2-carbonitrile

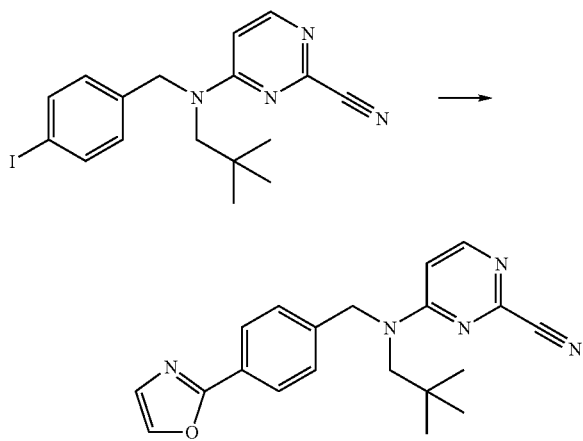

To a solution of oxazole (0.5 ml, 7.2 mmoles) in 10 ml of THF at −78° C. is added BuLi (5.23 ml, 8.0 mmoles, 1.6 M solution in hexane). After 30 min, ZnCl2 (3.0g, 21.7 mmoles) and then a solution of 4-{(2,2-Dimethyl-propyl)-[4-iodo-benzyl]-amino}-pyrimidine-2-carbonitrile (2.9 g, 7.2 mmoles) in 10 ml of THF are added. The reaction mixture is warmed to 0° C. for 1 h. The reaction mixture is added to Pd(PPh$_3$)$_4$ (0.9 g, 0.8 mmoles) and heated to reflux. Water is added and is filtered through a pad of Celite which is wshed with AcOEt. The organic layer is extracted with AcOEt, washed with brine, dried over magnesum sulfate and concentrated. The crude product is purified by silica gel column chromatography to give 104 mg of desired 4-[(2,2-dimethyl-propyl)-(4-oxazol-2-yl-benzyl)-amino]-pyrimidine-2-carbonitrile in 16% yield.

$^1$H NMR (400 MHz, CDCl$_3$) δ 1.04 (s, 9H), 3.64 (brs, 2H), 4.87 (brs, 2H), 6.54 (brs, 1H), 7.20 (d, 2H), 7.23 8s, 1H), 7.78 (s, 1H), 8.00 (d, 2H), 8.12 (brs, 1H) Rf=0.12 (AcOEt:Hexane=1:2)

13-34

4-[(2,2-Dimethyl-propyl)-(4-[1 2,4]triazol-1-ylmethyl-benzyl)-amino]-pyrimidine-2-carbonitrile

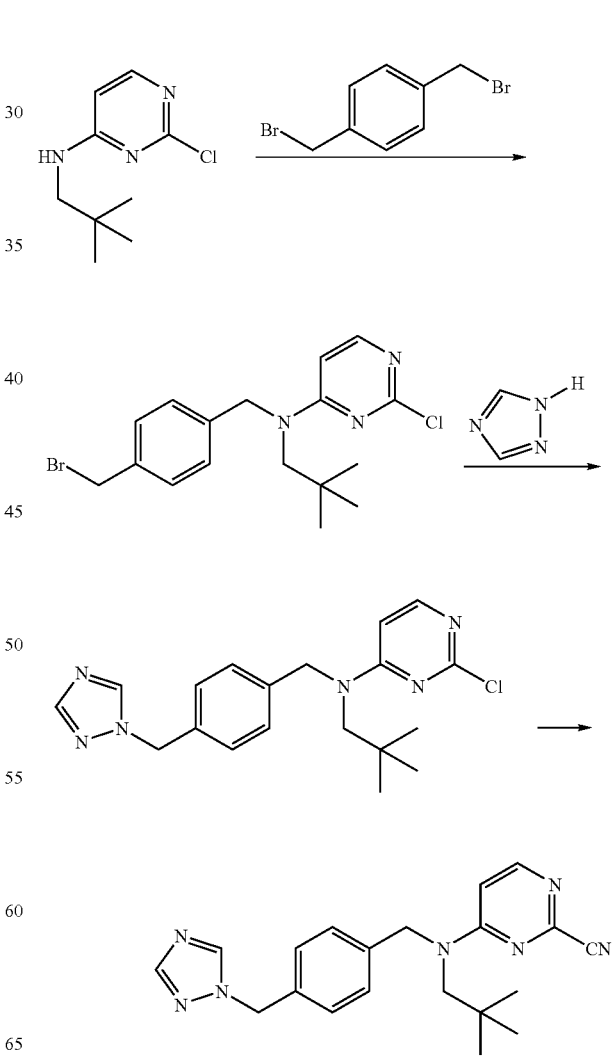

A) (4-Bromomethyl-benzyl)-(2-chloro-pyrimidin-4-yl)-(2,2-dimethyl-propyl)-amine

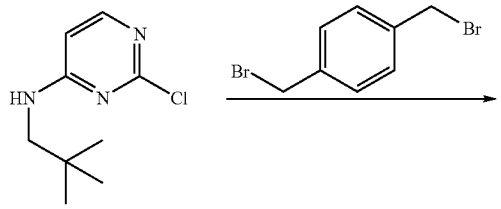

(2-chloro-pyrimidin-4-yl)-(2,2-dimethyl-propyl)-amine (2.0 g, 10.0 mmoles) and 1,4-bis-bromomethyl-benzene (4.0 g, 15.0 mmoles) are dissolved in 50 ml of DMF and NaH (0.8 g, 21.0 mmoles, 60% oil suspenstion) is added at 0° C. The mixture is stirred at rt for overnight. Water is added and the organic layer is extracted with AcOEt, washed with brine, dried over magnesum sulfate and concentrated. The crude product is purified by silica gel column chromatography to give 0.9 g of desired (4-bromomethyl-benzyl)-(2-chloro-pyrimidin-4-yl)-(2,2-dimethyl-propyl)-amine in 24% yield.

Rf=0.76 (n-Hexane:AcOEt=1:1)

B) (2-Chloro-pyrimidin-4-yl)-(2,2-dimethyl-propyl)-(4-[1,2,4]triazol-1-ylmethyl-benzyl)-amine

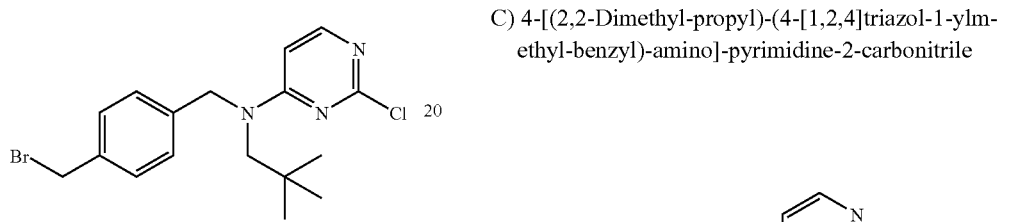

(4-Bromomethyl-benzyl)-(2-chloro-pyrimidin-4-yl)-(2,2-dimethyl-propyl)-amine (0.2 g, 0.5 mmoles) obtained above and 1,2,4-triazole (72 mg, 1.1 mmoles) are dissolved in 5 ml of DMF and NaH (44 mg, 1.1 mmoles, 60% oil suspenstion) is added at 0° C. The mixture is stirred at rt for overnight. Water is added and the organic layer is extracted with AcOEt, washed with brine, dried over magnesum sulfate and concentrated. The crude product is purified by silica gel column chromatography to give 160 mg of desired (2-chloro-pyrimidin-4-yl)-(2,2-dimethyl-propyl)-(4-[1,2,4]triazol-1-ylmethyl-benzyl)-amine in 100% yield.

Rf=0.92, ($CH_2Cl_2$:MeOH=1:9)

C) 4-[(2,2-Dimethyl-propyl)-(4-[1,2,4]triazol-1-ylmethyl-benzyl)-amino]-pyrimidine-2-carbonitrile

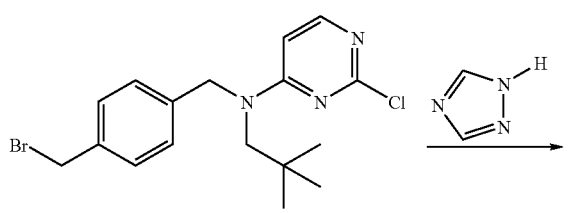

(2-Chloro-pyrimidin-4-yl)-(2,2-dimethyl-propyl)-(4-[1,2,4]triazol-1-ylmethyl-benzyl)-amine (160 mg, 0.43 mmoles) and sodium cyanide (0.1 g, 2.2 mmoles) are dissolved in 5 ml of DMSO and 1,4-diaza bicyclo[2,2,2]octane (23 mg, 0.2 mmoles) is added at rt. The mixture is stirred at rt for 5 h at 70° C. Water is added and the organic layer is extracted with AcOEt, washed with brine, dried over magnesum sulfate and concentrated. The crude product is purified by silica gel column chromatography to give 50 g of desired 4-[(2,2-dimethyl-propyl)-(4-[1,2,4]triazol-1-ylmethyl-benzyl)-amino]-pyrimidine-2-carbonitrile in 32% yield.

By repeating the procedures described in Examples 13-34-B and 13-34-C using appropriate starting material and conditions, the following compounds of formula 13-5 are obtained as identified below in Table 13-5.

TABLE 13-5

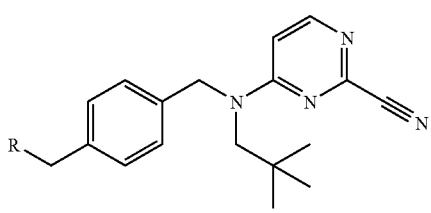

13-5

| Expl. No. | R | Yield (%) | Rf (solvent) | $^1$H NMR(400 MHz, CDCl3, δ) |
|---|---|---|---|---|
| 13-35 | (1-methylimidazol-yl) | 43 | 0.27 (AcOEt:MeOH = 9:1) | 1.02(s, 9H), 3.49(brs, 2H), 4.77(bsr, 2H), 5.10(s, 2H), 6.49(br, 1H), 6.90(s, 1H), 7.08-7.17(m, 5H), 7.54(s, 1H), 8.12(s, 1H) |
| 13-34 | (1-methyl-1,2,4-triazol-yl) | 32 | 0.52 (AcOEt:MeOH = 9:1) | 1.02(s, 9H), 3.49(brs, 2H), 4.89(brs, 2H), 5.32(s, 2H), 6.54(brs, 1H), 7.11(d, 2H), 7.22(d, 2H), 7.97(s, 1H), 8.07(s, 1H), 8.11(s, 1H) |

13-36

4-[(2,2-Dimethyl-propyl)-(4-ethyl-benzyl)-amino]-pyrimidine-2-carbonitrile

A) 4-[(2,2-Dimethyl-propyl)-(4-ethynyl-benzyl)-amino]-pyrimidine-2-carbonitrile

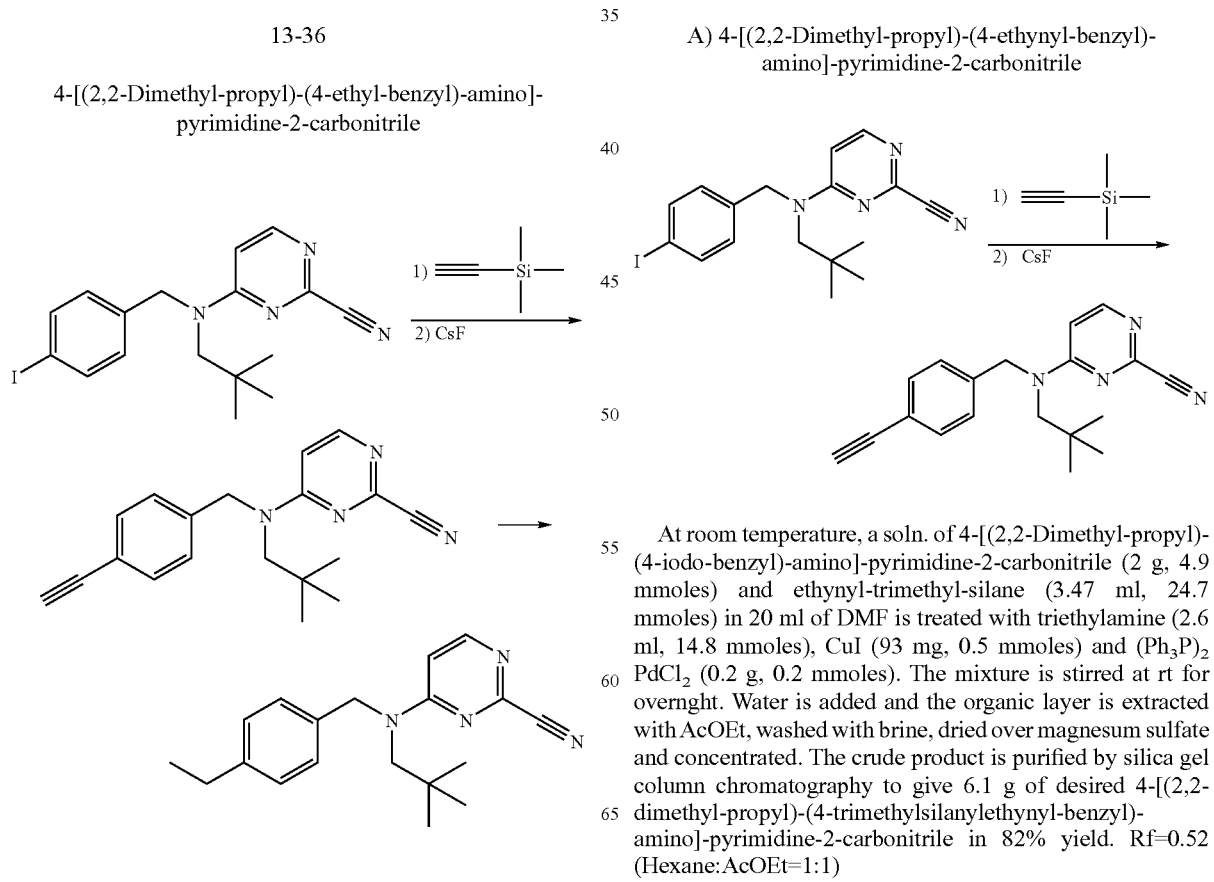

At room temperature, a soln. of 4-[(2,2-Dimethyl-propyl)-(4-iodo-benzyl)-amino]-pyrimidine-2-carbonitrile (2 g, 4.9 mmoles) and ethynyl-trimethyl-silane (3.47 ml, 24.7 mmoles) in 20 ml of DMF is treated with triethylamine (2.6 ml, 14.8 mmoles), CuI (93 mg, 0.5 mmoles) and (Ph$_3$P)$_2$PdCl$_2$ (0.2 g, 0.2 mmoles). The mixture is stirred at rt for overnght. Water is added and the organic layer is extracted with AcOEt, washed with brine, dried over magnesum sulfate and concentrated. The crude product is purified by silica gel column chromatography to give 6.1 g of desired 4-[(2,2-dimethyl-propyl)-(4-trimethylsilanylethynyl-benzyl)-amino]-pyrimidine-2-carbonitrile in 82% yield. Rf=0.52 (Hexane:AcOEt=1:1)

The crude product is dissolved in 30 ml of MeOH and 10 ml of water and CsF (0. 5g, 3.0 mmoles) is added at rt and the mixture is stirred at rt for 2 h. The reaction mixture is evaporated, then water and dichloromethane are added. The organic layer is washed with brine, dried over magnesium sulfate and concentrated. The crude product is purified by silica gel column chromatography to give 4-[(2,2-dimethyl-propyl)-(4-ethynyl-benzyl)-amino]-pyrimidine-2-carbonitrile in 97% yield.

¹H NMR (400 MHz, CDCl₃) δ 1.02 (s, 9H), 3.07 (s, 1H), 3.64 (brs, 2H), 4.81 (brs, 2H), 6.46 (brs,1H), 7.06 (d, 2H), 7.44 (d, 2H), 8.12 (s, 1H) Rf=0.36 (Hexanes:AcOEt=2:1)

B 4-[(2,2-Dimethyl-propyl)-(4-ethyl-benzyl)-amino]-pyrimidine-2-carbonitrile

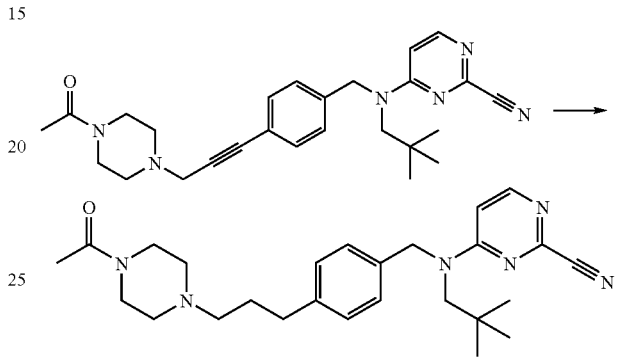

4-[(2,2-Dimethyl-propyl)-(4-ethynyl-benzyl)-amino]-pyrimidine-2-carbonitrile (47 mg, 0.11 mmoles) is dissolved in 5 ml of EtOH and 10% Pd—C (5 mg) is added at rt. The mixture is stirred under hydrogen at rt for overnight and is filtered through a pad of Celite which is washed with EtOH. The filtrate is concentrated and the crude product is purified by silica gel column chromatography to give 38 mg of desired 4-[(2,2-dimethyl-propyl)-(4-ethyl-benzyl)-amino]-pyrimidine-2-carbonitrile in 77% yield.

¹H NMR(400 MHz, CDCl₃) δ 1.02 (s, 9H), 1.21 (t, 3H), 2.62 (q, 2H), 3.67 (brs, 2H), 4.73 (brs,2H), 6.43 (brs, 1H), 7.01 (d, 2H), 7.14 (d, 2H), 8.08 (brs, 1H) Rf=0.80 (Hexanes:AcOEt=1:1)

13-36

4-[{4-[3-(4-acetyl-piperazin-1-yl)-propyl]-benzyl}-(2,2-dimethyl-propyl)-amino]-pyrimidine-2-carbonitrile

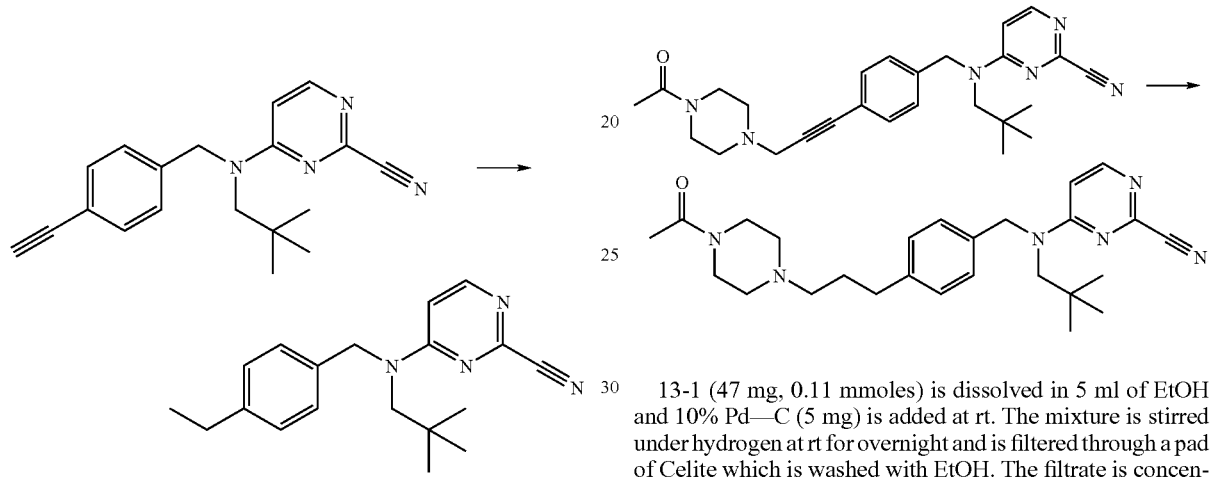

13-1 (47 mg, 0.11 mmoles) is dissolved in 5 ml of EtOH and 10% Pd—C (5 mg) is added at rt. The mixture is stirred under hydrogen at rt for overnight and is filtered through a pad of Celite which is washed with EtOH. The filtrate is concentrated and the crude product is purified by silica gel column chromatography to give 38 mg of desired 4-[{4-[3-(4-acetyl-piperazin-1-yl)-propyl]-benzyl}-(2,2-dimethyl-propyl)-amino]-pyrimidine-2-carbonitrile in 80% yield.

By repeating the procedures described in Examples 13-1-F and 13-37 using appropriate starting material and conditions, the following compounds of formula 13-6 are obtained as identified below in Table 13-6.

TABLE 13-6

13-6

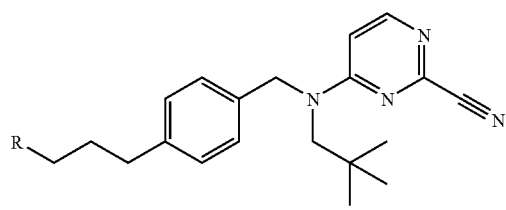

| Example No. | R | Yield (%) | Rf (solvent) | ¹H NMR(400 MHz, CDCl3, δ) |
|---|---|---|---|---|
| 13-37 | acetyl-piperazinyl | 80 | 0.51 (MeOH:CH₂Cl₂ = 1:5) | 1.02(s, 9H), 1.79(pent, 2H), 2.08(s, 3H), 2.31-2.49(m, 6H), 2.62(t, 2H), 3.49(t, 2H), 3.61(t, 2H), 3.76(brs, 2H), 4.76(br, 2H), 6.48(br, 1H), 7.00(d, 2H), 7.12(d, 2H), 8.09(s, 1H) |

TABLE 13-6-continued

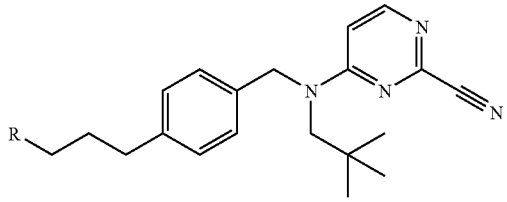

13-6

| Example No. | R | Yield (%) | Rf (solvent) | $^1$H NMR(400 MHz, CDCl3, δ) |
|---|---|---|---|---|
| 13-38 | 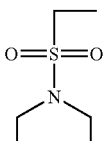 | 75 | 0.20 (AcOEt) | 1.02(s, 9H), 1.37(t, 3H), 1.77(pent, 2H), 2.39(t, 2H), 2.50(t, 4H), 2.92(q, 2H), 3.29(t, 4H), 3.66(brs, 2H), 4.76(br, 2H), 6.49(br, 1H), 7.00(d, 2H), 7.12(d, 2H), 8.09(s, 1H) |
| 13-39 |  | 84 | 0.16 (AcOEt) | 1.02(s, 9H), 1.84(pent, 2H), 2.45-2.53(m, 6H), 2.65(t, 2H), 2.73(t, 4H), 3.66(brs, 2H), 4.74(bsr, 2H), 6.54(brs, 1H), 7.01(d, 2H), 7.14(d, 2H), 8.09(s, 1H) |

13-40

4-((2,2-Dimethyl-propyl)-{4-[3-(4-hydroxyamino-piperidin-1-yl)-prop-1-ynyl]-benzyl}-amino)-pyrimidine-2-carbonitrile

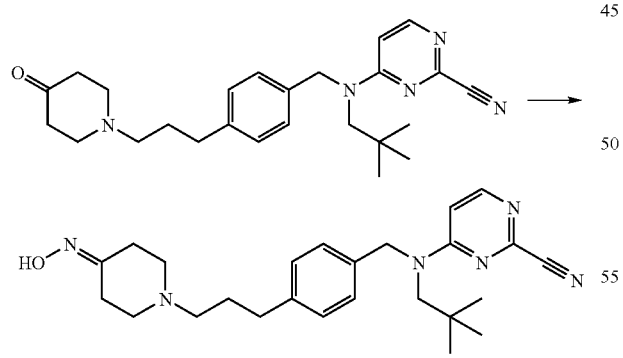

13-39 (130 mg, 0.3 mmoles) and pyridine (0.05 ml, 0.6 mmoles) are dissolved in 5 ml of dichloromethane and hydroxylamine hydrochloride (52 mg, 0.8 mmoles) is added at rt. The mixture is stirred at rt for overnight. Water is added and the organic layer is extracted with AcOEt, dried over magnesum sulfate and concentrated. The crude product is purified by silica gel column chromatography to give 67 mg of 4-((2,2-dimethyl-propyl)-{4-[3-(4-hydroxyamino-piperidin-1-yl)-prop-1-ynyl]-benzyl}-amino)-pyrimidine-2-carbonitrile in 52% yield.

$^1$H NMR (400 MHz, CDCl$_3$) δ 1.02 (s, 9H), 1.81 (pent, 2H), 2.33 (t, 2H), 2.37 (t, 2H), 2.51 (t, 2H), 2.54 (t, 2H), 2.61-2.65 (m, 4H), 3.89 (brs, 2H), 4.74 (brs, 2H), 6.42 (brs, 1H), 6.82 (brs, 1H), 7.00 (d, 2H), 7.13 (d, 2H), 8.08 (s, 1H) Rf=0.33 (AcOEt:MeOH=9:1)

13-41

4-{(2,2-Dimethyl-propyl)-[4-(3-piperidin-1-yl-propyl)-benzyl]-amino}-pyrimidine-2-carbonitrile Methanesulfonic acid 2-(4-{[(2-cyano-pyrimidin-4-yl)-(2,2-dimethyl-propyl)-amino]-methyl}-phenyl)-propyl ester

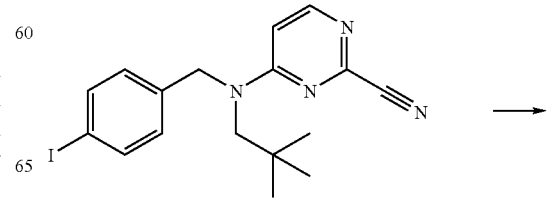

-continued

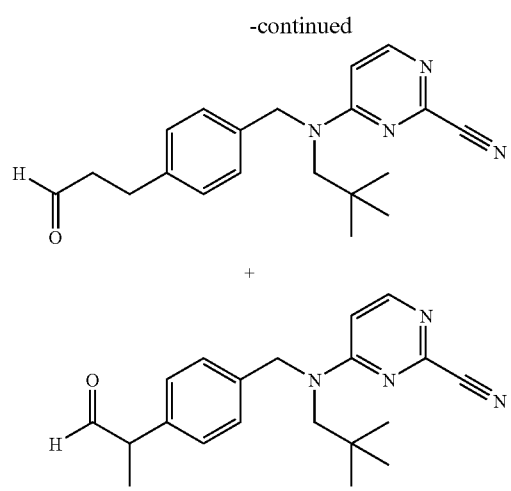

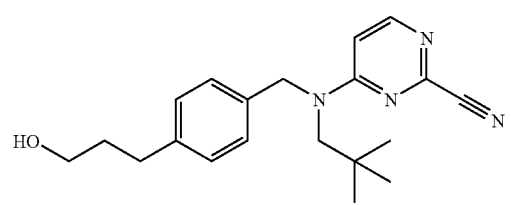

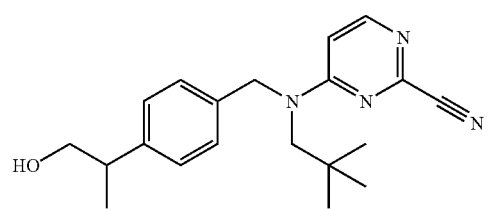

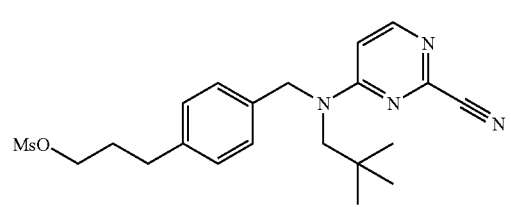

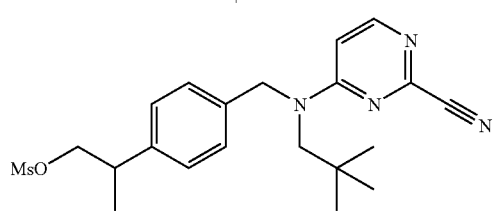

-continued

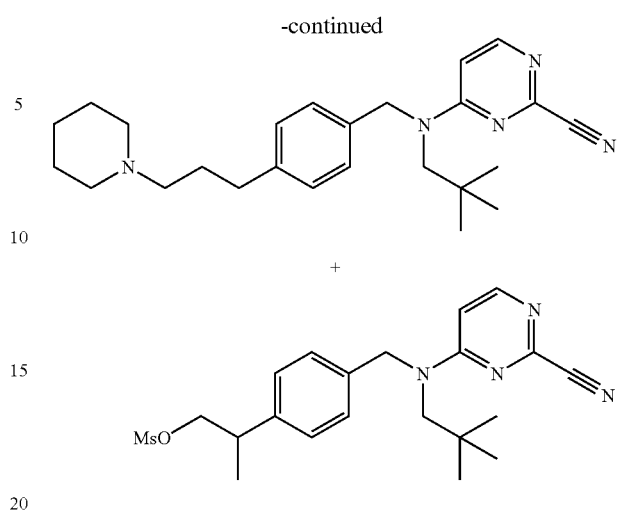

A) 4-1(2,2-Dimethyl-propyl)-[4-(3-oxo-propyl)-benzyl]-amino)-pyrimidine-2-carbonitrile B) 4-{(2,2-Dimethyl-propyl)-[4-(1-methyl-2-oxo-ethyl)-benzyl]-amino}-pyrimidine-2-carbonitrile

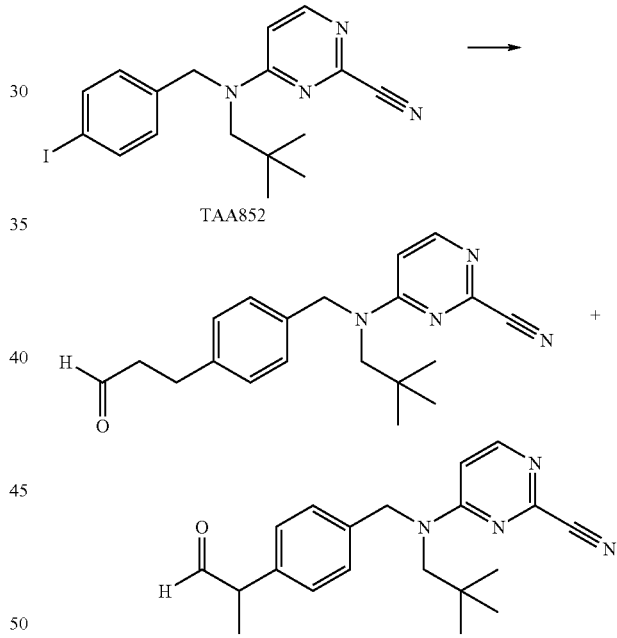

4-[(2,2-Dimethyl-propyl)-(4-iodo-benzyl)-amino]-pyrimidine-2-carbonitrile (1.6 g, 3.8 mmoles), ally alcohol (0.3 ml, 4.8 mmoles), and triethylamine (0.7 ml, 4.8 mmoles) are dissolved in 30 ml of acetonitrile and Pd(OAc)$_2$ (43 mg, 0.19 mmoles) is added at rt. The mixture is stirred at 100° C. for 19 h. The reaction mixture is concentrated and the crude residue is diluted with water. The organic layer is extracted with dichloromethane, washed with brine, dried over magnesium sulfate and concentrated. The crude product is purified by silica gel column chromatography to give 672 mg of inseparable mixture 4-{(2,2-dimethyl-propyl)-[4-(3-oxo-propyl)-benzyl]-amino}-pyrimidine-2-carbonitrile and 4-{(2,2-dimethyl-propyl)-[4-(1-methyl-2-oxo-ethyl)-benzyl]-amino}-pyrimidine-2-carbonitrile in ratio of 3:1 in 52% yield.

Rf=0.60 (n-Hexane:AcOEt=1:1)

C) 4-{(2,2-Dimethyl-propyl)-[4-(3-hydroxy-propyl)-benzyl]-amino}-pyrimidine-2-carbonitrile D) 4-{(2,2-Dimethyl-propyl)-[4-(2-hydroxy-1-methyl-ethyl)-benzyl]-amino}-pyrimidine-2-carbonitrile E) Methanesulfonic acid 3-(4-{[(2-cyano-pyrimidin-4-yl)-(2,2-dimethyl-propyl)-amino]-methyl}-phenyl)-propyl ester F) Methanesulfonic acid 2-(4-{[(2-cyano-pyrimidin-4-yl)-(2,2-dimethyl-propyl)-amino]-methyl}-phenyl)-propyl ester

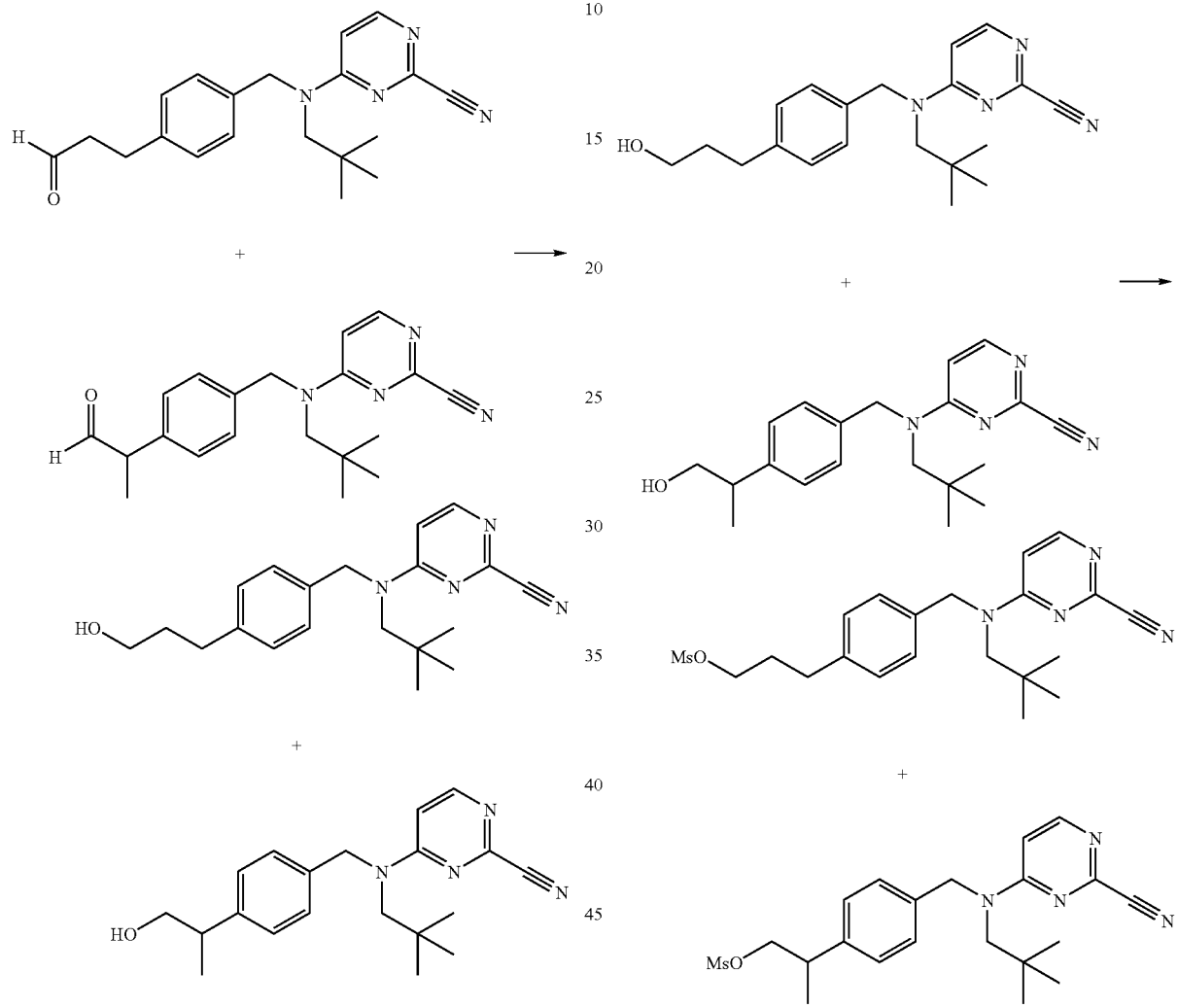

A mixture of 4-{(2,2-dimethyl-propyl)-[4-(3-oxo-propyl)-benzyl]-amino}-pyrimidine-2-carbonitrile and 4-{(2,2-dimethyl-propyl)-[4-(1-methyl-2-oxo-ethyl)-benzyl]-amino}-pyrimidine-2-carbonitrile (in ratio of 3:1) (672 mg, 2.0 mmoles) is dissolved in 15 ml of MeOH and NaBH$_4$ (76 mg, 2.0 mmoles) is added at 0° C. The mixture is stirred at 0° C. for 5 min. The reaction mixture is added 5 ml of acetone, and concentrated. The cude residue is diluted with water and the organic layer is extracted with dichloromethane, washed with brine, dried over magnesum sulfate and concentrated. The crude product is purified by silica gel column chromatography to give 432 mg of inseparable mixture of 4-{(2,2-dimethyl-propyl)-[4-(3-hydroxy-propyl)-benzyl]-amino}-pyrimidine-2-carbonitrile and 4-{(2,2-dimethyl-propyl)-[4-(2-hydroxy-1-methyl-ethyl)-benzyl]-amino}-pyrimidine-2-carbonitrile in ratio of 3:1 in 64% yield.

Rf=0.38 (n-Hexane:AcOEt:=1:1)

A mixture of 4-{(2,2-dimethyl-propyl)-[4-(3-hydroxy-propyl)-benzyl]-amino}-pyrimidine-2-carbonitrile and 4-{(2,2-dimethyl-propyl)-[4-(2-hydroxy-1-methyl-ethyl)-benzyl]-amino}-pyrimidine-2-carbonitrile (in ratio of 3:1) (430 mg, 1.3 mmoles) and ethyl-diisopropyl-amine (0.53 ml, 3.1 mmoles) are dissolved in 10 ml of dichloromethane and methansulfonyl chloride (0.12 ml, 1.5 mmoles) is added at 0° C. The mixture is stirred at rt for 2 h. Water is added and the organic layer is extracted with dichloromethane, dried over magnesum sulfate and concentrated. The crude product is purified by silica gel column chromatography to give 493 mg inseparable mixture of methanesulfonic acid 3-(4-{[(2-cyano-pyrimidin-4-yl)-(2,2-dimethyl-propyl)-amino]-methyl-phenyl)-propyl ester and methanesulfonic acid 2-(4-([(2-cyano-pyrimidin-4-yl)-(2,2-dimethyl-propyl)-amino]-methyl}-phenyl)-propyl ester in ratio of 3:1 in 93% yield.

Rf=0.75 (n-Hexane: AcOEt=1:1)

G) 4-{(2,2-Dimethyl-propyl)-[4-(3-piperidin-1-yl-propyl)-benzyl]-amino}-pyrimidine-2-carbonitrile H) Methanesulfonic acid 2-(4-{[(2-cyano-pyrimidin-4-yl)-(2,2-dimethyl-propyl)-amino]-methyl}-phenyl)-propyl ester

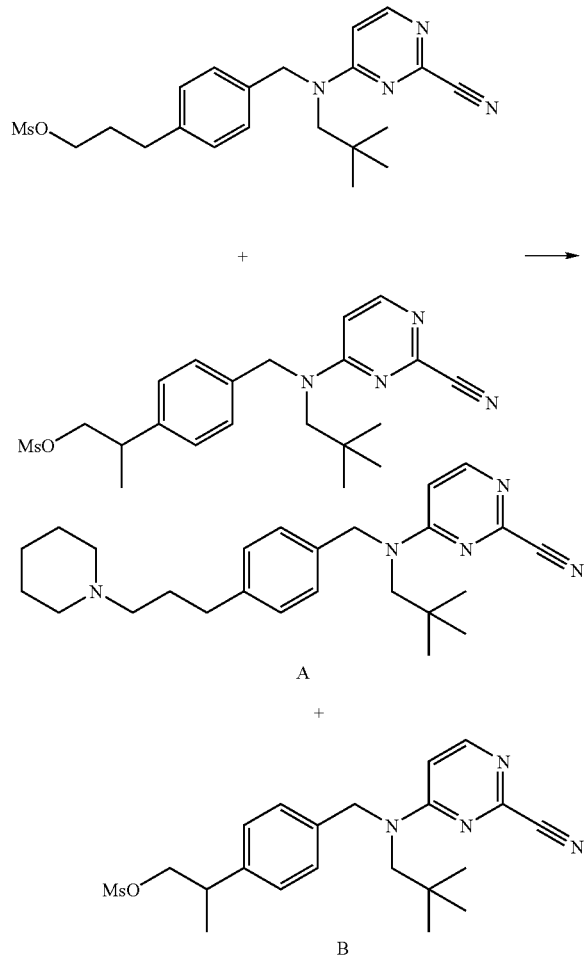

A mixture of methanesulfonic acid 3-(4-{[(2-cyano-pyrimidin-4-yl)-(2,2-dimethyl-propyl)-amino]-methyl}-phenyl)-propyl ester and methanesulfonic acid 2-(4-{[(2-cyano-pyrimidin-4-yl)-(2,2-dimethyl-propyl)-amino]-methyl}-phenyl)-propyl ester (in ratio of 3:1) (130 mg, 0.31 mmoles) is dissolved in 3 ml of DMF and 1-piperizine (0.06 ml, 0.64 mmoles) is added at rt. The mixture is stirred at rt for overnight. Water is added and the organic layer is extracted with AcOEt, dried over magnesum sulfate and concentrated. The crude product is purified by silica gel column chromatography to give 56 mg of desired 4-{(2,2-dimethyl-propyl)-[4-(3-piperidin-1-yl-propyl)-benzyl]-amino}-pyrimidine-2-carbonitrile (A) in 56% yield and 24 mg of desired methanesulfonic acid 2-(4-{[(2-cyano-pyrimidin-4-yl)-(2,2-dimethyl-propyl)-amino]-methyl}-phenyl)-propyl ester (B) in 18% yield.

Methanesulfonic acid 2-(4-{[(2-cyano-pyrimidin-4-yl)-(2,2-dimethyl-propyl)-amino]-methyl}-phenyl)-propyl ester (B)

$^1$H NMR (400 MHz, CDCl$_3$) δ 1.02 (s, 9H), 1.34 (d, 3H), 2.87 (s, 3H), 3.18, (hex, 1H), 3.64 (brs, 2H), 4.22 (dd, 1H), 4.27 (dd, 1H), 4.76 (bsr, 2H), 6.44 (brs, 1H), 6.46 (d, 1H), 7.07 (d, 2H), 7.19 (d, 2H), 8.10 (s, 1H) Rf=0.75 (n-Hexane:AcOEt=1:1)

By repeating the procedures described in Examples 13-41-G, H using appropriate starting material and conditions, the following compounds of formula 13-7 are obtained as identified below in Table 13-7.

TABLE 13-7

13-7

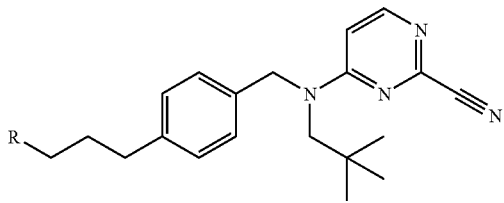

| Example No. | R | Yield (%) | Rf (solvent) | $^1$H NMR(400 MHz, CDCl3, δ) |
|---|---|---|---|---|
| 13-41 |  | 56 | 0.10 (AcOEt:Hexane = 1:1) | 1.02(s, 9H), 1.38-1.46(m, 2H), 1.52-1.87(m, 8H), 2.30-2.43(m, 4H), 2.65(t, 2H), 2.61(t, 2H), 3.66(brs, 2H), 4.74(bsr, 2H), 6.54(brs, 1H), 7.01(d, 2H), 7.14(d, 2H), 8.09(s, 1H) |

TABLE 13-7-continued 13-7

| Example No. | R | Yield (%) | Rf (solvent) | ¹H NMR(400 MHz, CDCl3, δ) |
|---|---|---|---|---|
| 13-42 | (1-methylpiperidin-4-ol) | 69 | 0.05 (AcOEt:Hexane = 1:1) | 1.02(s, 9H), 1.51-1.68(m, 5H), 1.81(pent, 2H), 1.87-1.93(m, 2H), 2.08-2.19(m, 2H), 2.35(t, 2H), 2.61(t, 2H), 2.72-2.82(m, 2H), 3.66(brs, 2H, 2.69-78(m, 1H), 4.74(bsr, 2H), 6.54(brs, 1H), 7.01(d, 2H), 7.14(d, 2H), 8.09(s, 1H) |
| 13-43 | (methyl piperidine-4-carboxylate) | 11 | 0.10 (AcOEt:Hexane = 1:1) | 1.02(s, 9H), 1.28-1.35(m, 1H), 1.96(pent, 2H), 2.08-2.29(m, 4H), 2.58-2.69(m, 4H), 3.06(t, 2H), 3.38-3.46(m, 2H), 3.66(brs, 2H), 4.11(t, 2H), 4.74(bsr, 2H), 6.54(brs, 1H), 7.01(d, 2H), 7.14(d, 2H), 8.09(s, 1H) |

13-44

4-{(2,2-Dimethyl-propyl)-[4-((E)-3-piperidin-1-yl-propenyl)-benzyl]-amino}-pyrimidine-2-carbonitrile

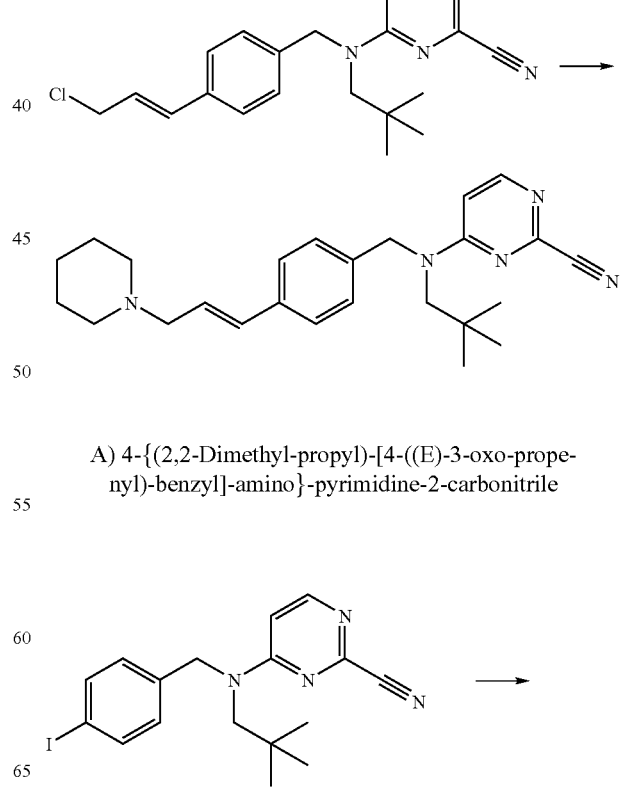

A) 4-{(2,2-Dimethyl-propyl)-[4-((E)-3-oxo-propenyl)-benzyl]-amino}-pyrimidine-2-carbonitrile

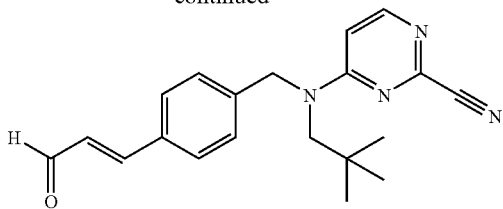

4-[(2,2-Dimethyl-propyl)-(4-iodo-benzyl)-amino]-pyrimidine-2-carbonitrile (1.3 g, 2.5 mmoles), acrolein (0.5 ml, 7.4 mmoles), and triethylamine (0.4 ml, 3.1 mmoles) are dissolved in 25 ml of acetonitrile and Pd(OAc)2 (27 mg, 0.12 mmoles) is added at rt. The mixture is stirred at 80° C. for 18 h. Water is added and the organic layer is extracted with AcOEt, washed with brine, dried over magnesium sulfate and concentrated. The crude product is purified by silica gel column chromatography to give 423 mg of desired 4-{(2,2-dimethyl-propyl)-[4-((E)-3-oxo-propenyl)-benzyl]-amino}-pyrimidine-2-carbonitrile in 39% yield.

$^1$H NMR (400 MHz, CDCl$_3$) δ 1.02 (s, 9H), 3.52 (brs, 2H), 4.79 (brs, 2H), 6.69 (dd, 1H), 7.18 (d, 2H), 7.45 (d, 2H), 7.45 (d, 2H), 7.53 (d, 2H), 8.14 (brs, 2H), 9.70 (d, 2H) Rf=0.60, (n-Hexane:AcOEt)=1:1

B) 4-{(2,2-Dimethyl-propyl)-[4-((E)-3-hydroxy-propenyl)-benzyl]-amino}-pyrimidine-2-carbonitrile

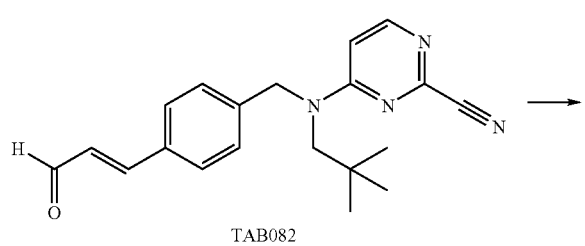

TAB082

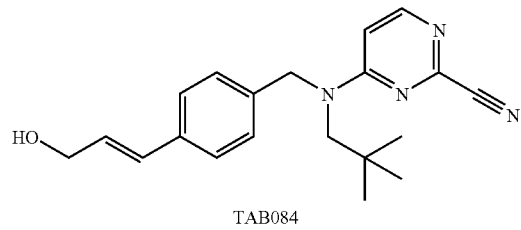

TAB084

13-44A (423 mg, 1.3 mmoles) is dissolved in 5 ml of MeOH and NaBH4 (48 mg, 1.3 mmoles) is added at 0° C. The mixture is stirred at 0° C. for 10 min. The reaction mixture is added 5 ml of acetone, and concentrated. The crude residue is diluted with water and the organic layer is extracted with dichloromethane, washed with brine, dried over magnesium sulfate and concentrated. The crude product is purified by silica gel column chromatography to give 342 mg of desired 4-{(2,2-dimethyl-propyl)-[4-((E)-3-hydroxy-propenyl)-benzyl]-amino}-pyrimidine-2-carbonitrile in 80% yield.

$^1$H NMR (400 MHz, CDCl$_3$) δ 1.02 (s, 9H), 1.44 (t, 1H), 3.47 (brs, 2H), 4.32 (t, 2H), 4.78 (bsr, 2H), 6.35 (dt, 1H), 6.52 (brs, 1H), 6.59 (d, 1H), 7.07 (d, 2H), 7.34 (d, 2H), 8.09 (s, 1H) Rf=0.38 (AcOEt:Hexane=1:1)

C) 4-[[4-((E)-3-Chloro-propenyl)-benzyl]-(2,2-dimethyl-propyl)-amino]-pyrimidine-2-carbonitrile

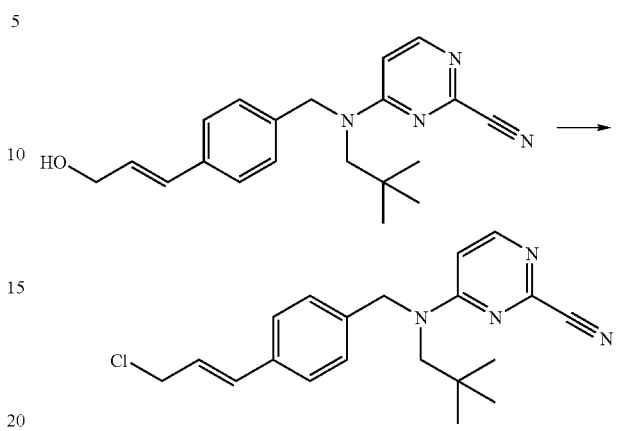

13-44B (342 mg, 1.1 mmoles) and ethyl-diisopropyl-amine (0.42 ml, 2.4 mmoles) are dissolved in 10 ml of dichloromethane and methansulfonyl chloride (0.09 ml, 1.2 mmoles) is added at 0° C. The mixture is stirred at rt for 16 h. Water is added and the organic layer is extracted with dichloromethane, dried over magnesium sulfate and concentrated. The crude product is purified by silica gel column chromatography to give 298 mg of desired 4-[[4-(3-chloro-prop-1-enyl)-benzyl]-(2,2-dimethyl-propyl)-amino]-pyrimidine-2-carbonitrile in 83% yield.

$^1$H NMR (400 MHz, CDCl$_3$) δ 1.02 (s, 9H), 3.47 (brs, 2H), 4.22 (d, 2H), 4.80 (bsr, 2H), 6.30 (dt, 1H), 6.54 (brs, 1H), 6.62 (d, 1H), 7.07 (d, 2H), 7.34 (d, 2H), 8.10 (s, 1H) Rf=0.84 (AcOEt:Hexane=1:1)

D) 4-{(2,2-Dimethyl-propyl)-[4-((E)-3-piperidin-1-yl-propenyl)-benzyl]-amino}-pyrimidine-2-carbonitrile

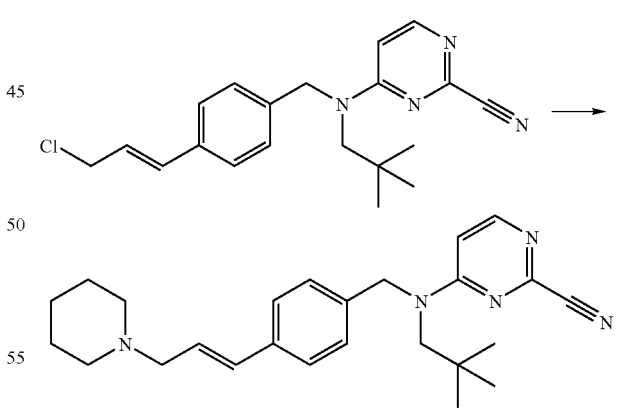

13-44C (88 mg, 0.25 mmoles) is dissolved in 3 ml of DMF and 1-piperizine (0.05 ml, 0.50 mmoles) is added at rt. The mixture is stirred at rt for overnight. Water is added and the organic layer is extracted with AcOEt, dried over magnesium sulfate and concentrated. The crude product is purified by silica gel column chromatography to give 61 mg of desired 4-{(2,2-dimethyl-propyl)-[4-((E)-3-piperidin-1-yl-propenyl)-benzyl]-amino}-pyrimidine-2-carbonitrile in 61% yield.

By repeating the procedure described above using appropriate starting material and conditions, the following compounds of formula 13-8 are obtained as identified below in Table 13-8.

TABLE 13-8

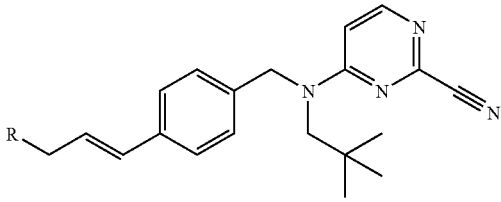

13-8

| Example No. | R | Yield (%) | Rf (solvent) | $^1$H NMR(400 MHz, CDCl3, δ) |
|---|---|---|---|---|
| 13-44 | 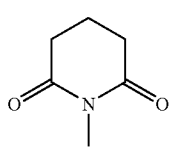 | 61 | 0.10 (AcOEt) | 1.02(s, 9H), 1.38-1.46(m, 2H), 1.53-1.63(m, 4H), 2.41-2.56(m, 4H), 3.10(d, 2H), 3.64(brs, 2H), 4.76(bsr, 2H), 6.30(dt, 1H), 6.44(brs, 1H), 6.46(d, 1H), 7.07(d, 2H), 7.34(d, 2H), 8.10(s, 1H) |
| 13-45 | 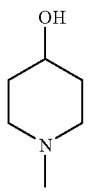 | 57 | 0.29 (AcOEt:Hexane = 1:1) | 1.02(s, 9H), 1.98(pent, 2H), 2.67(t, 4H), 3.64(brs, 2H), 4.32(d, 2H), 4.75(bsr, 2H), 6.17(dt, 1H), 6.37(brs, 1H), 6.57(d, 1H), 7.02(d, 2H), 7.29(d, 2H), 8.08(s, 1H) |
| 13-46 | 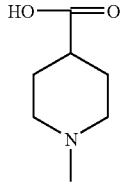 | 69 | 0.10 (AcOEt:Hexane = 1:1) | 1.02(s, 9H), 1.61(brt, 1H), 1.89-2.02(m, 2H), 2.16-2.32(m, 2H), 2.79-2.90(m, 2H), 3.09-3.22(m, 2H), 3.46-3.89(m, 3H), 4.76(bsr, 2H), 6.19-6.32(m, 2H), 6.48(d, 1H), 7.04(d, 2H), 7.32(d, 2H), 8.09(s, 1H) |
| 13-47 | 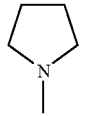 | 29 | 0.35 (MeOH:CH2Cl2 = 1:4) | 1.02(s, 9H), 1.71-2.00(m, 3H), 2.12-2.28(m, 2H), 2.81-3.21(m, 4H), 3.26(d, 2H), 3.65(brs, 2H), 4.76(bsr, 2H), 6.19-6.32(m, 2H), 6.48(d, 1H), 7.04(d, 2H), 7.32(d, 2H), 8.06(s, 1H) |
| 13-48 | 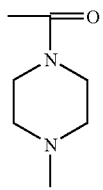 | 48 | 0.10 (AcOEt) | 1.02(s, 9H), 1.81(pent, 4H), 2.59(brs, 4H), 2.81-3.21(m, 4H), 3.28(d, 2H), 3.59(brs, 2H), 4.76(bsr, 2H), 6.32(dt, 1H), 6.36(brs, 1H), 6.50(d, 1H), 7.04(d, 2H), 7.32(d, 2H), 8.09(s, 1H) |
| 13-49 |  | 96 | 0.33 (AcOEt:MeOH = 3:1) | 1.02(s, 9H), 2.08(s, 3H), 2.46-2.55(m, 4H), 3.16(d, 2H), 3.48(t, 2H), 3.64(t, 2H), 3.76(brs, 2H), 4.79(brs, 2H), 6.23(dt, 1H), 6.41(brs, 1H), 6.49(d, 1H), 7.05(d, 2H), 7.32(d, 2H), 8.09(s, 1H) |

TABLE 13-8-continued

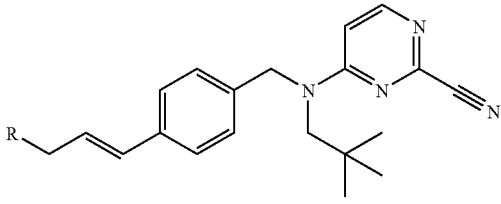

13-8

| Example No. | R | Yield (%) | Rf (solvent) | $^1$H NMR(400 MHz, CDCl3, δ) |
|---|---|---|---|---|
| 13-50 | 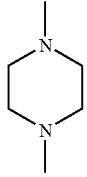 | 59 | 0.26 (MeOH) | 1.02(s, 9H), 2.29(s, 3H), 2.38-2.67(m, 8H), 3.15(d, 2H), 3.66(brs, 2H), 4.79(brs, 2H), 6.27(dt, 1H), 6.42(brs, 1H), 6.49(d, 1H), 7.04(d, 2H), 7.31(d, 2H), 8.08(s, 1H) |
| 13-51 | 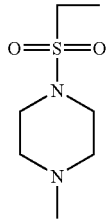 | 83 | 0.07 (AcOEt:MeOH = 3:1) | 1.02(s, 9H), 1.08(t, 3H), 2.42(q, 2H), 2.53(bsr, 8H), 3.16(d, 2H), 3.60(br, 2H), 4.75(br, 2H), 6.26(dt, 1H), 6.47(brs, 1H), 6.49(d, 1H), 7.04(d, 2H), 7.31(d, 2H), 8.08(s, 1H) |
| 13-52 | 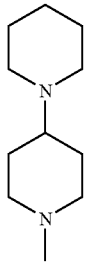 | 79 | 0.50 (AcOEt:MeOH = 9:1) | 1.02(s, 9H), 1.37(t, 3H), 2.57(t, 4H), 2.95(q, 2H), 3.18(d, 2H), 3.33(t, 4H), 3.63(brs, 2H), 4.77(brs, 2H), 6.20(dt, 1H), 6.42(brs, 1H), 6.50(d, 1H), 7.06(d, 2H), 7.32(d, 2H), 8.09(s, 1H) |
| 13-53 | 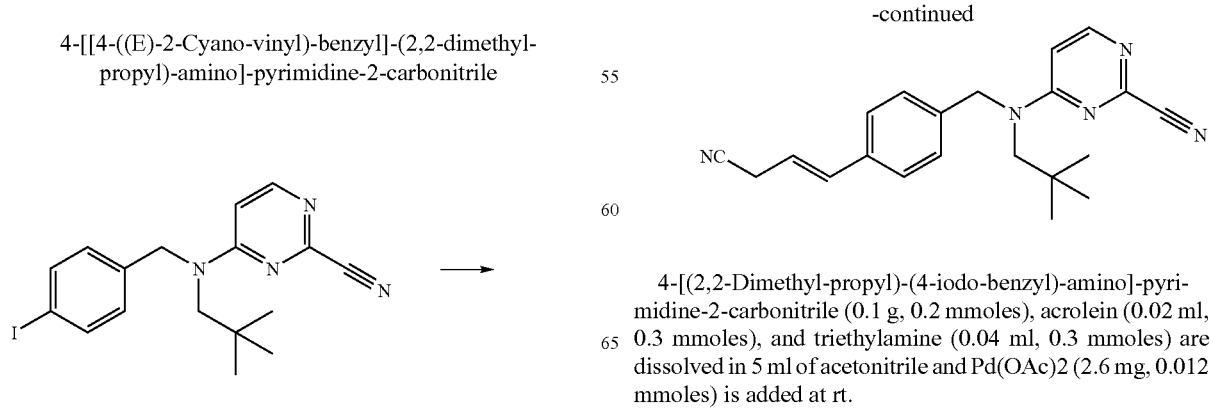 | 73 | 0.10 (MeOH) | 1.02(s, 9H), 1.38-1.69(m, 8H), 1.76-1.83(m, 2H), 2.04(t, 2H), 2.22-2.32(m, 1H), 2.51(brt, 4H), 3.02(d, 2H), 3.11(d, 2H), 3.66(brs, 2H), 4.76(brs, 2H), 6.27(dt, 1H), 6.44(brs, 1H), 6.46(d, 1H), 7.03(d, 2H), 7.31(d, 2H), 8.08(s, 1H) |

13-54

4-[[4-((E)-2-Cyano-vinyl)-benzyl]-(2,2-dimethyl-propyl)-amino]-pyrimidine-2-carbonitrile 4-[(2,2-Dimethyl-propyl)-(4-iodo-benzyl)-amino]-pyrimidine-2-carbonitrile (0.1 g, 0.2 mmoles), acrolein (0.02 ml, 0.3 mmoles), and triethylamine (0.04 ml, 0.3 mmoles) are dissolved in 5 ml of acetonitrile and Pd(OAc)2 (2.6 mg, 0.012 mmoles) is added at rt.

The mixture is stirred at 100° C. for overnight. Water is added and the organic layer is extracted with AcOEt, washed with brine, dried over magnesium sulfate and concentrated. The crude product is purified by silica gel column chromatography to give 423 mg of desired 4-[[4-((E)-2-cyano-vinyl)-benzyl]-(2,2-dimethyl-propyl)-amino]-pyrimidine-2-carbonitrile in 45% yield.

By repeating the procedure described above using appropriate starting material and conditions, the following compounds of formula 13-9 are obtained as identified below in Table 13-9.

TABLE 13-9

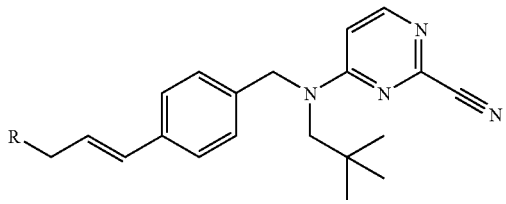

13-9

| Example No. | R | Yield (%) | Rf (solvent) | $^1$H NMR(400 MHz, CDCl3, δ) |
|---|---|---|---|---|
| 13-54 | —CN | 45 | 0.56 (Hexane:AcOEt = 1:1) | 1.03(s, 9H), 3.54(brs, 2H), 4.86(brs, 2H), 5.85(d, 1H), 6.48(brs, 1H), 6.46(d, 1H), 7.15(d, 2H), 7.40(d, 2H), 7.76(d, 1H), 8.14(s, 1H) |
| 13-55 | ![triazole] | 43 | 0.47 (AcOEt:MeOHe = 9:1) | 1.02(s, 9H), 3.64(brs, 2H), 4.78(brs, 2H), 4.95(d, 2H), 6.32(dt, 1H), 6.42(brs, 1H), 6.60(d, 1H), 7.07(d, 2H), 7.33(d, 2H), 7.97(s, 1H), 8.10(brs, 1H), 8.12(s, 1H) |
| 13-56 | ![triazole] | 57 | 0.12 (AcOEt:Hexane = 1:1) | 1.02(s, 9H), 3.64(brs, 2H), 4.78(br, 2H), 5.16(d, 2H), 6.32(dt, 1H), 6.46(brs, 1H), 6.62(d, 1H), 7.07(d, 2H), 7.33(d, 2H), 7.60(s, 1H), 7.73(s, 1H), 8.09(s, 1H) |

The invention claimed is:

1. A compound of formula IV, or a pharmaceutically acceptable salt thereof

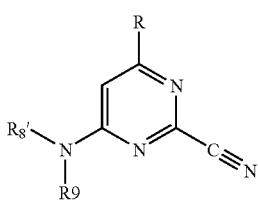

IV in which

R is H, —R2, —OR2 or NR1R2, wherein R1 is H, lower alkyl or $C_3$ to $C_{10}$ cycloalkyl, and R2 is lower alkyl or $C_3$ to $C_{10}$ cycloalkyl, and wherein R1 and R2 are independently, optionally substituted by halo, hydroxy, lower alkoxy, CN, $NO_2$, or optionally mono- or di-lower alkyl substituted amino;

R8' is optionally substituted aryl-lower alkyl wherein R8' is optionally substituted by R10 which represents from 1 to 4 substituents selected from halo, hydroxy, CN, $NO_2$, —O—C(O)—, optionally substituted (lower-alkyl, $C_3$-$C_{10}$cycloalkyl, lower-alkoxy, lower-alkenyl, lower-alkynyl, optionally mono- or di-lower alkyl-substituted amino or N-heterocyclyl), where N-heterocyclyl denotes a saturated, partially unsaturated or aromatic nitrogen containing heterocyclic moiety attached via a nitrogen atom thereof having from 3 to 8 ring atoms optionally containing a further 1, 2 or 3 heteroatoms selected from N, NR6, O , S, S(O) or S(O)$_2$ wherein R6 is H or optionally substituted (lower alkyl, carboxy, formyl, acetyl, propionyl, benzoyl, amido, aryl, S(O) or S(O)$_2$), and wherein the N-heterocyclyl is optionally fused in a bicyclic structure with a benzene or pyridine ring, and wherein the N-heterocyclyl is optionally linked in a spiro structure with a 3 to 8 membered cycloalkyl or heterocyclic ring wherein the heterocyclic ring has from 3 to 10 ring members and contains from 1 to 3 heteroatoms selected from N, NR6, O, S, S(O) or S(O)$_2$ wherein R6 is as defined above;

wherein R10 is optionally substituted by R11 which represents from 1 to 4 substituents selected from halo, hydroxy, CN, $NO_2$, oxo, optionally substituted (optionally mono- or di-lower alkyl-substituted amino, lower alkyl, optionally-lower alkyl substituted COOH, sulphinyl, sulphonyl, or N-heterocyclyl which is as defined above;

wherein R11 is optionally substituted by R12 which represents from 1 to 4 substituents selected from halo, hydroxy, CN, $NO_2$, oxo, hydroxy lower alkyl, $C_3$-$C_{10}$cycloalkyl, optionally lower alkyl-substituted carboxy, hydroximine, or N-heterocyclyl as defined above, and wherein R9 is H or optionally substituted lower alkyl, and wherein R9 is optionally substituted by halo, hydroxy, oxo, lower alkoxy, CN, $NO_2$, or optionally mono- or di-lower alkyl substituted amino.

2. The compound according to claim 1, or a pharmaceutically acceptable salt thereof, wherein the compound is selected from compounds of formula:

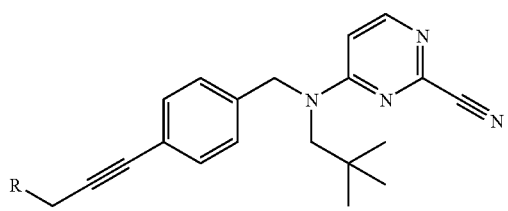

wherein R is selected from the group consisting of:

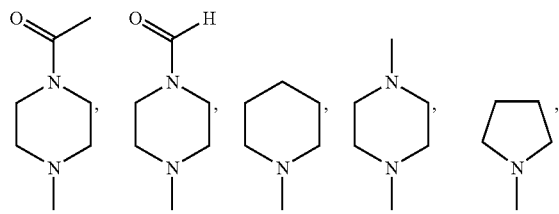

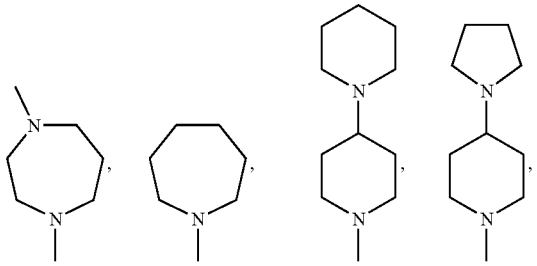

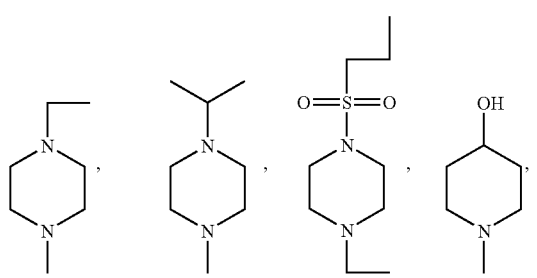

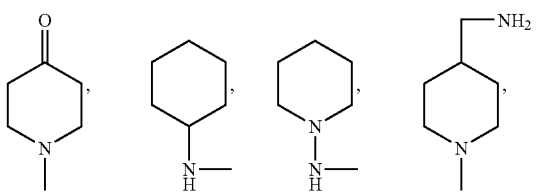

-continued

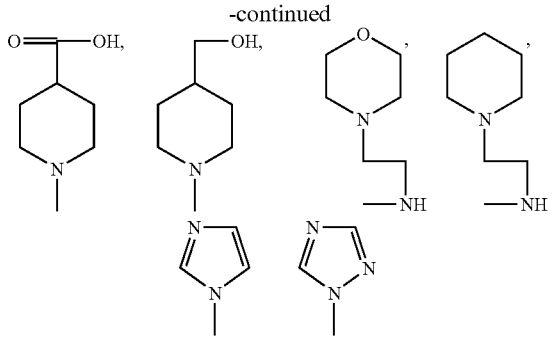

and —$NH_2$.

3. The compound according to claim 1, or a pharmaceutically acceptable salt thereof, wherein the compound is selected from compounds of formula:

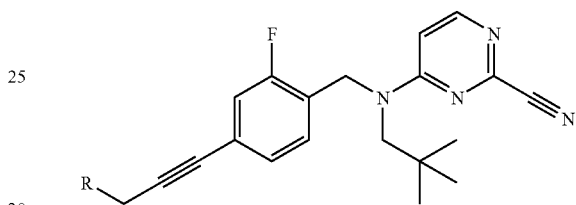

wherein R is

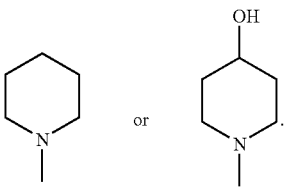

4. The compound according to claim 1, or a pharmaceutically acceptable salt thereof, wherein the compound is selected from compounds of formula:

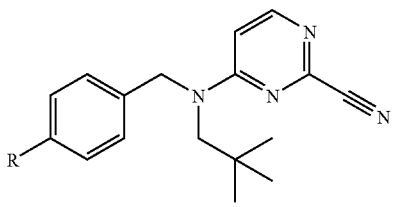

wherein R is selected from the group consisting of:

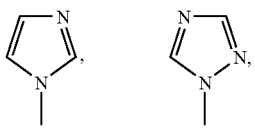

and —CH=$CH_2$.

5. The compound according to claim 1, or a pharmaceutically acceptable salt thereof, wherein the compound is selected from compounds of formula:

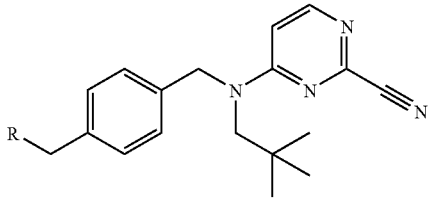

wherein R is selected from the group consisting of:

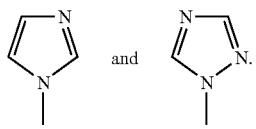

6. The compound according to claim 1, or a pharmaceutically acceptable salt thereof, wherein the compound is selected from compounds of formula:

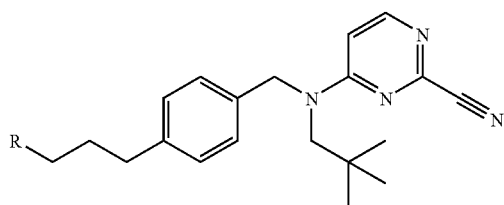

wherein R is selected from the group consisting of:

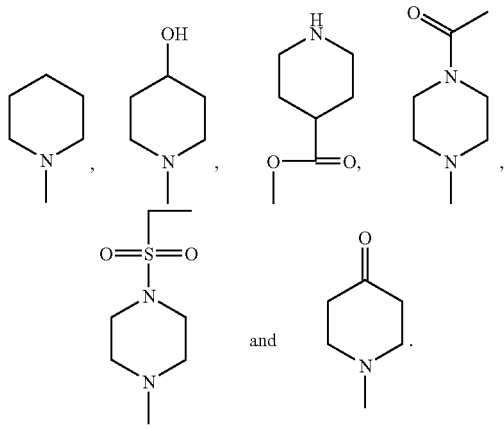

7. The compound according to claim 1, or a pharmaceutically acceptable salt thereof, wherein the compound is selected from compounds of formula:

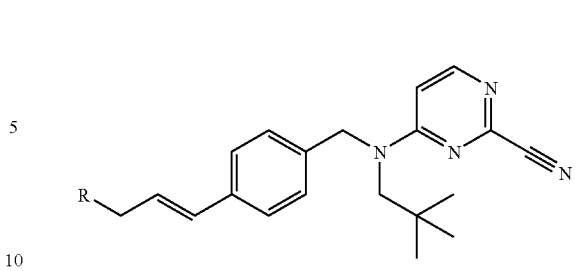

wherein R is selected from the group consisting of:

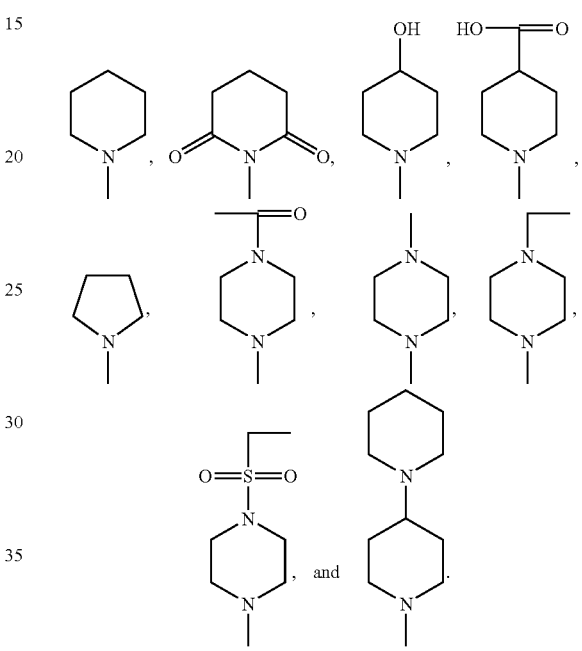

8. The compound according to claim 1, or a pharmaceutically acceptable salt thereof, wherein the compound is selected from compounds of formula:

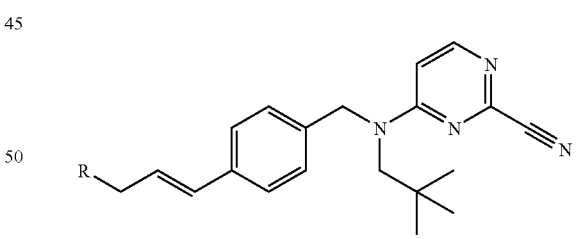

wherein R is selected from the group consisting of: —CN,

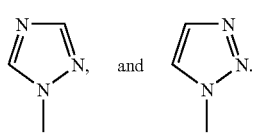

9. The compound according to claim 1, which is selected from the group consisting of 4-[(2,2-dimethyl-propyl)-(4-[1,2,4]triazol-1-yl-benzyl)-amino]-pyrimidine-2-carbonitrile, 4-{(2,2-dimethyl-propyl)-[4-(3-methyl-3H-imidazol-4-yl)-benzyl]-amino}-pyrimidine-2-carbonitrile, 4-[(2,2-dimethyl-propyl)-(4-oxazol-2-yl-benzyl)-amino]-pyrimidine-2-carbonitrile, 4-[(2,2-dimethyl-propyl)-(4-[1,2,4]triazol-1-ylmethyl-benzyl)-amino]-pyrimidine-2-carbonitrile, 4-[(2,2-dimethyl-propyl)-(4-ethyl-benzyl)-amino]-pyrimidine-2-carbonitrile, 4-((2,2-dimethyl-propyl)-{4-[3-(4-hydroxyimino-piperidin-1-yl)-prop-1-ynyl]-benzyl}-amino)-pyrimidine-2-carbonitrile, and methanesulfonic acid 2-(4-{[(2-cyano-pyrimidin-4-yl)-(2,2-dimethyl-propyl)-amino]-methyl}-phenyl)-propyl ester.

10. A pharmaceutical composition comprising a compound according to claim 1 as an active ingredient and a pharmaceutically acceptable carrier material.

11. A method of treating a patient suffering from or susceptible to a disease or medical condition in which cathepsin K is implicated selected from the group consisting of osteoarthritis, rheumatoid arthritis and osteoporosis, comprising administering a compound according to claim 1, or a pharmaceutically acceptable salt thereof, to the patient.

* * * * *